(12) United States Patent
Xu et al.

(10) Patent No.: US 11,584,883 B2
(45) Date of Patent: Feb. 21, 2023

(54) CONJUGATED POLYMERS AND METHODS OF USE

(71) Applicant: BioLegend, Inc., San Diego, CA (US)

(72) Inventors: Xinshe Xu, San Diego, CA (US); Jing Wang, San Diego, CA (US); Matthew Yerou, San Diego, CA (US)

(73) Assignee: BIOLEGEND, INC., San Diego, CA (US)

( * ) Notice: Subject to any disclaimer, the term of this patent is extended or adjusted under 35 U.S.C. 154(b) by 430 days.

(21) Appl. No.: 16/702,146

(22) Filed: Dec. 3, 2019

(65) Prior Publication Data

US 2020/0239766 A1 Jul. 30, 2020

Related U.S. Application Data

(63) Continuation of application No. PCT/US2018/043911, filed on Jul. 26, 2018.

(60) Provisional application No. 62/538,583, filed on Jul. 28, 2017.

(51) Int. Cl.
C09K 11/06 (2006.01)
C08G 61/10 (2006.01)
G01N 33/58 (2006.01)

(52) U.S. Cl.
CPC ............ *C09K 11/06* (2013.01); *C08G 61/10* (2013.01); *G01N 33/582* (2013.01); *C08G 2261/12* (2013.01); *C08G 2261/1424* (2013.01); *C08G 2261/1432* (2013.01); *C08G 2261/1644* (2013.01); *C08G 2261/1646* (2013.01); *C08G 2261/312* (2013.01); *C08G 2261/3142* (2013.01); *C08G 2261/522* (2013.01); *C08G 2261/94* (2013.01); *C09K 2211/1416* (2013.01); *C09K 2211/1425* (2013.01)

(58) Field of Classification Search
CPC ............ C09K 11/06; C09K 2211/1416; C09K 2211/1425; C08G 61/10; C08G 2261/12; C08G 2261/1432; C08G 2261/1424; C08G 2261/1644; C08G 2261/3142; C08G 2261/312; C08G 2261/522; C08G 2261/94; C08G 2261/1646; G01N 33/582
See application file for complete search history.

(56) References Cited

U.S. PATENT DOCUMENTS

| | | |
|---|---|---|
| 4,436,745 A | 3/1984 | York, Jr. |
| 7,144,950 B2 | 12/2006 | Bazan et al. |
| 7,214,489 B2 | 5/2007 | Bazan et al. |
| 7,270,956 B2 | 9/2007 | Bazan et al. |
| 7,629,448 B2 | 12/2009 | Bazan et al. |
| 7,666,594 B2 | 2/2010 | Bazan et al. |
| 7,811,755 B2 | 10/2010 | Bazan et al. |
| 7,897,684 B2 | 3/2011 | Bazan et al. |
| 7,914,984 B2 | 3/2011 | Bazan et al. |
| 8,101,416 B2 | 1/2012 | Bazan et al. |
| 8,110,673 B2 | 2/2012 | Bazan et al. |
| 8,158,444 B2 | 4/2012 | Gaylord et al. |
| 8,227,187 B2 | 7/2012 | Bazan et al. |
| 8,338,532 B2 | 12/2012 | Bazan et al. |
| 8,354,239 B2 | 1/2013 | Gaylord et al. |
| 8,362,193 B2 | 1/2013 | Gaylord et al. |
| 8,455,613 B2 | 6/2013 | Gaylord et al. |
| 8,546,081 B2 | 10/2013 | Bazan et al. |
| 8,575,303 B2 | 11/2013 | Gaylord et al. |
| 8,669,055 B2 | 3/2014 | Bazan et al. |
| 8,759,444 B2 | 6/2014 | Bazan et al. |
| 8,802,450 B2 | 8/2014 | Gaylord et al. |
| 8,835,113 B2 | 9/2014 | Bazan et al. |
| 8,841,072 B2 | 9/2014 | Bazan et al. |
| 8,969,509 B2 | 3/2015 | Liu et al. |
| 9,085,799 B2 | 7/2015 | Bazan et al. |
| 9,139,869 B2 | 9/2015 | Gaylord et al. |
| 9,159,465 B2 | 10/2015 | Bazan et al. |
| 9,371,559 B2 | 6/2016 | Bazan et al. |
| 9,383,353 B2 | 7/2016 | Gaylord et al. |
| 9,412,949 B2 | 8/2016 | Liu |
| 9,547,008 B2 | 1/2017 | Gaylord et al. |
| 9,623,123 B2 | 4/2017 | Liu |
| 9,758,625 B2 | 9/2017 | Bartholomew et al. |
| RE46,817 E | 5/2018 | Bazan et al. |
| 10,001,473 B2 | 6/2018 | Bazan et al. |
| 10,094,838 B2 | 10/2018 | Gaylord et al. |
| 10,107,818 B2 | 10/2018 | Gaylord et al. |

(Continued)

FOREIGN PATENT DOCUMENTS

| | | |
|---|---|---|
| CN | 106084186 A | 11/2016 |
| DE | 102009030847 A1 | 12/2010 |

(Continued)

OTHER PUBLICATIONS

Setayesh et al, Bridging the gap between polyfluorene and ladder-poly-p-phenylene: synthesis and characterization of poly-2,8-indenofluorene. Macromolecules 2000, vol. 33, pp. 2016-2020 (Year: 2000).*

Amara et al., Conjugated polymers with geminal trifluoromethyl substituents derived from hexafluoroacetone. Macromolecules 2006, vol. 39, pp. 5753-5759. (Year: 2006).*

Ma et al. Indenofluorene based water soluble conjugated oligomers for Hg2+ detection. Sensors and Actuators B, 2013 vol. 176, pp. 132-140. (Year: 2013).*

Destri et al., Synthesis and Crystal Structure and Optical Properties of Fluorenic-Core Oligomers, Journal of Materials Chemi, Royal Society of Chemistry, vol. 12, Jan. 1, 2002, pp. 924-933.

(Continued)

*Primary Examiner* — Shafiqul Haq
(74) *Attorney, Agent, or Firm* — Kilpatrick Townsend & Stockton LLP

(57) ABSTRACT

The present disclosure provides fluorescent polyindenofluorene polymers or macromers with unique optical properties that are stable. The polymeric fluorophores are useful in various bioassays formats. The inventive polymers are useful in assays relying on fluorescence resonance energy transfer (FRET) mechanisms where two fluorophores are used.

23 Claims, 13 Drawing Sheets

(56) References Cited

U.S. PATENT DOCUMENTS

| | | |
|---|---|---|
| 10,126,302 B2 | 11/2018 | Gaylord et al. |
| 10,240,004 B2 | 3/2019 | Bartholomew et al. |
| 10,288,620 B2 | 5/2019 | Gaylord et al. |
| 10,302,648 B2 | 5/2019 | Gaylord et al. |
| 10,365,271 B2 | 7/2019 | Bazan et al. |
| 10,365,285 B2 | 7/2019 | Gaylord et al. |
| 10,458,989 B2 | 10/2019 | Gaylord et al. |
| 10,472,521 B2 | 11/2019 | Radford et al. |
| 10,481,161 B2 | 11/2019 | Gaylord et al. |
| 10,533,092 B2 | 1/2020 | Bartholomew et al. |
| RE47,874 E | 2/2020 | Bazan et al. |
| 10,604,657 B2 | 3/2020 | Bartholomew et al. |
| 10,605,813 B2 | 3/2020 | Liang et al. |
| 10,641,777 B2 | 5/2020 | Gaylord et al. |
| 10,703,864 B2 | 7/2020 | Bartholomew et al. |
| 11,155,714 B2 | 10/2021 | Xu et al. |
| 2005/0123802 A1 | 6/2005 | Park et al. |
| 2006/0149016 A1 | 7/2006 | O'Dell et al. |
| 2007/0031698 A1* | 2/2007 | Towns .............. C08G 61/12 428/690 |
| 2009/0247728 A1 | 10/2009 | Pan et al. |
| 2012/0068121 A1 | 3/2012 | Sparrowe et al. |
| 2012/0108731 A1 | 5/2012 | Heun et al. |
| 2012/0232238 A1* | 9/2012 | Katz .............. H01L 51/0068 977/734 |
| 2013/0109029 A1 | 5/2013 | Liu et al. |
| 2014/0091300 A1 | 4/2014 | Pan et al. |
| 2018/0009989 A1 | 1/2018 | Liang et al. |
| 2018/0364245 A1 | 12/2018 | Martin et al. |
| 2019/0025295 A1 | 1/2019 | Bazan et al. |
| 2019/0033317 A1 | 1/2019 | Gaylord et al. |
| 2019/0194467 A1 | 6/2019 | Liang et al. |
| 2019/0204328 A1 | 7/2019 | Gaylord et al. |
| 2019/0346450 A1 | 11/2019 | Gaylord et al. |
| 2019/0376959 A1 | 12/2019 | Bazan et al. |
| 2019/0376977 A1 | 12/2019 | Gaylord et al. |
| 2020/0062966 A1 | 2/2020 | Bartholomew et al. |
| 2020/0141943 A1 | 5/2020 | Gaylord et al. |
| 2020/0181412 A1 | 6/2020 | Bartholomew et al. |
| 2020/0200761 A1 | 6/2020 | Liang et al. |
| 2020/0270400 A1 | 8/2020 | Bartholomew et al. |
| 2020/0284785 A1 | 9/2020 | Bazan et al. |
| 2022/0002552 A1 | 1/2022 | Xu et al. |

FOREIGN PATENT DOCUMENTS

| | | |
|---|---|---|
| EP | 1491568 A1 | 12/2004 |
| EP | 1533289 A1 | 5/2005 |
| EP | 3658648 | 10/2021 |
| GB | 2355457 A1 | 4/2001 |
| WO | 2008009343 A1 | 1/2008 |
| WO | 2008100344 A2 | 8/2008 |
| WO | 2010136112 A1 | 12/2010 |
| WO | 2012002911 A1 | 1/2012 |
| WO | 2012163464 A1 | 12/2012 |

OTHER PUBLICATIONS

Eisleb, Neue Synthesen Mit Natriumamids, Chemische Berichte, vol. 74, No. 8, Jan. 1, 1941, pp. 1433-1450.

European Application No. EP18752988.8, Office Action dated Dec. 18, 2020, 3 pages.

France et al., The Condensation of Fluorene with Acetone. Part III Formation of fluoranthene derivatives, Journal of the Chemical Society, Jan. 1, 1945, 7 pages.

Jiang et al., Multifunctional Fluorene-Based Oligomers with Novel Spiro-Annulated Triarylamine: Efficient. Stable Deep-Blue Electroluminescence. Good Hole Injection, and Transporting Materials with Very High Tg, Advanced Functional Materials, vol. 19, No. 24, Dec. 23, 2009, pp. 3987-3995.

Marsitzky et al., Poly-2,8-(indenofluorene-co-anthracene)—A Colorfast Blue-Light-Emitting Random Copolymer, Advanced Materials, vol. 13 No. 14, Jul. 18, 2001, pp. 1096-1099.

International Application No. PCT/US2017/041187, International Search Report and Written Opinion dated Nov. 20, 2017, 20 pages.

International Application No. PCT/US2018/043911, International Search Report and Written Opinion dated Oct. 23, 2018, 17 pages.

Pu et al., Mannose-Substituted Conjugated Polyelectrolyte and Oligomer as an Intelligent Energy Transfer Pair for Label-Free Visual Detection of Concanavalin A, Macromolecules, vol. 43, No. 23, Dec. 14, 2010, pp. 9690-9697.

Wang et al., Broadband Spectra with Fluorescence and Phosphorescence Dual Emission From Bichromophoric Platinum Metallomesogens Containing a 6,12-Dihydro-Indeno[1,2-b]Fluorene Linkage, RSC Advances, vol. 6, No. 51, Jan. 1, 2016, pp. 45864-45872.

Wong, Synthesis, Structures, and Photoinduced Electron Transfer Reaction in the 9,9'-Spirobifluorene-Bridged Bipolar Systems, The Journal of Organic Chemistry, vol. 71, No. 2, Dec. 21, 2005, pp. 456-465.

European Application No. 18752988.8, Notice of Decision to Grant dated Sep. 30, 2021, 2 pages.

European Application No. 21197215.3, Extended European Search Report dated Mar. 2, 2022, 8 pages.

International Application No. PCT/US2018/043911, International Preliminary Report on Patentability dated Feb. 6, 2020, 12 pages.

* cited by examiner

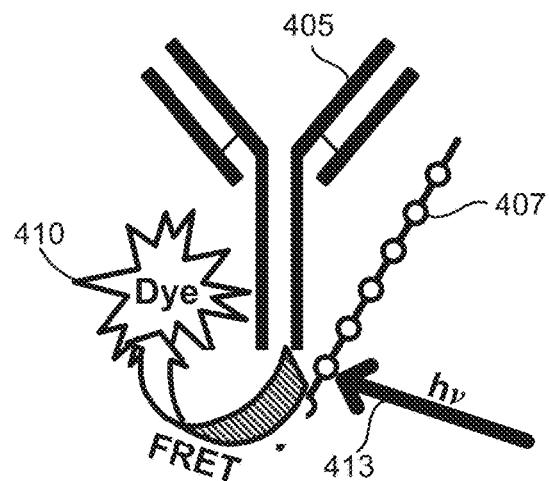
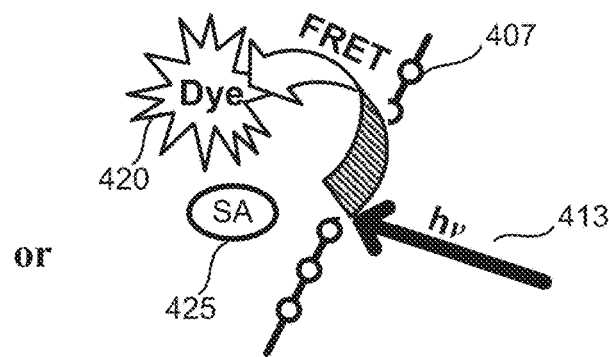
FIG. 4A    FIG. 4B
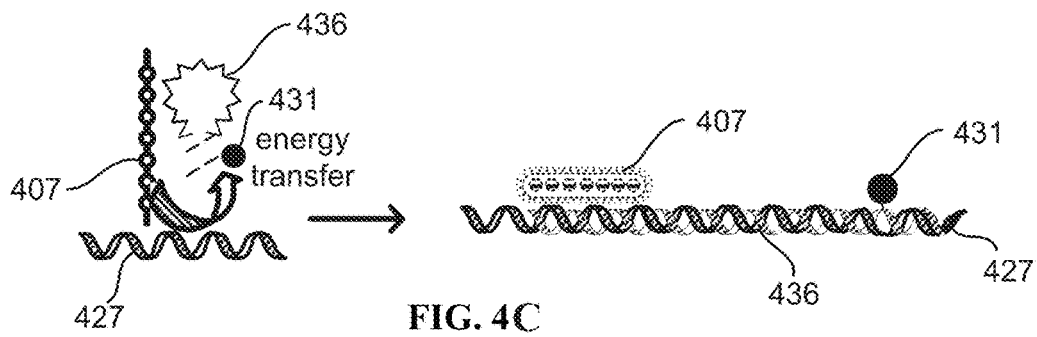
FIG. 4C
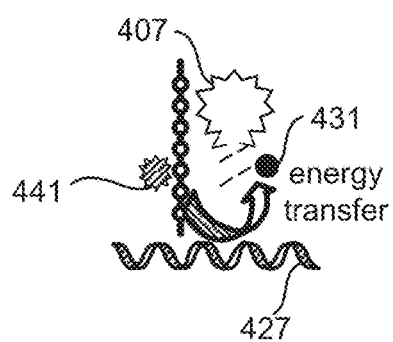
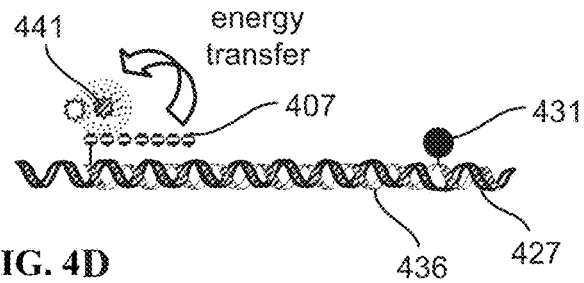
FIG. 4D energy transfer energy transfer energy transfer

CONJUGATED POLYMERS AND METHODS OF USE

CROSS-REFERENCES TO RELATED APPLICATIONS

The present application is a continuation of PCT Application No. PCT/US2018/043911, filed on Jul. 26, 2018, which claims priority to U.S. Patent Application No. 62/538,583, filed Jul. 28, 2017, the disclosure of which is hereby incorporated by reference in its entirety for all purposes.

BACKGROUND OF THE INVENTION

Common dyes like Pacific Blue™, Alexa Fluor® 488 and Cy5 have high quantum yields, but limited extinction coefficients. Alternative reporters like phycobiliproteins offer much greater absorbance cross-sections, producing brighter signals, but are limited by rapid photobleaching and sensitivity to fixation.

Fluorophores are important in various bioassays formats. In fact, fluorescence is a common method for bioanalysis and biodetection and fluorescent labels are important in these applications. Some assays rely on fluorescence resonance energy transfer (FRET) mechanisms where two fluorophores are used. In these assays, energy is transferred between a donor fluorophore and an acceptor fluorophore if the two fluorophore are in close proximity to one another. Excitation of the "donor" by an energy source (e.g. UV light) produces an energy transfer to the "acceptor" if the two fluorophores are within a given proximity. In turn, the acceptor emits light at its characteristic wavelength. In order for FRET to occur, the fluorescence emission spectrum of the donor molecule must overlap with the absorption or excitation spectrum of the acceptor chromophore.

Polyindenofluorene polymers or macromers have well-defined structure, unique optical properties and are stable. Because the extinction coefficient of a macromer is directly proportional to the degree of polymerization (or number of repeat units), macromers are designed to improve brightness. Further, as these materials are derived from common synthetic organic and polymer chemistry techniques, it is possible to manufacture reagents which are more defined and reproducible, in terms of size, conjugation sites, physical properties, and optical properties.

Unlike say quantum dots, conjugated macromers have discrete excitation spectra, similar to that of organic dyes, which minimizes potential issues with cross-beam compensation.

In view of the foregoing, there is a need in the art for new polyindenofluorene macromers that are water-soluble and brighter than currently available technologies. The present disclosure satisfies these and other needs.

BRIEF SUMMARY OF THE INVENTION

In one embodiment, this disclosure provides a macromer of formula I or II:

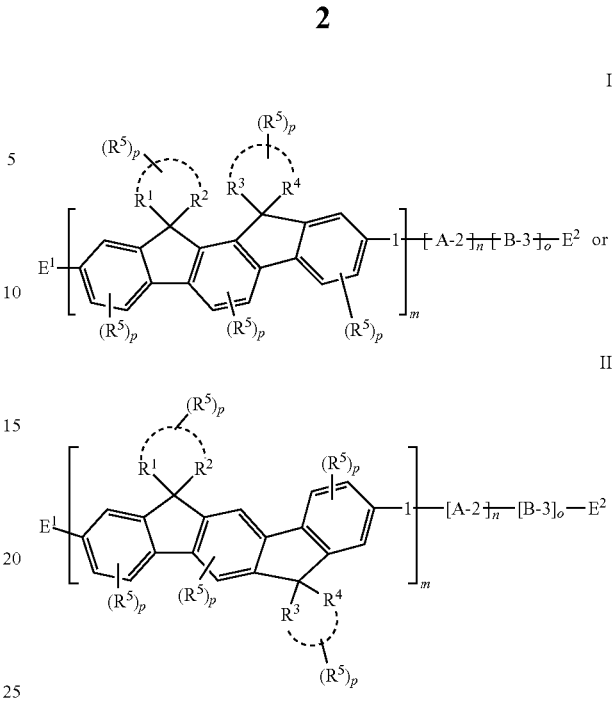

wherein each of $R^1$, $R^2$, $R^3$ and $R^4$ are each independently a member selected from the group of hydrogen, an optionally substituted $C_1$-$C_{10}$ alkyl, an optionally substituted $C_1$-$C_{18}$ alkoxy, optionally substituted $C_6$-$C_{18}$ aryl, optionally substituted $C_4$-$C_{18}$ acyl, optionally substituted $C_4$-$C_{18}$ acyloxy, $NR^aR^b$, wherein $R_a$ and $R_b$ are each independently hydrogen or lower alkyl, a water soluble group, ethylene oxide oligomers and an ethylene oxide oligomer methyl ether;

alternatively, $R^1$ and $R^2$ and/or $R^3$ and $R^4$ together with the carbons to which they are attached, join to form a an optionally substituted 4-, 5-, or 6-membered ring;

each $R^5$ is independently a member selected from the group of halo, alkyl, alkoxy, amino, ethylene oxide oligomers and an ethylene oxide oligomer methyl ether;

each p is a value from 0-3;

m is a value selected from the group consisting of 1-10,000;

each of A and B, can be present or absent and can each be the same or different, and each is selected from the group of an aromatic group or heteroaromatic group, which group completes a π-conjugated backbone;

each of 1, 2 and 3 can be present or absent and can each be the same or different, and each is selected from the group of an aromatic group or heteroaromatic group, which group completes a π-conjugated backbone;

n and o are each independently a value selected from the group consisting of 0-10,000, wherein the monomers within m, n, and o may be the same or different;

$E^1$ and $E^2$ are each independently a member selected from the group consisting of hydrogen, halogen, alkynyl, optionally substituted aryl, optionally substituted heteroaryl, halo, substituted aryl, boronic acid substituted aryl, boronic ester substituted aryl, boronic ester, boronic acid, optionally substituted fluorene and aryl or heteroaryl substituted with one or more pendant chains terminated with: i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule; and wherein the macromer of formula I or II can be an alternating copolymer, a block copolymer, a random copolymer or a graph copolymer between $E^1$ and $E^2$.

In another embodiment, the present disclosure provides a method for detecting an analyte in a sample, the method comprising:

(a) combining the sample and a macromer of formula I or formula II;

(b) exciting the macromer with light; and (c) detecting fluorescence from the macromer, thereby detecting the analyte.

The macromer conjugated to a biomolecule (e.g., an antibody) can be used as a direct reporter, for example, in a bioassay (e.g., an immunoassay). Excitation of the macromer with light can result in macromer emission, indicating the presence of the antibody in the assay or assay solution.

In yet another embodiment, the present invention provides a method for detecting a target biomolecule in a sample, the method comprising:

providing a sample that is suspected of containing a target analyte;

providing a macromer of formula I or II conjugated to a capture molecule, wherein the capture molecule is capable of interacting with the target analyte;

contacting the sample with the capture molecule and the conjugated macromer under conditions in which the capture molecule can bind to the target analyte if present;

applying a light source to the sample that excites the conjugated macromer; and detecting whether light is emitted from the conjugated macromer.

In certain aspects, the method is performed in vivo or alternatively, in vitro. In certain aspects, the sample contains a living cell. In certain aspects, the analyte is a nucleic acid which comprises a genetic point mutation, deletion or insertion relative to a control nucleic acid. The control nucleic acid may contain a genetic mutation. In certain aspects, the detection of the nucleic acid indicates the presence of a cancer in the sample.

These and other aspects, objects and advantages will become more apparent when read with the detailed description and figures which follow.

BRIEF DESCRIPTION OF THE DRAWINGS

FIGS. 4A-D illustrate embodiments of the present disclosure; FIG. 4A illustrates an antibody labeled with a dye and a macromer according to the disclosure; FIG. 4B illustrates streptavidin labeled with a dye and labeled with a macromer according to the disclosure; FIG. 4C illustrates a nucleic acid probe sequence labeled with a quencher molecule conjugated to a macromer of the disclosure; and FIG. 4D illustrates a nucleic acid probe sequence labeled with a quencher molecule and macromer according to the disclosure.

FIG. 5A shows a macromer linked to a first antibody bound to a second antibody with a dye; FIG. 5B illustrates a macromer and dye labeled antibodies recognize a common target; FIG. 5C illustrates an antibody with a linked dye and biotin and a second bioconjugate of streptavidin with a macromer appended thereto; and FIG. 5D illustrates a nucleic acid with a dye and biotin bound thereto and streptavidin with a macromer conjugated thereto.

FIG. 7A depicts a macromer with a linked dye and a biomolecule resulting energy transfer; FIG. 7B illustrates a macromer with a conjugated streptavidin and a linked dye; and FIG. 7C illustrates a macromer conjugated to a nucleic acid and a dye.

FIG. 8A shows a biotinylated antibody interacting with a covalent conjugate of a macromer; FIG. 8B shows a biotinylated antibody bound to moiety linked to a macromer having a linked dye; FIG. 8C shows a biotinylated nucleic acid interacting with a covalent moiety of a macromer; FIG. 8D shows a biotinylated nucleic acid bound to a linked moiety of a macromer having a linked dye; FIG. 8E shows a nucleic acid with digoxygenin moiety interacting with a covalently linked antibody of the macromer 801; and FIG. 8F shows a nucleic acid with digoxygenin moiety and a covalent antibody to a macromer dye tandem complex.

FIG. 9A shows a primary antibody 905 bound to an analyte wherein a secondary antibody having a macromer appended thereto is added; FIG. 9B shows a target analyte binding to a primary antibody with a linked macromer.

FIG. 10A shows a primary antibody that binds an analyte, and a secondary antibody with a biotin is then added, thereafter a macromer with a streptavidin is added to generate a sandwich complex; FIG. 10B shows a biotin labeled primary antibody with an analyte bound, thereafter, a streptavidin linked to a macromer is added.

FIG. 11A shows UCHT1 Pacific Blue (Clone: UCHT1; Conjugate: Pacific Blue™; Signal to Noise: 60; Stain Index: 10; Antibody Conc.: 0.5 μg); FIG. 11B shows P43 (Clone: UCHT1; Conjugate: P43; Signal to Noise: 507; Stain Index: 71; Antibody Conc.: 0.5 μg); and FIG. 11C shows P100 (Clone: UCHT1; Conjugate: P100; Signal to Noise: 517; Stain Index: 76; Antibody Conc.: 0.5 μg).

FIG. 12A shows Pacific Blue (Clone: dG9; Conjugate: Pacific Blue™; Signal to Noise: 33; Stain Index: 9; Antibody Conc.: 0.25 μs); FIG. 12B shows P43 (Clone: dG9; Conjugate: P43; Signal to Noise: 46; Stain Index: 17; Antibody Conc.: 0.25 μg) and FIG. 12C shows P100 (Clone: dG9; Conjugate: P100; Signal to Noise: 41; Stain Index: 15; Antibody Conc.: 0.25 μs).

DETAILED DESCRIPTION

I. Definitions

Figure 1:
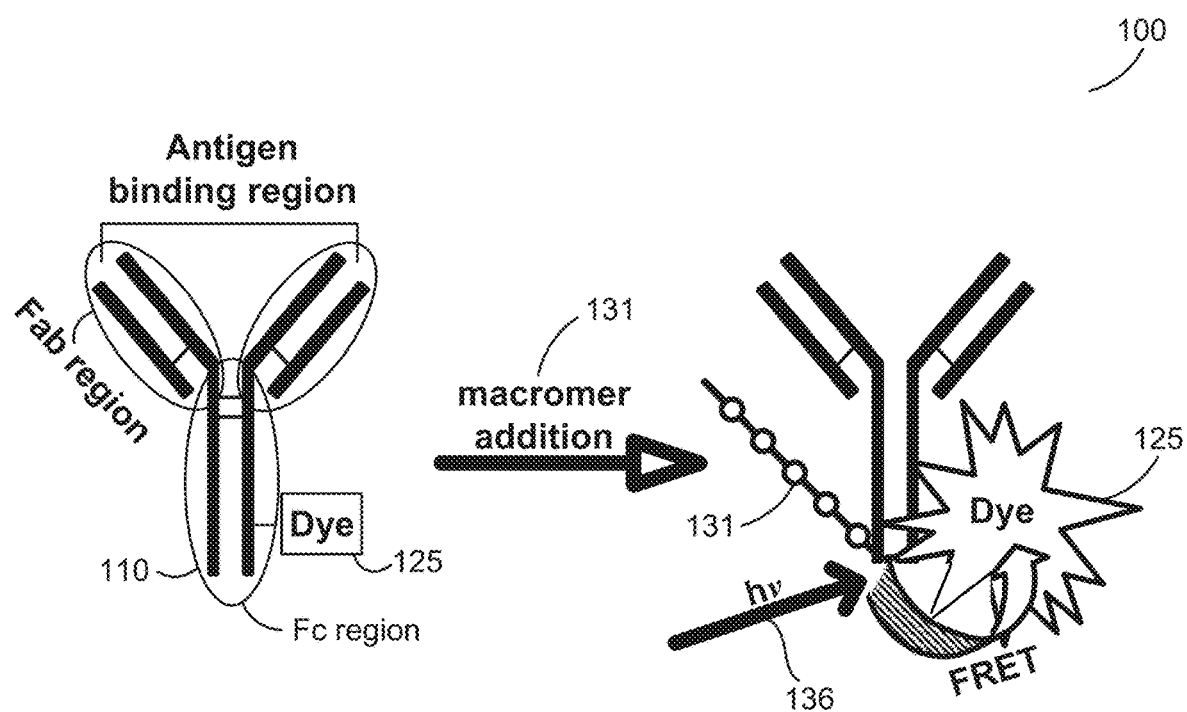
FIG. 1 illustrates an embodiment of the disclosure where an antibody labeled with a dye is reacted with a macromere of this disclosure.

The terms "a," "an," or "the" as used herein not only includes aspects with one member, but also includes aspects with more than one member.

The term "about" as used herein to modify a numerical value indicates a defined range around that value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

When the modifier "about" is applied to describe the beginning of a numerical range, it applies to both ends of the range. Thus, "from about 500 to 850 nm" is equivalent to "from about 500 nm to about 850 nm." When "about" is applied to describe the first value of a set of values, it applies to all values in that set. Thus, "about 580, 700, or 850 nm" is equivalent to "about 580 nm, about 700 nm, or about 850 nm." However, when the modifier "about" is applied to describe only the end of the range or only a later value in the set of values, it applies only to that value or that end of the range. Thus, the range "about 2 to about 10" is the same as "about 2 to about 10," but the range "2 to about 10" is not.

"Activated acyl" as used herein includes a —C(O)-LG group. "Leaving group" or "LG" is a group that is susceptible to displacement by a nucleophilic acyl substitution (i.e., a nucleophilic addition to the carbonyl of —C(O)-LG, followed by elimination of the leaving group). Representative leaving groups include halo, cyano, azido, carboxylic acid derivatives such as t-butylcarboxy, and carbonate derivatives such as i-BuOC(O)O—. An activated acyl group may also be an activated ester as defined herein or a carboxylic acid activated by a carbodiimide to form an anhydride (preferentially cyclic) or mixed anhydride —OC(O)$R^a$ or —OC(N$R^a$)NH$R^b$ (preferably cyclic), wherein $R^a$ and $R^b$ are members independently selected from the group consisting of $C_1$-$C_6$ alkyl, $C_1$-$C_6$ perfluoroalkyl, $C_1$-$C_6$ alkoxy, cyclohexyl, 3-dimethylaminopropyl, or N-morpholinoethyl. Preferred activated acyl groups include activated esters.

"Activated ester" as used herein includes a derivative of a carboxyl group that is more susceptible to displacement by nucleophilic addition and elimination than an ethyl ester group (e.g., an NHS ester, a sulfo-NHS ester, a PAM ester, or a halophenyl ester). Representative carbonyl substituents of activated esters include succinimidyloxy (—$OC_4H_4NO_2$), sulfosuccinimidyloxy (—$OC_4H_3NO_2SO_3H$), -1-oxybenzotriazolyl (—$CO_6H_4N_3$); 4-sulfo-2,3,5,6-tetrafluorophenyl; or an aryloxy group that is optionally substituted one or more times by electron-withdrawing substituents such as nitro, fluoro, chloro, cyano, trifluoromethyl, or combinations thereof (e.g., pentafluorophenyloxy, 2,3,5,6-tetrfluorophenyloxy). Preferred activated esters include succinimidyloxy, sulfosuccinimidyloxy, and 2,3,5,6-tetrfluorophenyloxy esters.

"Acyl" as used herein includes an alkanoyl, aroyl, heterocycloyl, or heteroaroyl group as defined herein. Representative acyl groups include acetyl, benzoyl, nicotinoyl, and the like.

"Alkanoyl" as used herein includes an alkyl-C(O)— group wherein the alkyl group is as defined herein. Representative alkanoyl groups include acetyl, ethanoyl, and the like.

"Alkenyl" as used herein includes a straight or branched aliphatic hydrocarbon group of 2 to about 15 carbon atoms that contains at least one carbon-carbon double or triple bond. Preferred alkenyl groups have 2 to about 12 carbon atoms. More preferred alkenyl groups contain 2 to about 6 carbon atoms. In one aspect, hydrocarbon groups that contain a carbon-carbon double bond are preferred. In a second aspect, hydrocarbon groups that contain a carbon-carbon triple bond are preferred (i.e., alkynyl). "Lower alkenyl" as used herein includes alkenyl of 2 to about 6 carbon atoms. Representative alkenyl groups include vinyl, allyl, n-butenyl, 2-butenyl, 3-methylbutenyl, n-pentenyl, heptenyl, octenyl, decenyl, propynyl, 2-butynyl, 3-methylbutynyl, n-pentynyl, heptynyl, and the like.

An alkenyl group can be unsubstituted or optionally substituted. When optionally substituted, one or more hydrogen atoms of the alkenyl group (e.g., from 1 to 4, from 1 to 2, or 1) may be replaced with a moiety independently selected from the group of fluoro, hydroxy, alkoxy, amino, alkylamino, acylamino, thio, and alkylthio.

"Alkenylene" as used herein includes a straight or branched bivalent hydrocarbon chain containing at least one carbon-carbon double or triple bond. Preferred alkenylene groups include from 2 to about 12 carbons in the chain, and more preferred alkenylene groups include from 2 to 6 carbons in the chain. In one aspect, hydrocarbon groups that contain a carbon-carbon double bond are preferred. In a second aspect, hydrocarbon groups that contain a carbon-carbon triple bond are preferred. Representative alkenylene groups include —CH═CH—, —$CH_2$—CH═CH—, —C($CH_3$)═CH—, —$CH_2$CH═CH$CH_2$—, ethynylene, propynylene, n-butynylene, and the like.

"Alkoxy" as used herein includes an alkyl-O— group wherein the alkyl group is as defined herein. Representative alkoxy groups include methoxy, ethoxy, n-propoxy, i-propoxy, n-butoxy, heptoxy, and the like.

An alkoxy group can be unsubstituted or optionally substituted. When optionally substituted, one or more hydrogen atoms of the alkoxy group (e.g., from 1 to 4, from 1 to 2, or 1) may be replaced with a moiety independently selected from the group of fluoro, hydroxy, alkoxy, amino, alkylamino, acylamino, thio, and alkylthio.

"Alkoxyalkyl" as used herein includes an alkyl-O-alkylene- group wherein alkyl and alkylene are as defined herein. Representative alkoxyalkyl groups include methoxyethyl, ethoxymethyl, n-butoxymethyl and cyclopentylmethyloxyethyl.

"Alkoxycarbonyl" as used herein includes an ester group; i.e., an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" as used herein includes an alkyl-O—CO-alkylene- group wherein alkyl and alkylene are as defined herein. Representative alkoxycarbonylalkyl include methoxycarbonylmethyl, ethoxycarbonylmethyl, methoxycarbonylethyl, and the like.

"Alkyl" as used herein includes an aliphatic hydrocarbon group, which may be straight or branched-chain, having about 1 to about 20 carbon atoms in the chain Preferred alkyl groups have 1 to about 12 carbon atoms in the chain. More preferred alkyl groups have 1 to 6 carbon atoms in the chain. "Branched-chain" as used herein includes that one or more lower alkyl groups such as methyl, ethyl or propyl are attached to a linear alkyl chain.

"Lower alkyl" as used herein includes 1 to about 6 carbon atoms, preferably 5 or 6 carbon atoms in the chain, which may be straight or branched. Representative alkyl groups include methyl, ethyl, n-propyl, isopropyl, n-butyl, t-butyl, n-pentyl, and 3-pentyl.

An alkyl group can be unsubstituted or optionally substituted. When optionally substituted, one or more hydrogen atoms of the alkyl group (e.g., from 1 to 4, from 1 to 2, or 1) may be replaced with a moiety independently selected from the group of fluoro, hydroxy, alkoxy, amino, alkylamino, acylamino, thio, and alkylthio.

"Alkylene" as used herein includes a straight or branched bivalent hydrocarbon chain of 1 to about 6 carbon atoms. Preferred alkylene groups are the lower alkylene groups having 1 to about 4 carbon atoms. Representative alkylene groups include methylene, ethylene, and the like.

"Alkylthio" as used herein includes an alkyl-S— group wherein the alkyl group is as defined herein. Preferred alkylthio groups are those wherein the alkyl group is lower alkyl. Representative alkylthio groups include methylthio, ethylthio, isopropylthio, heptylthio, and the like.

"Alkylthioalkyl" as used herein includes an alkylthio-alkylene- group wherein alkylthio and alkylene are defined herein. Representative alkylthioalkyl groups include methylthiomethyl, ethylthiopropyl, isopropylthioethyl, and the like.

"Amido" as used herein includes a group of formula $Y_1Y_2N$—C(O)— wherein $Y_1$ and $Y_2$ are independently hydrogen, alkyl, or alkenyl; or $Y_1$ and $Y_2$, together with the nitrogen through which $Y_1$ and $Y_2$ are linked, join to form a 4- to 7-membered azaheterocyclyl group (e.g., piperidinyl). Representative amido groups include primary amido ($H_2N$—C(O)—), methylamido, dimethylamido, diethylamido, and the like. Preferably, "amido" is an —C(O)NRR' group where R and R' are members independently selected from the group of H and alkyl. More preferably, at least one of R and R' is H.

"Amidoalkyl" as used herein includes an amido-alkylene- group wherein amido and alkylene are defined herein. Representative amidoalkyl groups include amidomethyl, amidoethylene, dimethylamidomethyl, and the like.

"Amino" as used herein includes a group of formula $Y_1Y_2N$— wherein $Y_1$ and $Y_2$ are independently hydrogen, acyl, or alkyl; or $Y_1$ and $Y_2$, together with the nitrogen through which $Y_1$ and $Y_2$ are linked, join to form a 4- to 7-membered azaheterocyclyl group (e.g., piperidinyl). Optionally, when $Y_1$ and $Y_2$ are independently hydrogen or alkyl, an additional substituent can be added to the nitrogen, making a quaternary ammonium ion. Representative amino groups include primary amino ($H_2N$—), methylamino, dimethylamino, diethylamino, and the like. Preferably, "amino" is an —NRR' group where R and R' are members independently selected from the group of H and alkyl. Preferably, at least one of R and R' is H.

"Aminoalkyl" as used herein includes an amino-alkylene- group wherein amino and alkylene are defined herein. Representative aminoalkyl groups include aminomethyl, aminoethyl, dimethylaminomethyl, and the like.

"Aroyl" as used herein includes an aryl-CO— group wherein aryl is defined herein. Representative aroyl include benzoyl, naphth-1-oyl and naphth-2-oyl.

"Aryl" as used herein includes an aromatic monocyclic or multicyclic ring system of 6 to about 14 carbon atoms, preferably of 6 to about 10 carbon atoms. Representative aryl groups include phenyl and naphthyl.

"Aromatic ring" as used herein includes 5-12 membered aromatic monocyclic or fused polycyclic moieties that may include from zero to four heteroatoms selected from the group of oxygen, sulfur, selenium, and nitrogen. Exemplary aromatic rings include benzene, pyrrole, furan, thiophene, imidazole, oxazole, thiazole, triazole, pyrazole, pyridine, pyrazine, pyridazine, pyrimidine, naphthalene, benzathiazoline, benzothiophene, benzofurans, indole, benzindole, quinoline, and the like. The aromatic ring group can be substituted at one or more positions with halo, alkyl, alkoxy, alkoxy carbonyl, haloalkyl, cyano, sulfonato, amino sulfonyl, aryl, sulfonyl, aminocarbonyl, carboxy, acylamino, alkyl sulfonyl, amino and substituted or unsubstituted substituents.

"Biomolecule" as used herein includes a natural or synthetic molecule for use in biological systems. Preferred biomolecules include an antibody, an antigen, a protein, a peptide, an enzyme substrate, a hormone, a hapten, an avidin, a streptavidin, a carbohydrate, a carbohydrate derivative, an oligosaccharide, a polysaccharide, and a nucleic acid. More preferred biomolecules include an antibody, a protein, a peptide, an avidin, a streptavidin, or biotin. In certain aspects, biomolecules include, but are not limited to, proteins, peptides, affinity ligands, antibodies, antibody fragments, sugars, lipids, enzymes and nucleic acids (as hybridization probes and/or aptamers).

"Carboxy" and "carboxyl" as used herein include a HOC(O)— group (i.e., a carboxylic acid) or a salt thereof.

"Carboxyalkyl" as used herein includes a HOC(O)-alkylene- group wherein alkylene is defined herein. Representative carboxyalkyls include carboxymethyl (i.e., HOC(O)$CH_2$—) and carboxyethyl (i.e., HOC(O)$CH_2CH_2$—).

A "conjugated macromer" as used herein includes a macromer that contains an extended series of unsaturated bonds. The backbone of the conjugated macromer or polymer can contain alternating double and single bonds. A conjugated polymer can be conjugated along the full length of its backbone or can contain conjugated segments together with non-conjugated segments.

"Conjugated" as used herein includes an unsaturated organic system having adjacent atoms with pi electrons where there is overlap of a p-orbital with another across an intervening sigma bond. In larger atoms d-orbitals can be involved. The atoms can be $sp^2$ or sp hybridized carbon atoms or other atoms with unshared electron pairs which can be hybridized into p orbitals.

"Cycloalkyl" as used herein includes a non-aromatic mono- or multicyclic ring system of about 3 to about 10 carbon atoms, preferably of about 5 to about 10 carbon atoms. More preferred cycloalkyl rings contain 5 or 6 ring atoms. A cycloalkyl group optionally comprises at least one $sp^2$-hybridized carbon (e.g., a ring incorporating an endocyclic or exocyclic olefin). Representative monocyclic cycloalkyl groups include cyclopentyl, cyclohexyl, cyclohexenyl, cycloheptyl, and the like. Representative multicyclic cycloalkyl include 1-decalin, norbornyl, adamantyl, and the like.

"Cycloalkylene" as used herein includes a bivalent cycloalkyl having about 4 to about 8 carbon atoms. Preferred cycloalkylenyl groups include 1,2-, 1,3-, or 1,4-cis- or trans-cyclohexylene.

"Halo" or "halogen" as used herein includes fluoro, chloro, bromo, or iodo.

"Heteroatom" as used herein includes an atom other than carbon or hydrogen. Representative heteroatoms include O, S, and N. The nitrogen or sulphur atom of the heteroatom is optionally oxidized to the corresponding N-oxide, S-oxide (sulfoxide), or S,S-dioxide (sulfone). In a preferred aspect, a heteroatom has at least two bonds to alkylene carbon atoms (e.g., —$C_1$-$C_9$ alkylene-O—$C_1$-$C_9$ alkylene-). In some embodiments, a heteroatom is further substituted with an acyl, alkyl, aryl, cycloalkyl, heterocyclyl, or heteroaryl group (e.g., —N(Me)-; —N(Ac)—).

"Heteroaryl" as used herein refers to an aryl group in which at least one carbon atom in at least one aromatic ring is replaced by a heteroatom (e.g., nitrogen, oxygen, sulfur, and phosphorus), such that the aromaticity of the compound is retained, and can be optionally substituted at one or more substitutable positions. Exemplary heteroaryl groups include furanyl, thienyl, pyridyl, pyridazinyl, pyrrolyl, N-lower alkyl-pyrrolo, pyrimidyl, pyrazinyl, triazinyl, tetrazinyl, triazolyl, tetrazolyl, imidazolyl, bipyridyl, tripyridyl, tetrapyridyl, phenazinyl, phenanthrolinyl, purinyl, perylene, perylene diimide, kidetopyrrolopyrrole, benzothiodiazol, benzoxadiazol, thienopyrazine and the like. Additional examples of heteroaryl groups include fused ring systems, such as, for example, benzofuryl, benzothienyl, benzopyrrolyl, dibenzofuryl, dibenzothienyl, phenanthrolinyl, carbazolyl and azacarbazolyl groups.

"Heteroaroyl" as used herein includes a heteroaryl-C(O)— group wherein heteroaryl is as defined herein. Representative heteroaroyl groups include thiophenoyl, nicotinoyl, pyrrol-2-ylcarbonyl, pyridinoyl, and the like.

"Heterocycloyl" as used herein includes a heterocyclyl-C(O)— group wherein heterocyclyl is as defined herein. Representative heterocycloyl groups include N-methyl prolinoyl, tetrahydrofuranoyl, and the like.

"Hydroxyalkyl" as used herein includes an alkyl group as defined herein substituted with one or more hydroxy groups. Preferred hydroxyalkyls contain lower alkyl. Representative hydroxyalkyl groups include hydroxymethyl and 2-hydroxyethyl.

The term "optionally substituted" means that the substituent may be substituted or unsubstituted. For example, a hydrogen atom of an alkyl group (e.g., from 1 to 4, from 1 to 2, or 1) may be replaced with a moiety independently selected from the group of fluoro, hydroxy, alkoxy, amino, alkylamino, acylamino, thio, and alkylthio. An aromatic ring group can be substituted at one or more positions with halo, alkyl, alkoxy, alkoxy carbonyl, haloalkyl, cyano, sulfonato, amino sulfonyl, aryl, sulfonyl, aminocarbonyl, carboxy, acylamino, alkyl sulfonyl, amino and substituted or unsubstituted substituents. In an analogous fashion, each of the substituent groups referred to herein can be analogously substituted, with amino, halo, hydroxy, alkoxy, cyano, nitro, alkylamino, acylamino, thio, alkylthio, alkyl, alkoxy carbonyl, haloalkyl, sulfonato, aminosulfonyl, aryl, sulfonyl, aminocarbonyl, carboxy, acylamino, and alkylsulfonyl.

"The number average molecular weight" includes the arithmetic mean or average of the molecular masses of the individual macromolecules. It is determined by measuring the molecular mass of n polymer molecules, summing the masses, and dividing by n. On the other hand, weight average molecular weight ($M_w$) takes into account the molecular weight of a chain in determining contributions to the molecular weight average. The more massive the chain, the more the chain contributes to $M_w$. $M_w$ is determined by methods that are sensitive to the molecular size rather than just their number, such as light scattering techniques.

"Water-soluble" as used herein includes a material that is soluble in an aqueous-based solution, such as in water, water-based solutions or buffer solutions, including those used in biological or molecular detection systems. A "water-soluble" solution refers to a homogeneous solution containing fully dissolved material. A "water-soluble" macromer of this disclosure is soluble in an aqueous-based solution at a concentration of >0.10 mg/mL. Incorporation of at least one "water-solubilizing group" into the material can increase the hydrophilicity of the material and can improve the solubility or dispersibility of the material in an aqueous environment.

A. Compounds

The present disclosure provides polyindenofluorene macromers, methods for preparing the macromers as well as methods of using the macromers. In certain aspects, the macromers of formula I or formula II include one or more water-solubilizing groups. Water-soluble, conjugated macromers including one or more water-solubilizing groups render the polyindenofluorene macromers soluble in aqueous medium (e.g., water or buffers). The macromers are suitable for use for use in various types of biological applications. The macromers emit bright, visible light upon UV excitation (e.g., resulting from irradiation with a violet laser) and can exhibit high extinction coefficients and quantum efficiency (e.g., quantum yield >50%).

As such, in one embodiment, the present disclosure provides a macromer of formula I or formula II:

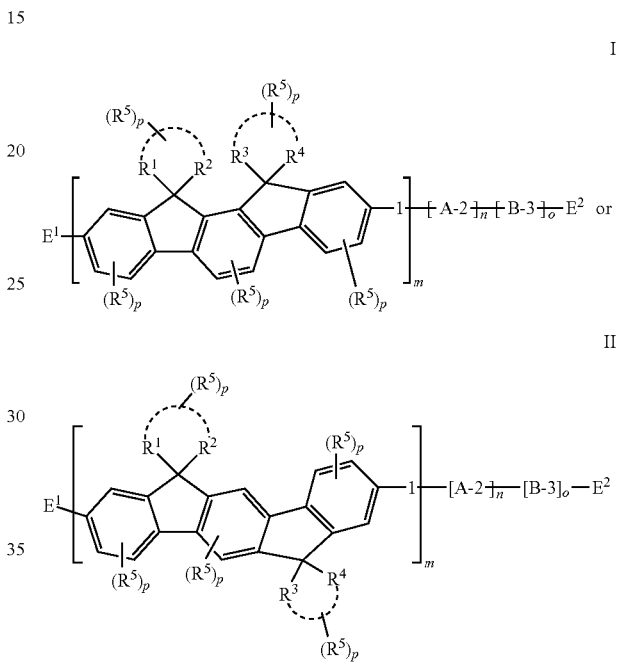

In certain aspects, the macromers of formula I and formula II can be combined in an alternating, a block, a random or a graph copolymer configuration between $E^1$ and $E^2$. Advantageously, the various connection patterns and the identity and content of the $2^{nd}$ and $3^{rd}$ monomer(s) result in different conjugation structures having structural polymer differences as well as differences in spectral properties such as absorption, emission, and quantum yield. The various copolymer configurations are schematically shown in scheme I below. In this illustrative scheme, segment A in scheme I below may represent segment "m" and segment B in scheme I may represents segment "n" in formula I or II as follows:

Scheme I.

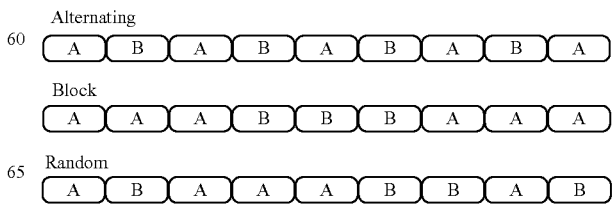

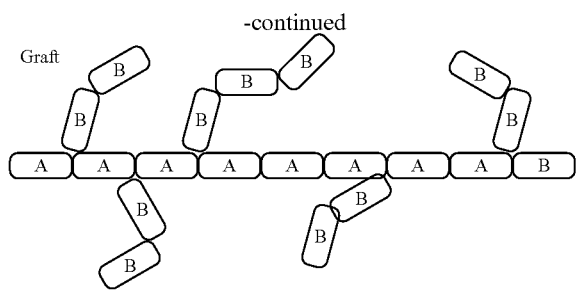
Graft

Although a segment representing segment "o" is not shown, a skilled person would immediately realize segment o from formula I or II can be incorporated into a copolymer configuration as depicted in scheme I.

The term "copolymer" is a term known in the art. It includes a polymer comprising two or more different monomer units such as segments m, n and o (depicted as e.g., A, B, C) that are polymerized in a process called copolymerization. Since a copolymer comprises at least two different monomeric units, copolymers can be classified based on how the monomers are arranged to form a polymer chain. Those classifications include "alternating copolymers" (in which the monomers units repeat with an regular alternating pattern such as A-B-A-B-A-B or A-B-C-A-B-C), "block copolymers" (in which two or more homopolymer subunits are linked such as A-A-A-B-B-B or A-A-A-B-B-B-C-C-C), "random copolymers" (in which the monomer units are attached in a random order such as A-B-A-A-A-B-B-A-B or A-B-A-A-A-B-B-A-B-CCC-A-B), and "graph copolymers" (in which a homopolymer is graphed to a second polymer such as B-B-B is graphed to A-A-A-A or C-C-C is graphed to A-A-A-A-B-B-B). The copolymers of this disclosure can be an alternating copolymer, block copolymers, random copolymers or graph copolymers between $E^1$ and $E^2$. In certain instances, the copolymer is an alternating copolymer. In certain instances, the copolymer is a random copolymer.

In formula I or formula II, each of $R^2$, $R^3$ and $R^4$ are each independently a member selected from the group of hydrogen, an optionally substituted $C_1$-$C_{10}$ alkyl, an optionally substituted $C_1$-$C_{18}$ alkoxy, optionally substituted $C_6$-$C_{18}$ aryl, optionally substituted $C_4$-$C_{18}$ acyl, optionally substituted $C_4$-$C_{18}$ acyloxy, $NR^aR^b$, wherein $R^a$ and $R^b$ are each independently hydrogen or lower alkyl, a water soluble group, ethylene oxide oligomers or an ethylene oxide oligomer methyl ether. The dotted circle means that a ring is an alternative embodiment.

In an alternative embodiments, $R^1$ and $R^2$ and/or $R^3$ and $R^4$ together with the carbons to which they are attached, join to form a an optionally substituted 4-, 5-, or 6-membered ring. In certain aspects, both $R^1$ and $R^2$ as well as $R^3$ and $R^4$ join to form an optionally substituted 4-, 5, or 6-membered ring. In other aspects, only $R^1$ and $R^2$ join to form a an optionally substituted 4-, 5, or 6-membered ring. In other aspects, only $R^3$ and $R^4$ join to form a an optionally substituted 4-, 5, or 6-membered ring.

In certain aspects, the optionally substituted 4-, 5-, or 6-membered ring is selected from the group of optionally substituted $C_4$-$C_6$ cycloalkyl group and an optionally substituted $C_4$-$C_6$ heterocyclyl group. For example, $R^1$ and $R^2$ and/or $R^3$ and $R^4$ form an optionally substituted $C_4$-cycloalkyl, a $C_5$-cycloalkyl or a $C_6$-cycloalkyl group. In one aspect, $R^1$ and $R^2$ and/or $R^3$ and $R^4$ form an optionally substituted 4-, 5-, or 6-membered ring, which generates a bicyclic ring system (within the larger ring system), where the two rings are connected through a single common atom. This common atom joining the bicyclic rings is generally referred to as a "spiro" atom.

In formula I or formula II, each $R^5$ is independently a member selected from the group of halo, alkyl, alkoxy, amino, a water-solubilizing group, ethylene oxide oligomers and an ethylene oxide oligomer methyl ether.

In certain instances, $R^5$ is an ethylene oxide oligomer such as a —$(CH_2)_y$—$(OCH_2CH_2)_xOCH_3$ group, wherein y is a value from 1-20 and x is a value from 1-50. For example, the value of y can be 1, 2, 3, 4, 5, 6, 7, 8, 9, 10, 11, 12, 13, 14, 15, 16, 17, 18, 19, or 20. The value of x can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. The ethylene oxide oligomers enhance the water solubility of the macromer.

In certain aspects, the $C_4$-$C_6$ heterocyclyl group is a member selected from the group consisting of an azetidinyl, oxetanyl, thietanyl, a pyrrolidinyl, an oxolanyl, a thiolanyl, a piperidinyl, an oxanyl and a thianyl or an optionally substituted tetrahydropyranyl such as a xanthenyl. In certain preferred aspects, the $C_4$-$C_6$ heterocyclyl group is an optionally substituted pyrrolidinyl group or a piperidinyl group.

In certain aspects, the $C_4$-$C_6$ heterocyclyl group is substituted with $R^5$. $R^5$ can be at least one ethylene oxide oligomer such as a —$(CH_2)_y$—$(OCH_2CH_2)_xOCH_3$ group, wherein y is value from 1-20 and x is a value from 1-50.

In one aspect, the optionally substituted 4-, 5, or 6-membered ring is a $C_4$-$C_6$ heterocyclyl group is a member selected from the group consisting of an azetidinyl, oxetanyl, thietanyl, a pyrrolidinyl, an oxolanyl, a thiolanyl, a piperidinyl, an oxanyl and a thianyl or an optionally substituted tetrahydropyranyl such as a xanthenyl. In certain preferred aspects, the $C_4$-$C_6$ heterocyclyl group is an optionally substituted pyrrolidinyl group or a piperidinyl group.

In formula I or formula II, each p is a value from 0-3, such as 0, 1, 2, or 3.

In formula I or formula II, m is a value selected from the group consisting of 1-10,000. In certain aspects, the value of m is 1-10,000 such as 1 to 10, 1 to 20, 1 to 30, 1 to 40, 1 to 50, 1 to 60, 1 to 70, 1 to 80, 1 to 90, 1 to 100, 1 to 200, 1 to 300, 1 to 400, 1 to 500, 1 to 600, 1 to 700, 1 to 800, 1 to 900, 1 to 1000, 1 to 1 to 2000, 1 to 3000, 1 to 4000, 1 to 5000, 1 to 6000, 1 to 7000, 1 to 8000, 1 to 9000 or 1 to 10000.

Within formula I or formula II, n and o are each independently a value selected from the group consisting of 0-10,000, wherein the monomers within m, n, and o may be the same or different. In certain aspects, the values of n and o are each independently a value selected from the group consisting of 0-10,000, such as 0, 1, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000 or 10000. When n is 0, segment A-2 is absent. When o is 0, segment B-3 is absent. As such, each of A-2 and B-3, can be present or absent and can each be the same or different, and each is selected from the group consisting of an aromatic group or heteroaromatic group, which group completes a π-conjugated backbone.

In certain aspects in formula I and formula II, m is 1-50, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50.

In certain aspects in formula I and formula II, n is 0-50, such as about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50.

In certain aspects in formula I and formula II, o is 0-50, such as about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50.

In certain instances, the polyindenofluorene, macromers of formula I or formula II comprise at least one monomer residue substituted with one or more water-solubilizing groups. In certain instances, the backbone of the polyindenofluorene macromers of formula I or II include a plurality of monomer residues. The macromer backbone can include a conjugated segment. The polymer backbone can further include at least one monomer residue that comprises an optionally substituted aromatic or heteroaromatic group appended to the indenofluorene monomer, which is A and/or B.

In certain aspects, each of A and B in formula I or formula II may be present or absent. If present, A, and B can be the same or different. A and B represent a divalent substituent, which is a divalent group selected from the group of benzene, naphthalene, anthracene, benzodiathiazolyl, fluorene, indenofluorene, thiophene, thienothiophene, dithienothiophene, 3,4-ethylenedioxythiophene, furan, pyridine, pyrrole, fused pyrrole, tetrahydropyrene, quinoxaline benzothiadiazole, thieno[3,4-b]-pyrazine and oxadiazole. Each of the foregoing groups may be optionally substituted.

For the copolymer aspects, these polymers may be alternate, block, and random copolymers or their combination. The fluorescence performances such as molar extinction coefficient, fluorescence quantum yield, absorption and emission maxima and shape are expected to be different.

In certain aspects, segments m, n and o may also have a moiety 1, 2 and/or 3 present, which is a divalent aryl or heteroaryl group. Each of 1, 2 or 3 may be present or absent. Moieties 1, 2 and 3 are each independently selected from the group of benzene, naphthalene, anthracene, benzodiathiazolyl, fluorene, indenofluorene, thiophene, thienothiophene, dithienothiophene, 3,4-ethylenedioxythiophene, furan, pyridine, pyrrole, fused pyrrole, tetrahydropyrene and oxadiazole. Each of the foregoing groups may be optionally substituted.

In formula I and formula II, $E^1$ and $E^2$ are each independently a member selected from the group of hydrogen, halogen, alkynyl, optionally substituted aryl, optionally substituted heteroaryl, halo, substituted aryl, boronic acid substituted aryl, boronic ester substituted aryl, boronic ester, boronic acid, optionally substituted fluorene and aryl or heteroaryl substituted with one or more pendant chains terminated with: i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule.

In one aspect, $E^1$ and $E^2$ are each independently a member selected from the group consisting of hydrogen and a functional moiety which is a member selected from the group of an amine, a carbamate, a carboxylic acid, a carboxylate, a maleimide, an activated ester, N-hydroxysuccinimidyl, a hydrazine, a hydrazid, a hydrazone, an azide, an alkyne, an aldehyde, a thiol, an alkyl halide and protected groups thereof for conjugation to a molecule or biomolecule.

Biomolecules include, but are not limited to, an antibody, an antigen, a protein, a peptide, an enzyme substrate, a hormone, a hapten, an avidin, a streptavidin, a carbohydrate, a carbohydrate derivative, an oligosaccharide, a polysaccharide, and a nucleic acid. More preferred biomolecules include an antibody, a protein, a peptide, an avidin, a streptavidin, or biotin. In certain aspects, biomolecules include, but are not limited to, proteins, peptides, affinity ligands, antibodies, antibody fragments, sugars, lipids, enzymes and nucleic acids (as hybridization probes and/or aptamers).

The compounds of formula I and formula II can react with a biomolecule using conjugation chemistry well known in the art. For example, an activated ester (an NHS ester) can react with a primary amine to make a stable amide bond. A maleimide and a thiol can react together and make a thioether. Alkyl halides react with amines and thiols to make alkylamines and thioethers, respectively. Any derivative providing a reactive moiety that can be conjugated to a protein or biomolecule can be utilized herein.

In one embodiment, 1, 2, and 3 are each absent in formula I and formula II, which provides formula I-a and formula II-a:

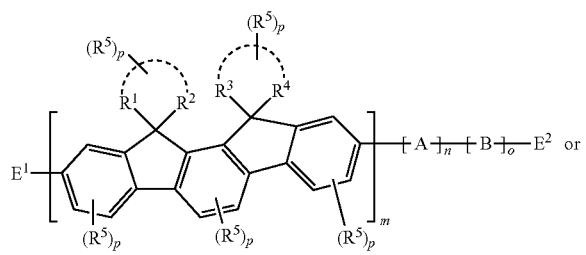

I-a

II-a

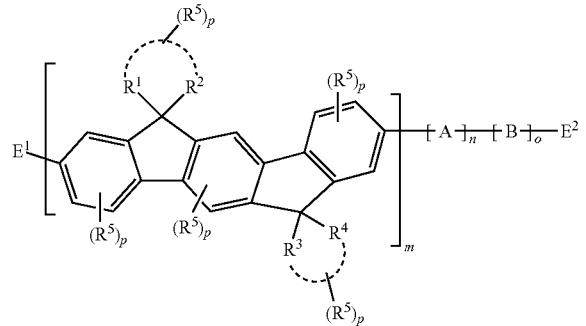

In one aspect, A and B are absent (n=0 and o=0) and the compound has the structure:

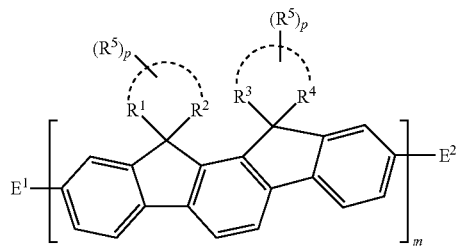

wherein the dotted lines mean that both $R^1$ and $R^2$ as well as $R^3$ and $R^4$ can alternatively join to form a an optionally substituted 4-, 5-, or 6-membered ring, or that only $R^1$ and $R^2$ join to form a an optionally substituted 4-, 5, or 6-membered ring, or that only $R^3$ and $R^4$ join to form a an optionally substituted 4-, 5, or 6-membered ring. The optionally substituted 4-, 5-, or 6-membered ring is selected from the group of optionally substituted $C_4$-$C_6$ cycloalkyl group and an optionally substituted $C_4$-$C_6$ heterocyclyl group. Both optionally substituted 4-, 5, or 6-membered rings may be absent.

In formula I or II, a water-solubilizing group is a group that imparts more hydrophilicity to the macromer. A water-solubilizing group can be an ethylene oxide oligomer or an ethylene oxide polymer or an ethylene oxide oligomer methyl ether. In certain aspects, water-solubilizing groups include one or more alkylene oxide repeat units. For example, a water-solubilizing group can contain one or more ethylene glycol units, —($OCH_2CH_2$)—. Ethylene glycol oligomers or polymers are referred to herein as a "polyethylene glycol" (PEG) group. The PEG group can be any length, however, typically ranges between 1 to 5000 ethylene glycol repeat units. In certain embodiments, PEG groups having more than 20 ethylene glycol repeat units are used. In certain aspects, the ethylene oxide units can be between 11 to about 550, inclusive. The PEG chain can be appended to the monomer, grafted, or coupled to the polymer in order to increase water solubility.

In certain aspects, $PEG_{550}$-$OCH_3$ has the formula of $CH_3$—(O—$CH_2$—$CH_2$)$_x$— with a number average molecular weight of 550 and a terminal methoxy group. Polyethylene glycol monomethyl ether, "mPEG" has the linear formula $CH_3(OCH_2CH_2)_nOH$ with an average $M_n$ of 550. Other averages include, but are not limited to, 350, 750, 2000 and 5000 or the number of units can be between 11-550, inclusive.

In certain aspects, the compound of formula I-a has the formula selected from the group:

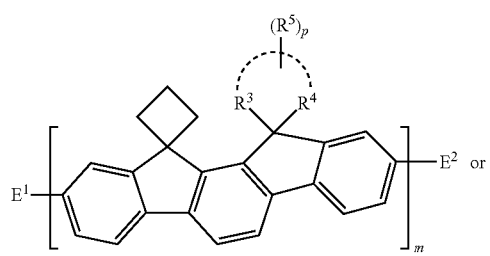

or

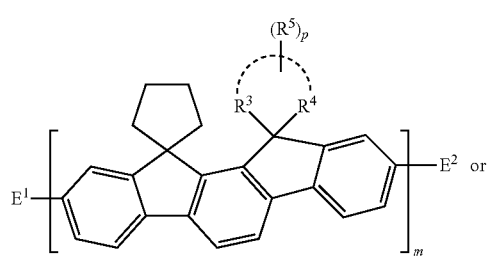

or

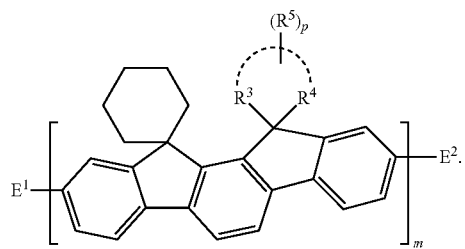

In certain aspects, the compound of formula I-a has the formula:

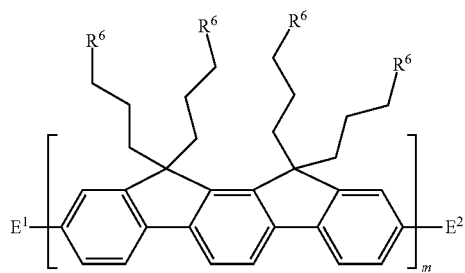

In certain aspects, $R^6$ is a water soluble group, such as an ethylene oxide oligomer methyl ether. In certain aspects, the ethylene oxide oligomer methyl ether is between —O-$PEG_{11}$-$OCH_3$ and —O-$PEG_{550}$-$OCH_3$ inclusive, such as —O-$PEG_{11}$-$OCH_3$ and —O-$PEG_{550}$-$OCH_3$. In one aspect, $R^6$ is —O-$PEG_{11}$-$OCH_3$. In another aspect, $R^6$ is —O-$PEG_{550}$-$OCH_3$.

In certain aspects, the compound of formula II-a has the formula:

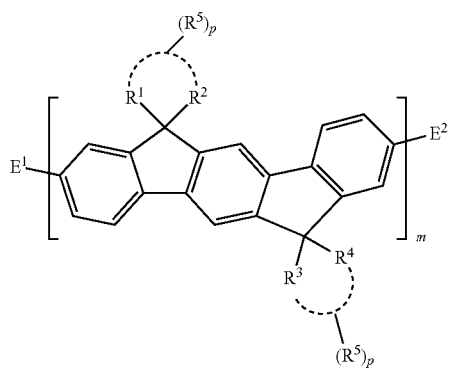

wherein the dotted lines mean that both $R^1$ and $R^2$ as well as $R^3$ and $R^4$ may alternatively join to form a an optionally substituted 4-, 5, or 6-membered ring, or that only $R^1$ and $R^2$ join to form a an optionally substituted 4-, 5, or 6-membered ring, or that only $R^3$ and $R^4$ join to form a an optionally substituted 4-, 5, or 6-membered ring. The optionally substituted 4-, 5-, or 6-membered ring is selected from the group of optionally substituted $C_4$-$C_6$ cycloalkyl group and an optionally substituted $C_4$-$C_6$ heterocyclyl group. Both optionally substituted 4-, 5, or 6-membered rings may be absent.

In certain aspects, the compound of formula II-a has the formula selected from the group:

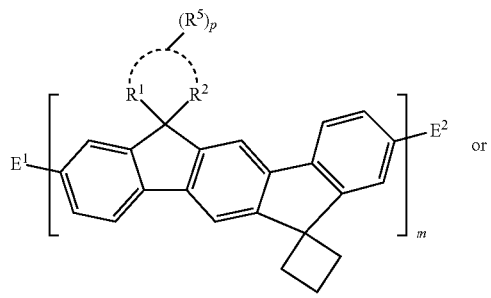

or

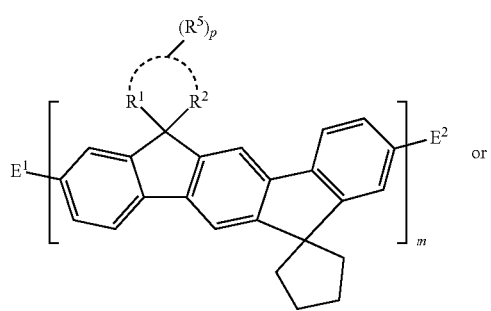

or

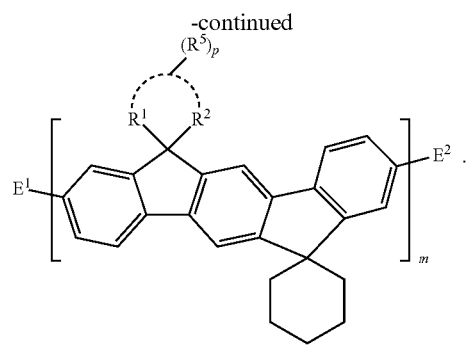

In certain aspects, the compound of formula II-a has the formula:

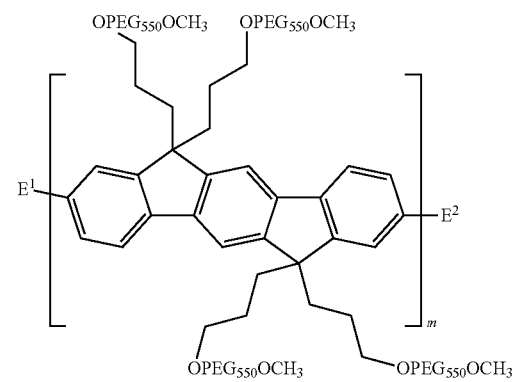

In certain aspects, the compound of formula II has the formula:

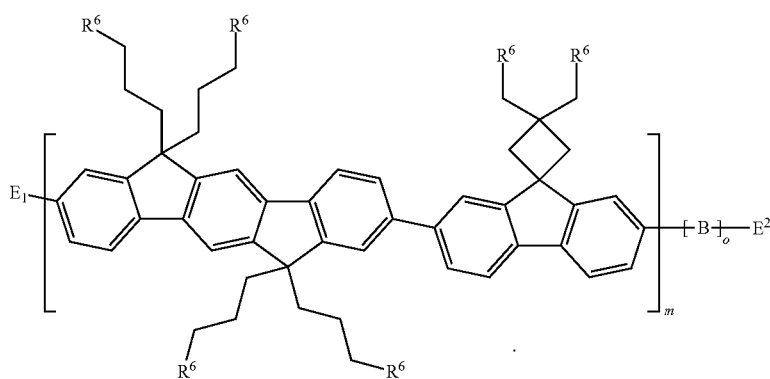

wherein "1" has the structure:

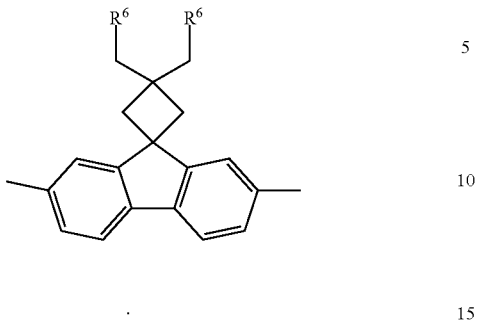

in the above.

In certain aspects, the compound of formula II-a has the formula:

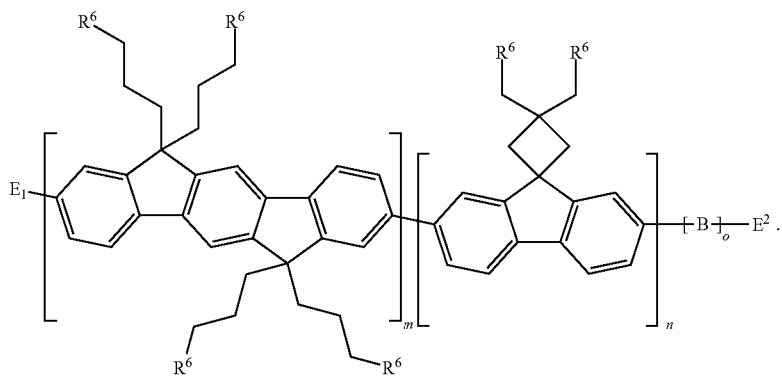

In certain aspects, each $R^6$ is independently a water soluble group, such as an ethylene oxide oligomer methyl ether e.g., $mPEG_{550}$. In certain aspects, the ethylene oxide oligomer methyl ether is between —O-$PEG_{11}$-$OCH_3$ and —O-$PEG_{550}$-$OCH_3$ inclusive, such as —O-$PEG_{11}$-$OCH_3$ and —O-$PEG_{550}$-$OCH_3$. In one aspect, $R^6$ is —O-$PEG_{11}$-$OCH_3$. In another aspect, $R^6$ is —O-$PEG_{550}$-$OCH_3$.

In certain aspects, B represent a divalent substituent, which is a divalent group selected from the group of benzene, naphthalene, anthracene, benzodiathiazolyl, fluorene, indenofluorene, thiophene, thienothiophene, dithienothiophene, 3,4-ethylenedioxythiophene, furan, pyridine, pyrrole, fused pyrrole, tetrahydropyrene and oxadiazole. Each of the foregoing groups may be optionally substituted.

In certain aspects, m is 1-50, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50; n is 1-50, o is 0-50.

In certain aspects, B has the following formula:

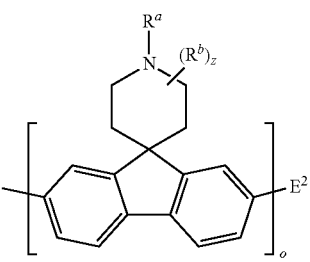

wherein $R^a$ is a member selected from the group of hydrogen, an optionally substituted $C_1$-$C_{18}$ alkyl, an optionally substituted $C_1$-$C_{18}$ alkoxy, optionally substituted $C_6$-$C_{18}$ aryl, optionally substituted $C_4$-$C_{18}$ acyl, optionally substituted $C_4$-$C_{18}$ acyloxy, a water-solubilizing group, ethylene oxide oligomers, ethylene oxide polymer, and a functional group for conjugation to a molecule or biomolecule;

wherein $R^b$ is a member selected from the group of hydrogen, an optionally substituted $C_1$-$C_{18}$ alkyl, an optionally substituted $C_1$-$C_{18}$ alkoxy, an optionally substituted $C_6$-$C_{18}$ aryl, an optionally substituted $C_4$-$C_{18}$ acyl, an optionally substituted $C_4$-$C_{18}$ acyloxy, a water-solubilizing group, ethylene oxide oligomers, ethylene oxide polymer or a site for conjugation; and z is a value of 0 to 4, such as 0, 1, 2, 3, or 4.

In certain aspects, B has the following formula:

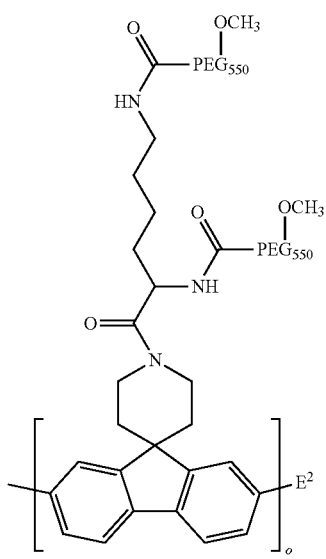

wherein $PEG_{550}$ has the formula of $CH_3$—$(O$—$CH_2$—$CH_2)_x$ with a number average molecular weight of 550 and o is 1-50.

In certain aspects, B has the following formula:

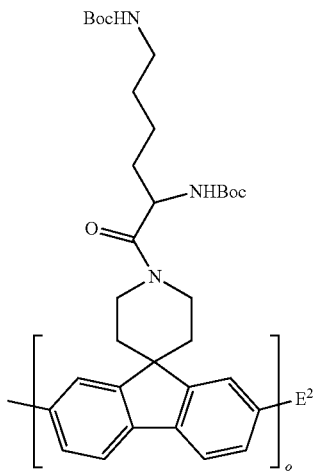

the value of o is 1-15 such as 1, 2, 3, 4, 5, 6, 7, 8, 9, 10, 11, 12, 13, 14 or 15 or 1-30, 1-40, or 1-50. In one aspect, $E^2$ is a N-hydroxysuccinimidyl group. The Boc groups can be removed and a water-solubilizing group, ethylene oxide oligomers and ethylene oxide polymer, or it can be a site for conjugation. An example of a water soluble group is ethylene oxide oligomer such as a —$(CH_2)_y$—$(OCH_2CH_2)_x$$OCH_3$ group, wherein y is a value from 1-20 and x is a value from 1-50. For example, the value of y can be 1, 2, 3, 4, 5, 6, 7, 8, 9, 10, 11, 12, 13, 14, 15, 16, 17, 18, 19, or 20. The value of x can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. A site for conjugation can be i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule. In the above, $R^a$ is a substituted acyl group —C(O)—CH(NH$_2$)—CH$_2$CH$_2$CH$_2$CH$_2$NH$_2$, wherein the amines are Boc protected.

In certain aspects, B has the following formula:

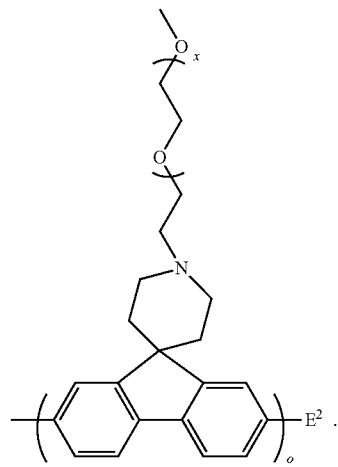

In certain aspects, the value of o is 1-50 or o is 1-15 such as 1, 2, 3, 4, 5, 6, 7, 8, 9, 10, 11, 12, 13, 14 or 15 and the value of x is between 11 and 550. In one aspect, $E^2$ is a N-hydroxysuccinimidyl group.

In certain aspects, the compound of formula II has the formula:
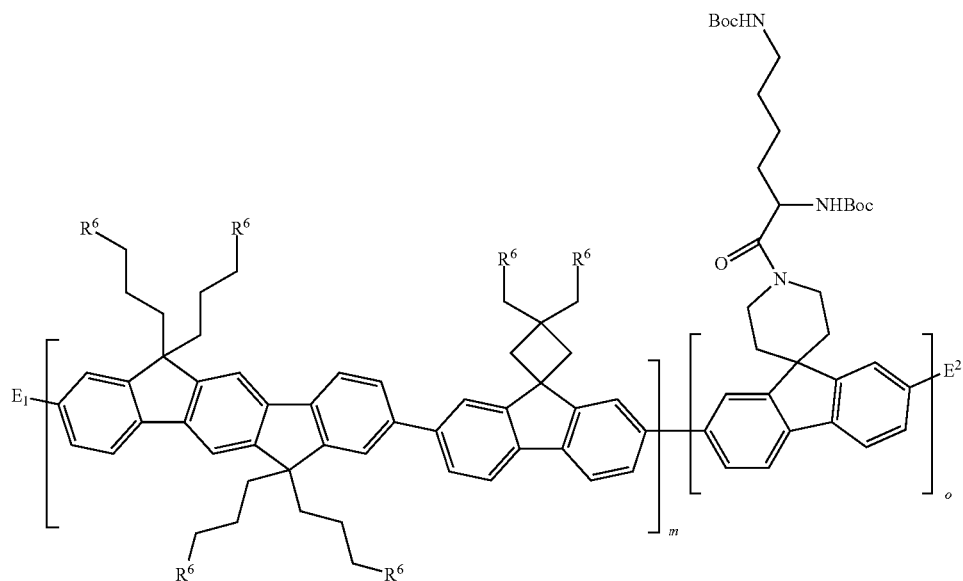
wherein "1" has the structure:
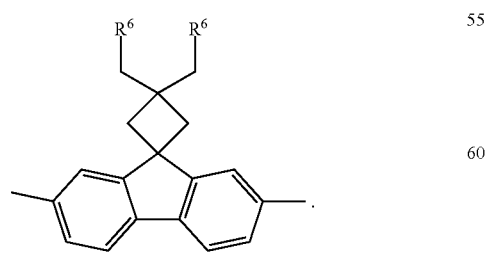

In certain aspects, the compound of formula II-a has the formula:

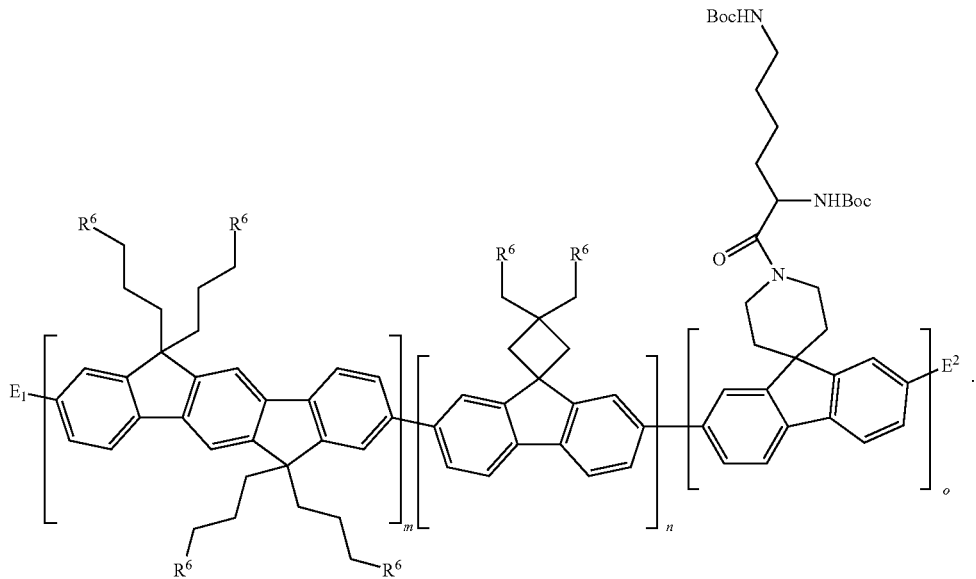

In certain aspects, m is 1-50, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50.

In certain aspects, n is 0-50, such as about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50.

In certain aspects, o is 0-50, such as about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50.

In certain aspects, each $R^6$ is independently a water soluble group, such as an ethylene oxide oligomer methyl ether. In certain aspects, the ethylene oxide oligomer methyl ether is between —O-$PEG_{11}$-$OCH_3$ and —O-$PEG_{550}$-$OCH_3$ inclusive, such as —O-$PEG_{11}$-$OCH_3$ and —O-$PEG_{550}$-$OCH_3$. In one aspect, $R^6$ is —O-$PEG_{11}$-$OCH_3$. In another aspect, $R^6$ is —O-$PEG_{550}$-$OCH_{13}$.

In certain aspects, NHBoc is tert-butyloxycarbonyl protecting $NH_2$ and can be removed to generate $NH_2$.

In certain aspects, the compound of formula II has the formula:

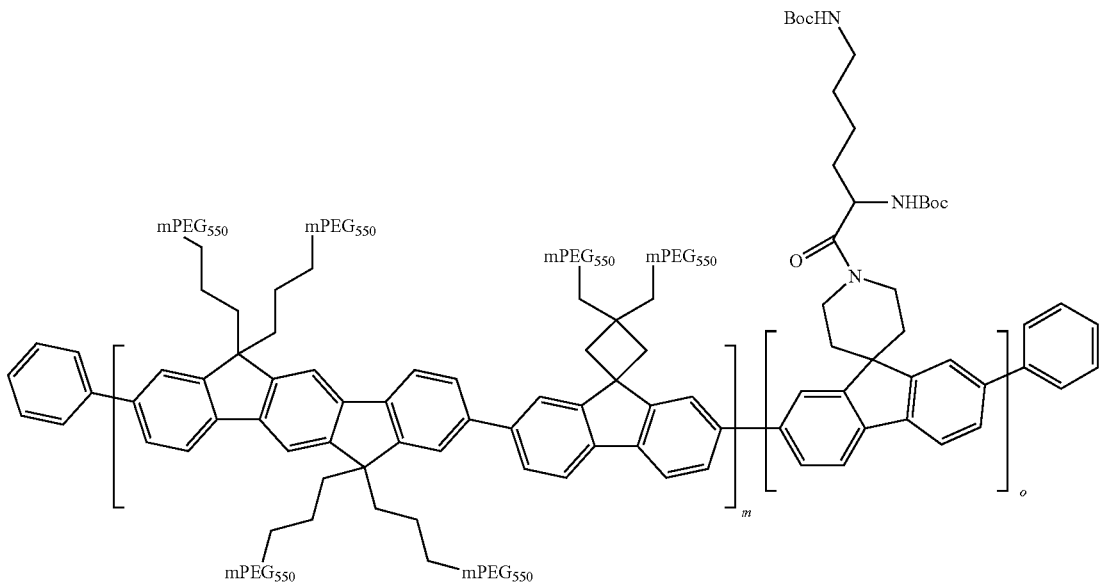

wherein "1" has the structure:
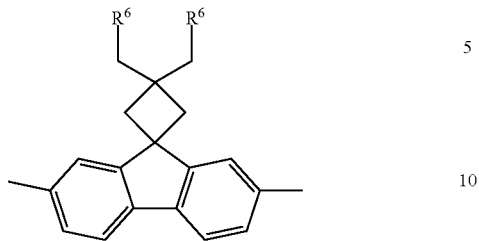
wherein the NHBoc group can be converted to an amine for optional conjugation.
In certain aspects, the compound of formula II-a has the formula:
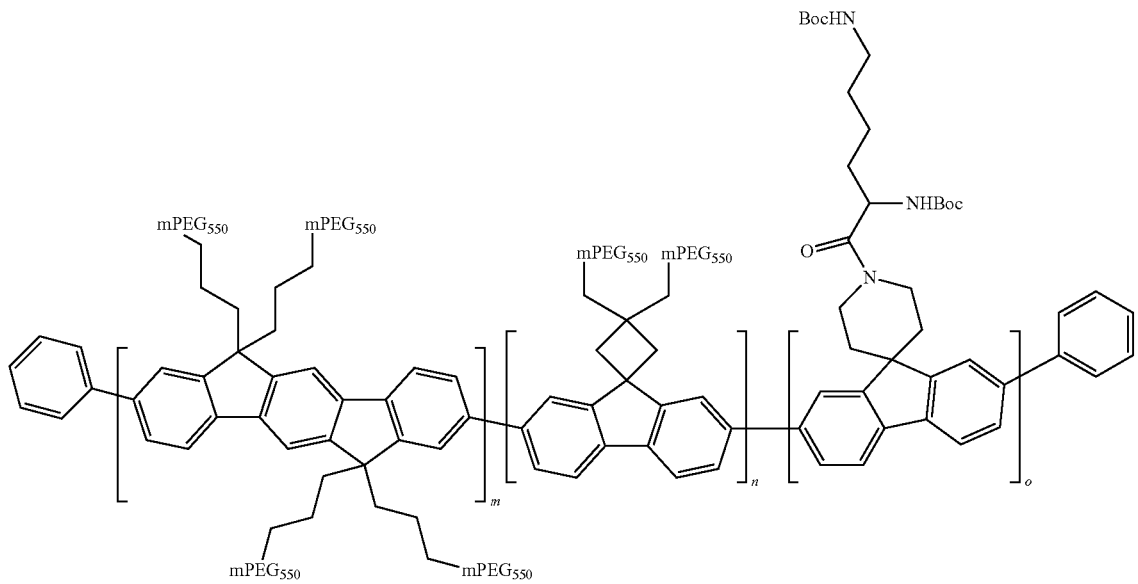
wherein the NHBoc group can be converted to an amine for optional conjugation.
In certain aspects, the compound of formula II-a has the formula:
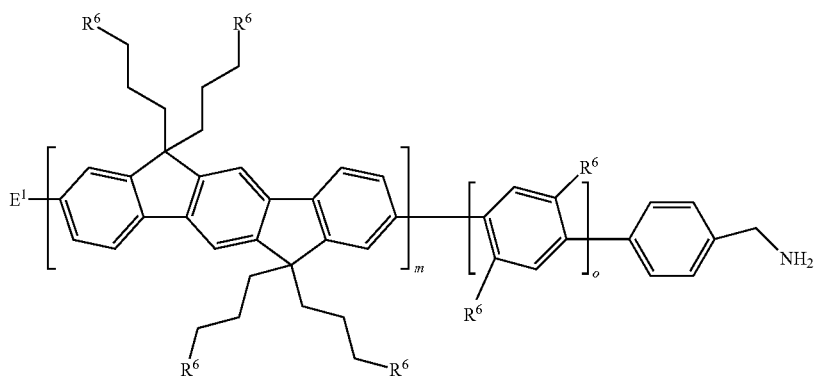

wherein $R^6$ is a water soluble group, such as an ethylene oxide oligomer methyl ether. In certain aspects, the ethylene oxide oligomer methyl ether is between —O-PEG$_{11}$-OCH$_3$ and —O-PEG$_{550}$-OCH$_3$ inclusive, such as —O-PEG$_{11}$-OCH$_3$ and —O-PEG$_{550}$-OCH$_3$. In one aspect, $R^6$ is —O-PEG$_{11}$-OCH$_3$. In one aspect, $R^6$ is —O-PEG$_{550}$-OCH$_3$.

In certain aspects, the compound of formula II-a has the formula:

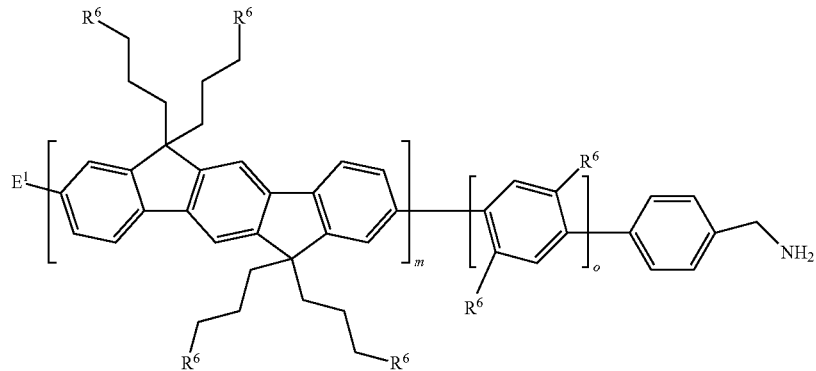

wherein $R^6$ is a water soluble group, such as an ethylene oxide oligomer methyl ether. In certain aspects, the ethylene oxide oligomer methyl ether is between —O-PEG$_{11}$-OCH$_3$ and —O-PEG$_{550}$-OCH$_3$ inclusive, such as —O-PEG$_{11}$-OCH$_3$ and —O-PEG$_{550}$-OCH$_3$. In one aspect, $R^6$ is —O-PEG$_{11}$-OCH$_3$. In one aspect, $R^6$ is —O-PEG$_{550}$-OCH$_3$.

In certain aspects, the compound of formula I-a has the formula:

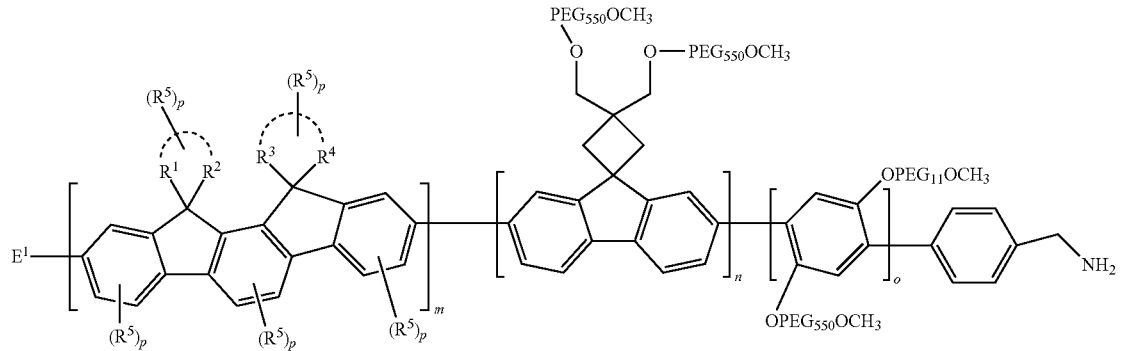

In certain aspects, the macromers (i.e., polymers) of formula I or II can range in size, depending on the polymerization conditions, catalysts, and types and amounts of monomers utilized in the polymerization reaction. For example, the macromers (i.e., polymers) can have a number average molecular weight ($M_n$) of about 5,000 to about 100,000. Macromers with $M_n$ of about 30,000 to about 70,000 are water-soluble and are not prone to aggregation in aqueous medium. Typically macromers of the disclosure have a narrow range of molecular weights. For example, the polydispersity of the macromers of formula I or II can be expressed in terms of a polydispersity index (PDI). The PDI can be calculated using the equation $DM=M_w/M_n$, wherein $M_w$ is the weight-average molar mass and $M_n$ is the number-average molar mass.

In certain aspects, macromers described herein can have a PDI ranging from about 1.2 to 2.2 such as 1.2, 1.3, 1.4, 1.5, 1.6, 1.7, 1.8, 1.9, 2.0, 2.1, or 2.2, where a polymer having a PDI from about 1.0 to about 1.5 can be considered monodisperse. In certain embodiments, the macromers of formula I or formula II have a $M_n$ of about 42,000-70,000 Daltons, with narrow distribution of PDI<1.5.

In certain aspects, the macromers of formula I or formula II are soluble in common organic solvents such as for example, THF, dichloromethane, methanol, toluene, and the like. Certain macromers described herein also are soluble in aqueous media, such as, for example, water, saline, buffered aqueous solutions such as borate, carbonate, or phosphate buffers and the like. Typically, the macromers of formula I or formula II exhibit aqueous solubility up to 1.0 mg/mL in water or buffers such as PBS.

In certain aspects, the macromers of formula I or formula II include a conjugated segment. Extended conjugation within the polymer backbone allows the macromers to exhibit fluorescence emission upon excitation at an appropriate wavelength of light. In certain instances, an aromatic group or heteroaromatic group such as A and/or B when present complete a π-conjugated backbone. Fluorescent macromers that include a conjugated segment can have a tunable photophysical property in the near ultraviolet (UV) to far infrared (IR) range. Because the disclosed macromers exhibit a host of favorable optical properties, this class of macromers are useful for biological assays requiring a high level of sensitivity.

In certain aspects, the macromers of formula I or formula II emit bright, visible light upon UV excitation and typically absorb light having a wavelength of about 500 nm or less (e.g., about 300 nm to about 500 nm). In certain embodiments, the disclosed polymers absorb light having a wavelength of about 350 nm to about 450 nm; or about 380 nm to about 410 nm. Macromers that can absorb light having a wavelength of about 405 nm can be effectively irradiated using a violet laser. Upon irradiation at an appropriate wavelength, the macromers can emit light having a wavelength of greater than about 400 nm; e.g., about 400 to about 800 nm; or about 400-780 nm. Incorporation of additional aromatic monomer residues (A, and/or B e.g., benzodithiazole, phenyl or thiophenyl) in the macromer backbone can alter the electronic properties of the macromer and shift the excitation and emission wavelength of the copolymer.

In certain aspects, the macromers of formula I or formula II can exhibit one or more of the following properties or characteristics: fluorescence emission upon excitation at an appropriate wavelength of light (e.g., below about 500 nm); emission of light having a wavelength of greater than about 400 nm; an extinction coefficient of greater than about $2\times10^6$ $cm^{-1}$ in water; and a number average molecular weight (Mn) of about 5,000 to about 70,000, such as 5,000, to about 10,000, or to 15,000, or to 20,000, or to 25,000, or to 30,000, or to 35,000, or to 40,000, or to 45,000, or to 50,000, or to 55,000, or to 60,000, or to 65,000, or to 70,000.

B. Methods Utilizing the Compounds

In one aspect, the macromers of the present disclosure are used in FRET assay 100 such as the one shown in FIG. 1. For example, a biomolecule such as an antibody 110 labeled with a dye 125 is reacted with a macromer 131 of the present disclosure. The macromer of the present disclosure reacts with the antibody 110 in a covalent manner to produce an antibody with the attached dye and macromer. In this assay method, energy is transferred between a donor fluorophore and an acceptor fluorophore if the two fluorophore are in close proximity to the each other. Excitation of the "donor" i.e., macromer 131 by an energy source (e.g. UV light) produces an energy transfer to the "acceptor" i.e., dye 125 if the two fluorophores are within a given proximity. In turn, the acceptor emits light characterized by the star like depiction of 125 at its characteristic wavelength.

Advantageously, interaction or binding between a macromer of the disclosure and dye-labeled antibodies increases detection sensitivies, for example, of a biomolecule target or analyte. In another aspect, covalently attaching a macromer of the disclosure to a dye attached to a biomolecule (e.g., an antibody complex), offers several advantages, including reduced background and/or improved energy transfer. In the case of direct linkage to a biomolecule, biorecognition events, rather than nonspecific macromer interaction or binding events, govern macromer presence. In this manner, nonspecific binding of macromers to biomolecules can be eliminated, reducing background emission resulting from unbound or uncomplexed conjugated macromer molecules in the reaction mixture.

Figure 2:
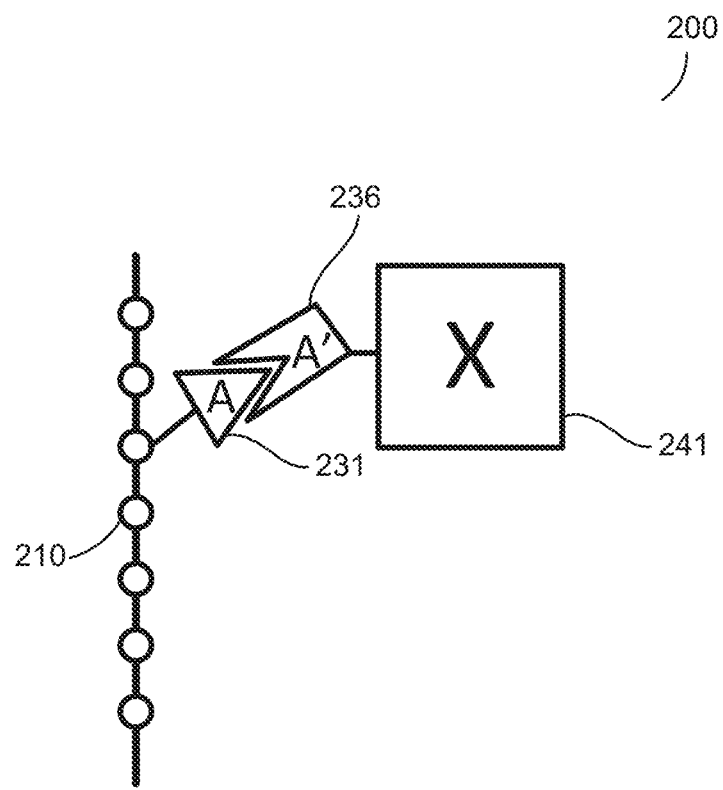
FIG. 2 illustrates a schematic of a bioconjugated macromer of one embodiment of the disclosure.

Turning now to FIG. 2, this schematic 200 illustrates a conjugated macromer 210 of one embodiment of the disclosure. In certain aspects, the macromer 210 of the disclosure is conjugated to an affinity ligand, i.e., a biomolecule that has an affinity for another biomolecule. FIG. 2 illustrates a class of materials according to the disclosure in which a macromer 210 is linked to for example, a dye, biomolecule, or biomolecule/dye complex i.e., "X" 241. Linking to the macromer can be via a first functionality 231 (A) on the macromer that serves as a bioconjugation site capable of covalently linking with a second functionality linker 236 (A') linked to a biomolecule and/or dye "X" 241. This arrangement can fix the distance between the macromer 210 and X 241, thereby ensuring only specific interactions between the macromer 210 of the disclosure and the moiety X 241. It is envisioned that a biomolecule component 241 in these embodiments can be any of the various biomolecules described herein, including, but not limited to, an antibody, protein, an affinity ligand, an enzyme, nucleic acid, or the like.

Advantageously, linker "A" 231 can be attached anywhere on the macromer, including at terminal positions of the macromer, internally on a repeating subunit, in between repeating subunits, or any combination thereof. Likewise, linker "A'" 236 can be linked to any suitable group on a biomolecule and/or dye X. The linking chemistry for A and A' (231, 236) to their respective macromer or biomolecule (or dye or dye-labeled biomolecule) can include, but is not limited to, complementary reactive groups such as maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate—periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 44N-maleimidomethylicyclohexane-1-carboxylate)/thiol; and amine/BMPH (N-[β-Maleimidopropionic acid] hydrazide•TFA)/thiol. Those of skill in the art will know of other complementary coupling chemistries useful for the present disclosure.

In certain aspects, the "X" moiety 241 in FIG. 2 in this context can be, but is not limited to, a dye, fluorescence protein, nanomaterial (e.g., Quantum Dot), chemluminescence-generating molecule, a conjugate between dye and chemluminescence-generating molecule, a conjugate between fluorescence protein and chemluminescence-generating molecule, a conjugate between nanomaterial (e.g., Quantum Dot) and chemluminescence-generating molecule, streptavidin, avidin, enzyme, substrate for an enzyme, substrate analog for an enzyme, receptor, ligand for a receptor, ligand analog for a receptor, DNA, RNA, modified nucleic acid, DNA aptamer, RNA aptamer, modified nucleic aptamer, peptide aptamer, antibody, antigen, phage, bacterium, or conjugate of any two of the items described above.

In certain aspects, the present disclosure provides a method for detecting an analyte in a sample, the method comprising:

(a) combining the sample and a macromer of the disclosure;

(b) exciting the macromer with light; and (c) detecting fluorescence from the macromer, thereby detecting the analyte.

Figures 3A, 3B, 3C, 3D:
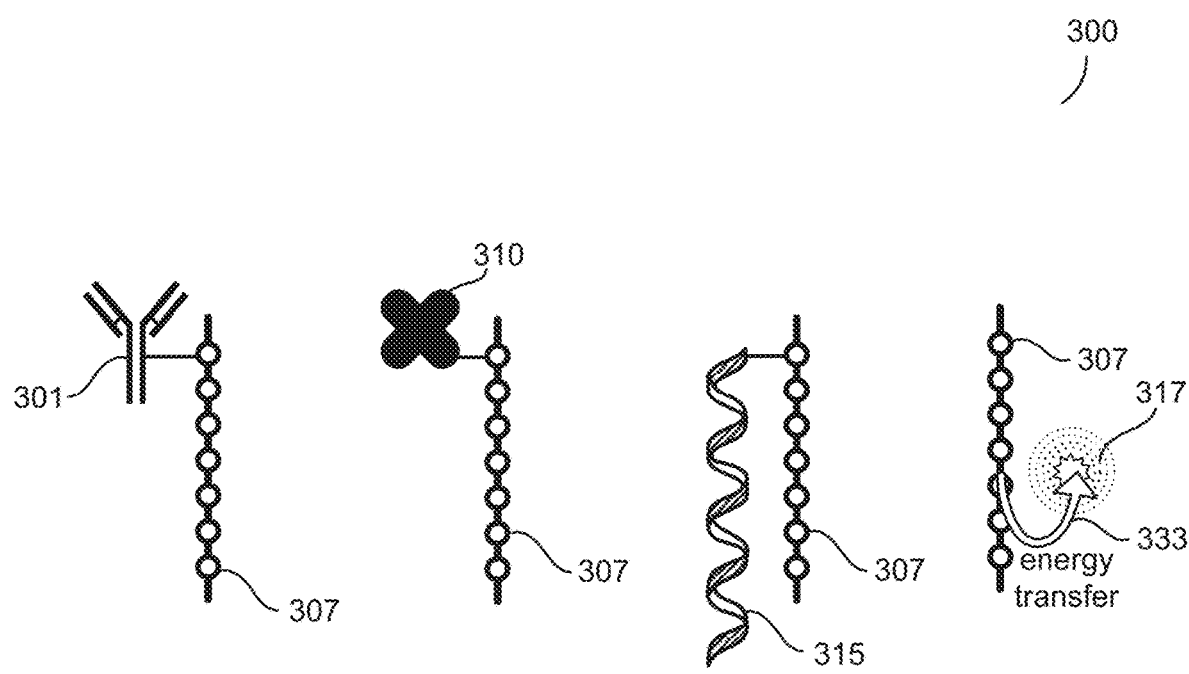
FIGS. 3A-D illustrates an exemplary macromer which is conjugated to an antibody (FIG. 3A); avidin (FIG. 3B); a nucleic acid (FIG. 3C); and a dye (FIG. 3D).

FIG. 3 is a schematic 300 that depicts an exemplary macromer that is conjugated to, for example, an antibody (A); avidin (B); a nucleic acid (C); and a dye (D). In certain aspects, the disclosure includes the use of these conjugated macromers as direct labels. In certain aspects, as is shown in FIG. 3A, a macromer 307 is conjugated to an antibody 301, which can be, for example, a primary or secondary antibody. The macromer conjugated to the antibody can be used as a direct reporter, for example, in a bioassay (e.g., an immunoassay). Excitation of the macromer with light can result in macromer emission, indicating the presence of the antibody in the assay or assay solution.

FIGS. 3B and 3C further exemplify the use of conjugated macromers of the disclosure as biomolecule labels capable of detecting specific targets, analytes and target-associated biomolecules. FIG. 3B depicts a macromer 307 conjugated to avidin (e.g., streptavidin, neutraAvidin, etc.; 310), capable of binding to biotin-modified molecules, biomolecules, or substrates. FIG. 3C depicts a nucleic acid (DNA, RNA, PNA, and the like) 315 conjugate that includes a macromer 307 of the disclosure covalently linked to a nucleic acid 315, which conjugate is capable of hybridizing to target nucleic acids that contain complementary nucleic acid sequences. Linkage or conjugation of fluorescent macromers to a molecule capable of recognizing a target biomolecule, analyte or target-associated molecule provides a direct means of detection. In other aspects, the signals generated from excitation of the macromer are not modulated by other assay components except those that are directly conjugated to the macromer. In such embodiments, the macromer acts directly as a fluorescent label.

In another aspect, as is shown in FIG. 3D, a macromer 307 of the disclosure is labeled with a dye 317, for example, a chromophore. In this embodiment, the conjugated macromer 307 can act as a donor and the dye 317 can act as an acceptor in an energy transfer process. Here, the conjugated macromer can act as a light harvester, and excitation of the conjugated macromer is followed by the channeling of the excitations to the dye via an energy transfer process such as fluorescence resonance energy transfer (FRET) 333. This results in amplified dye emission (as compared to direct excitation of the dye). The fluorescence of the donor conjugated macromer, in one embodiment, can be quenched (e.g., >90% quenching).

A wide variety of dyes can be used in the present disclosure. In some aspects, a functional group is used to label the dye to form a fluorescence resonance energy transfer (FRET) pair. Excitation wavelengths are preferably between about 200-900 nm such as about 200 nm, 220 nm, 240 nm, 260 nm, 280 nm, 300 nm, 320 nm, 340 nm, 360 nm, 380 nm, 400 nm, 420 nm, 440 nm, 460 nm, 480 nm, 500 nm, 520 nm, 540 nm, 560 nm, 580 nm, 600 nm, 620 nm, 640 nm, 660 nm, 680 nm, 700 nm, 720 nm, 740 nm, 760 nm, 780 nm, 800 nm, 820 nm, 840 nm, 860 nm, 880 nm, and/or 900 nm. The emission wavelength is preferably around about 200-900 nm such as about 200 nm, 220 nm, 240 nm, 260 nm, 280 nm, 300 nm, 320 nm, 340 nm, 360 nm, 380 nm, 400 nm, 420 nm, 440 nm, 460 nm, 480 nm, 500 nm, 520 nm, 540 nm, 560 nm, 580 nm, 600 nm, 620 nm, 640 nm, 660 nm, 680 nm, 700 nm, 720 nm, 740 nm, 760 nm, 780 nm, 800 nm, 820 nm, 840 nm, 860 nm, 880 nm, and/or about 900 nm.

Exemplary fluorescent dyes include, but are not limited to, fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy-Chrome, phycoerythrin, PerCP (peridinin chlorophyll-a Protein), PerCP-Cy5.5, JOE (6-carboxy-4,5-dichloro-2,7-dimelhoxyfluorescein), NED, ROX (5-(and—6)-carboxy-X-rhodamine), HEX, *Lucifer* Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br2, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof, and combinations thereof. Exemplary lanthanide chelates include europium chelates, terbium chelates and samarium chelates. Those of skill in the art will know of other dyes useful top practice the present disclosure.

In certain instances, the dye can be a quencher dye. Quencher dyes include, but are not limited to (absorption max), Dabcyl (453), QSY35 (475), BHQ-0 (495), Eclipse (530), BHQ-1 (534), QSY 7 (560), QSY 9 (562), BHQ-2 (579), Elle-Quencher (630), Iowa Black (651), QSY 21 (661), and BHQ-3 (672). In certain instances, when a macromere of this disclosure is substituted with one or more substituents such as nitro, cyano, or an optionally substituted amino, the macromer will be a quencher dye.

FIG. 4 (A) illustrates an antibody 405 labeled with a dye 410 and a macromer 407 according to the disclosure for use in a FRET assay with UV light 413; FIG. 4 (B) illustrates streptavidin (SA) 425 labeled with a dye 420 and labeled with a macromer 407 according to the disclosure for use in a FRET assay with UV light 413; FIG. 4 (C) illustrates a nucleic acid probe sequence 427 labeled with a quencher molecule 431 conjugated to a macromer 407 of the disclosure, nucleic acid probe sequence 436 hybridizes with sequence 427; FIG. 4(D) illustrates a nucleic acid probe sequence 427 labeled with a quencher molecule 431 and macromer 407, with an appended dye 441 tandem complex. The nucleic acid probe sequence 427 hybridizes to sequence 436.

In the case of direct linkage of a macromer of the disclosure to a dye (FIG. 3D) or biomolecule/dye complex (as exemplified in FIG. 4), donor-acceptor distances can be fixed, rather than dependent on the strength of interaction or binding, and energy transfer efficiency can be significantly increased. This has significant consequences in the context of improving dye signaling (or quenching) and reducing background fluorescence associated with donor-acceptor cross-talk. Cross-talk in this case refers to the overlap between the macromer (donor's) and dye's (acceptor's) emission peaks. As will be appreciated, macromers that bind non-specifically at distances too great for energy transfer can contribute to the background fluorescence (or cross-talk). Shorter (fixed) distances between the donor and acceptor can thus not only facilitate direct dye amplification, but also can greatly quench the donor emission.

Figure 5A:
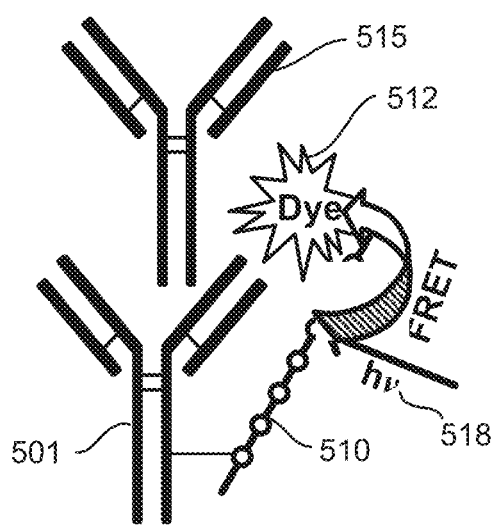
FIGS. 5A-D illustrate a schematic that depicts various methods of assaying for a target biomolecule or analyte.
Figure 5B:
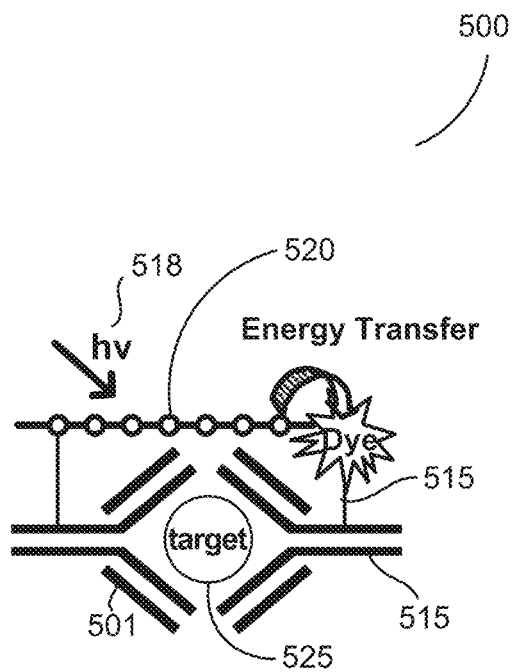
Figure 5C:
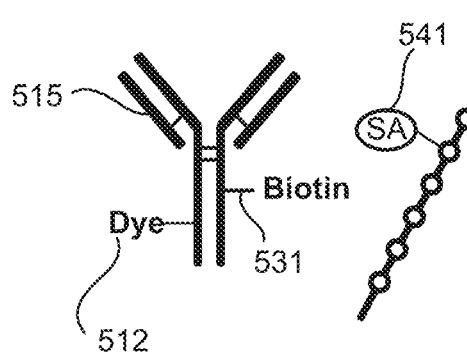
Figure 5D:
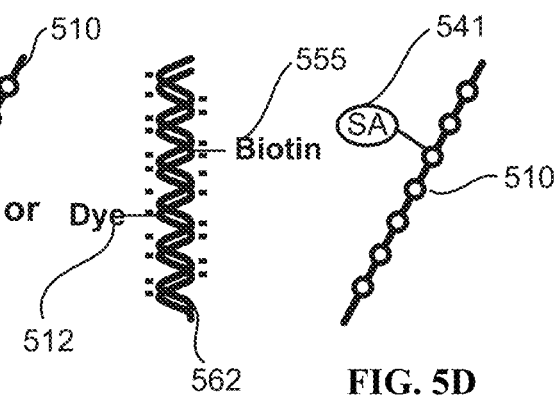

FIG. 5 illustrates a schematic that depicts various methods of assaying for a target biomolecule, analyte or target associated biomolecule. For example, FIG. 5 (A) shows a macromer 510 linked to a first antibody 501 bound to a second antibody 515 with a dye 512;

FIG. 5(B) illustrates a macromer 520 and dye 512 labeled antibodies recognize a common target 525; FIG. 5(C) illustrates an antibody 515 with a linked dye 512 and biotin 531 and a second bioconjugate of streptavidin 541 with a macromer 510 appended thereto; and FIG. 5 (D) illustrates a nucleic acid 562 with a dye 512 and biotin bound 555 thereto and streptavidin 541 with a macromer 510 conjugated thereto.

Figure 6:
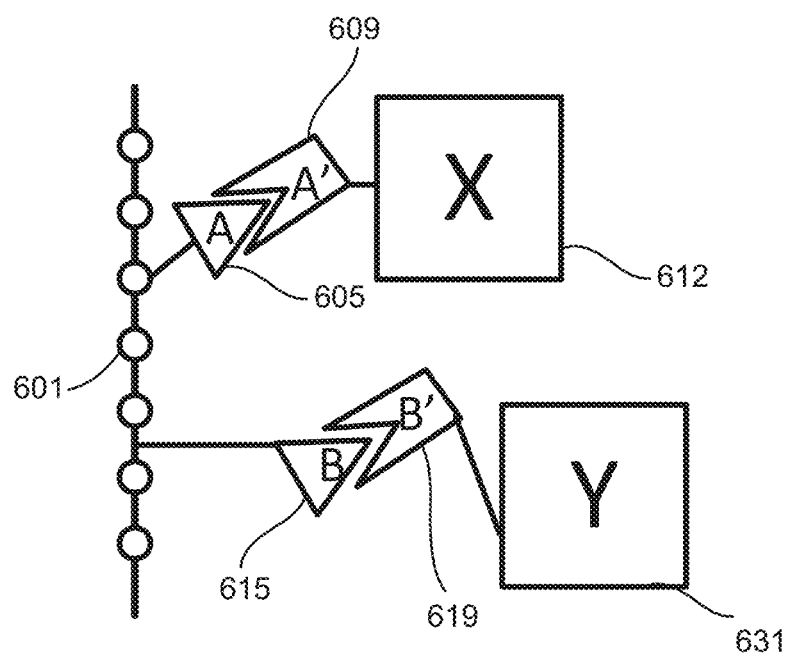
FIG. 6 illustrates a schematic according to the present disclosure.

Turning to FIG. 6, illustrated therein is a schematic that depicts a first linking site 605 (A) and a second linking site 615 (B) within a macromer 601 to append a "X" moiety 612 such as a dye and a "Y" moiety 631 such as an antibody by complementary linker 609 (A') and linker 619 (B'), respectively.

Figure 7A:
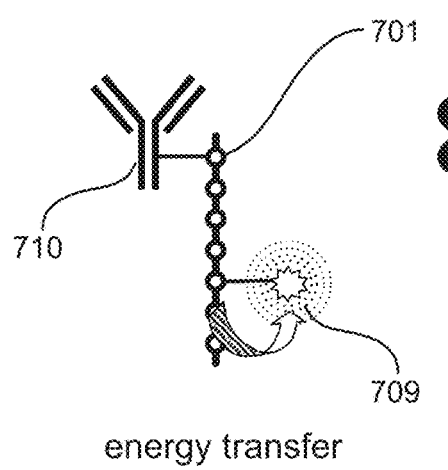
FIGS. 7A-C illustrate various schematic of the disclosure.
Figure 7B:
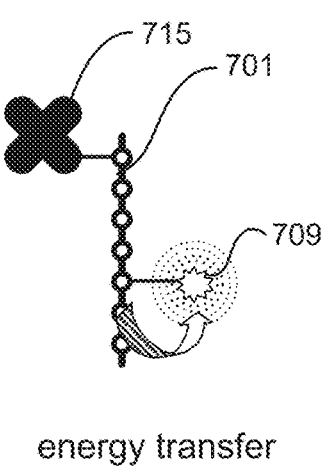
Figure 7C:
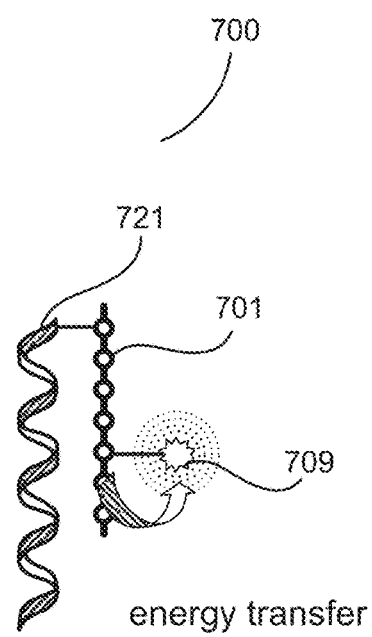

FIG. 7(A) illustrates a schematic that depicts a macromer 701 with a linked dye 709 and a biomolecule 710 and resulting energy transfer; FIG. 7(B) illustrates a macromer 701 with a conjugated streptavidin 715 and a linked dye 709;

and FIG. 7(C) illustrates a macromer 701 conjugated to a nucleic acid 721 and a dye 709.

Figures 8A, 8B, 8C, 8D, 8E, 8F:
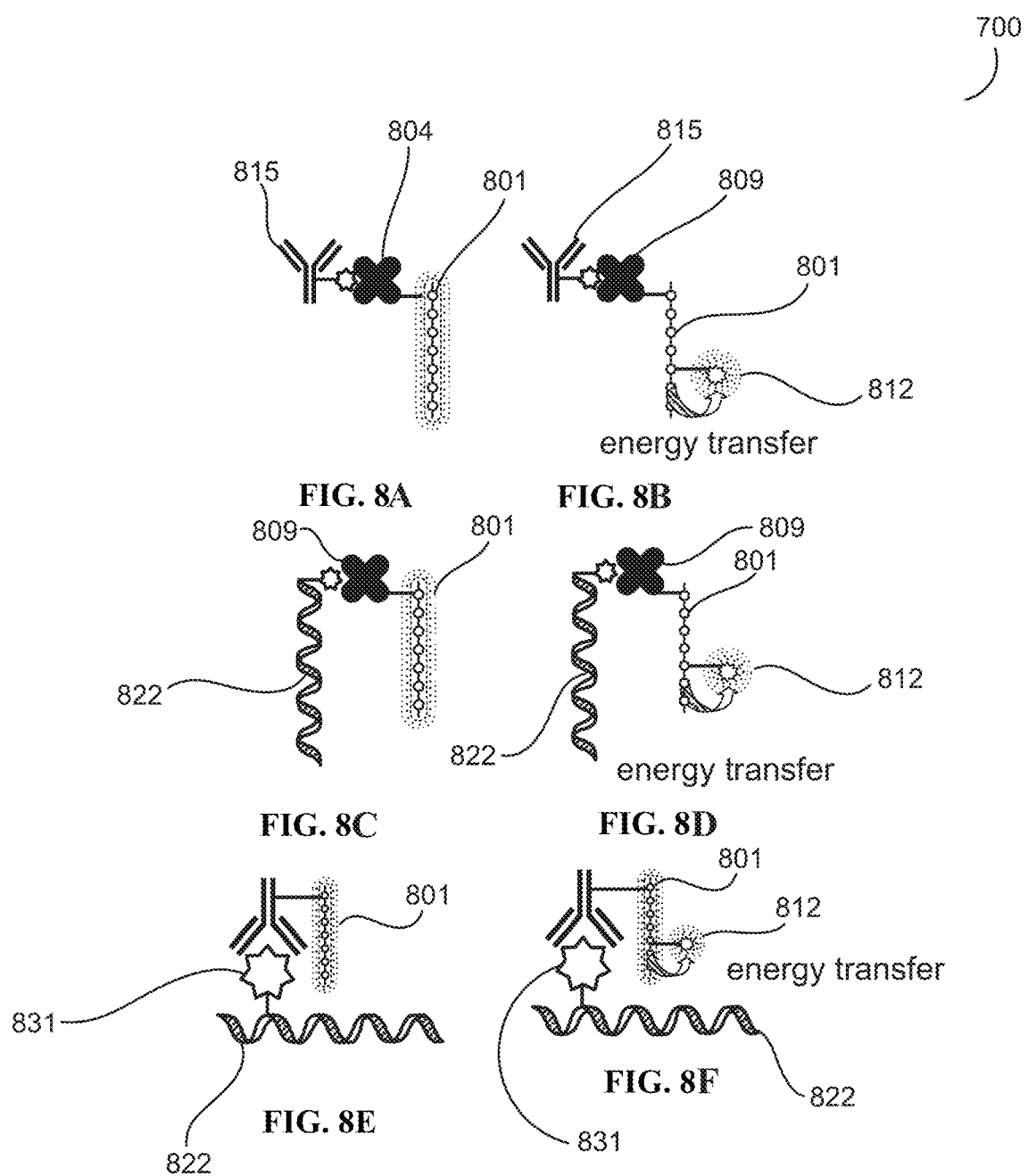
FIGS. 8A-F illustrate schematics that depict indirect associations with macromers linked to a biomolecule.

FIG. 8 illustrates a schematic that depicts indirect associations with macromers linked to a biomolecule. For example, FIG. 8(A) shows a biotinylated antibody 815 interacting with a covalent conjugate 804 of a macromer 801; FIG. 8(B) shows a biotinylated antibody 815 interacting with a moiety 809 linked to a macromer 801 having a linked dye 812; FIG. 8(C) shows a biotinylated nucleic acid 822 interacting with a covalent moiety 809 of a macromer; FIG. 8(D) shows a biotinylated nucleic acid 822 bound to a linked moiety 809 of a macromer 801 having a linked dye 812; FIG. 8(E) shows a nucleic acid 822 with digoxygenin moiety 831 interacting with a covalently linked antibody of the macromer 801; and FIG. 8(F) shows a nucleic acid 822 with digoxygenin moiety 831 and a covalent antibody to a macromer dye 812 tandem complex.

Figure 9A:
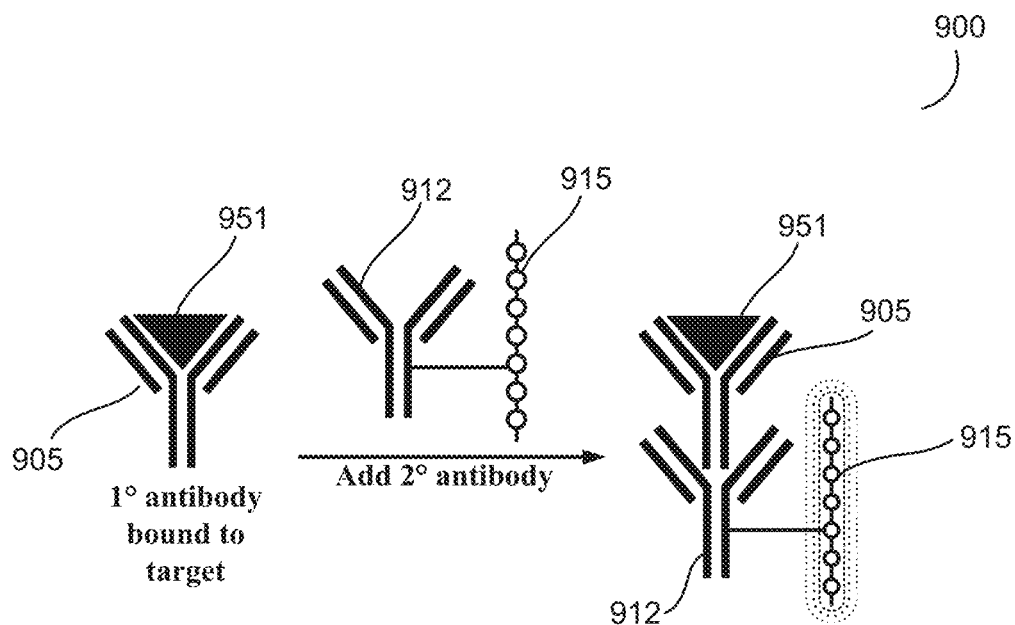
FIGS. 9A-B show assay embodiments of the disclosure.
Figure 9B:
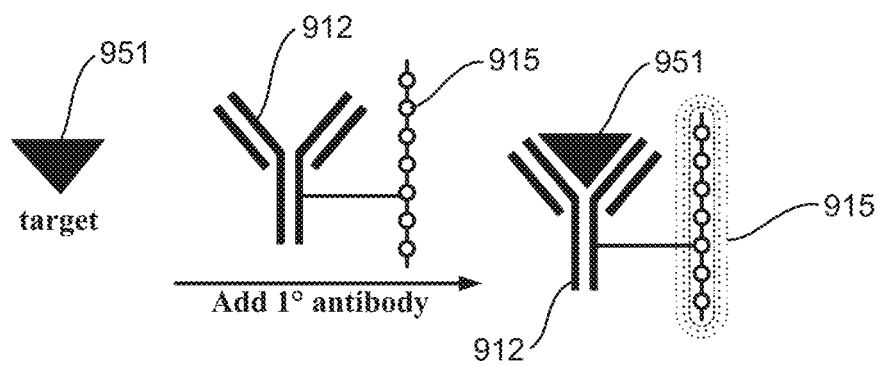

FIG. 9A shows a primary antibody 905 bound to an analyte 951 wherein a secondary antibody 912 having a macromer appended thereto 915 is added. In FIG. 9B, a target analyte 951 binds to a primary antibody 912 with a linked macromer 915.

Figure 10A:
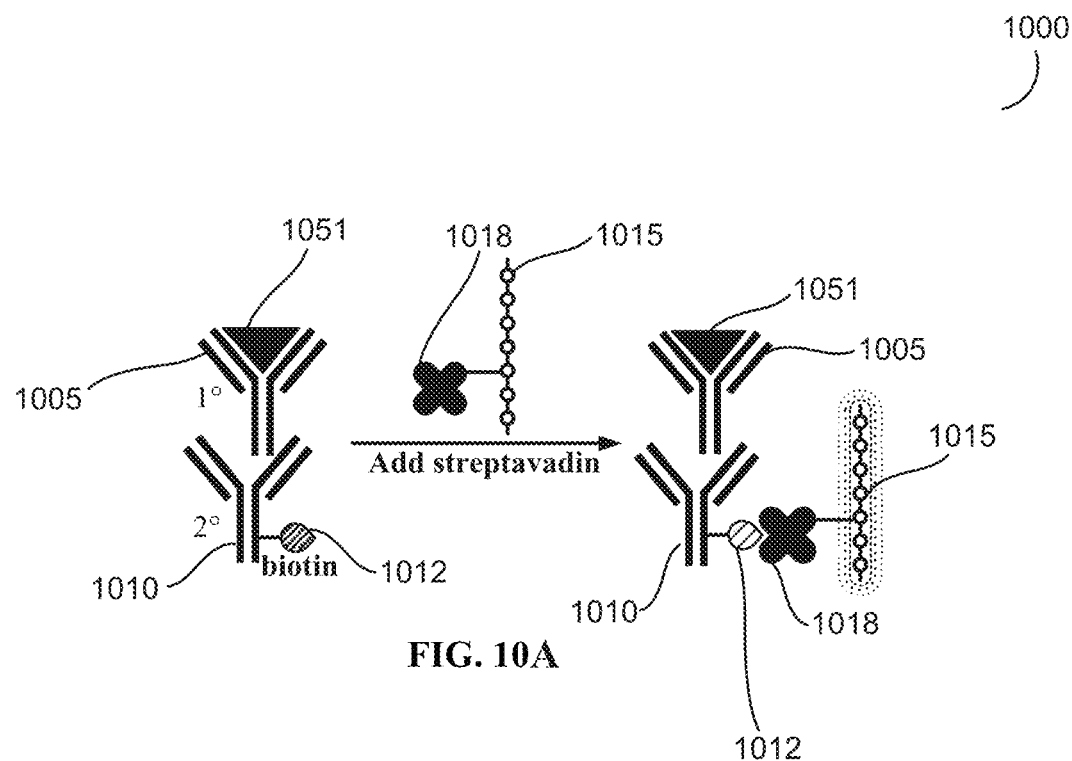
FIGS. 10A-B show sandwich-type complex embodiments.

FIG. 10A shows a sandwich-type complex, wherein a primary antibody 1005 binds an analyte 1051. A secondary antibody 1010 with a biotin 1012 is then added. Next, a macromer 1015 with a streptavidin 1018 is added to generate a sandwich complex.

Figure 10B:
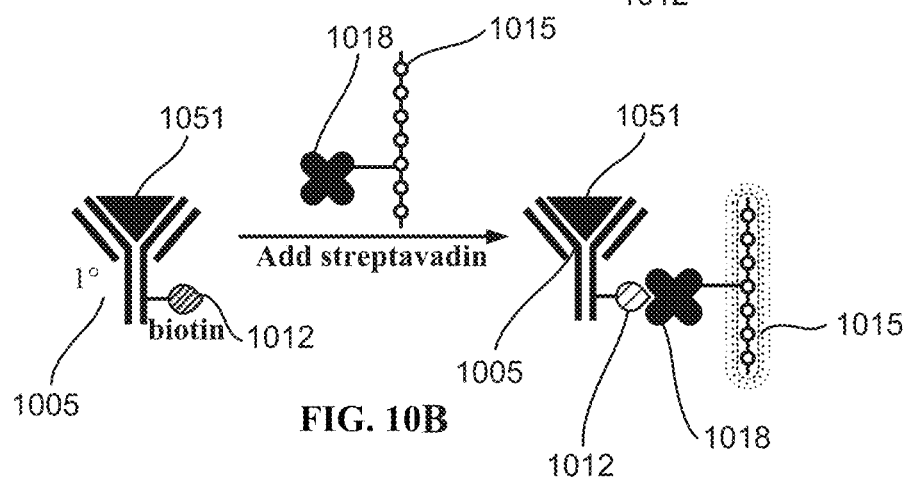

FIG. 10B shows a biotin 1012 labeled primary antibody 1005 with an analyte 1051 bound. A streptavidin 1118 linked to a macromer 1015 is added.

In certain aspects, the present disclosure provides a method for detecting a target biomolecule in a sample, the method comprising:

providing a sample that is suspected of containing a target analyte;

providing a macromer described herein conjugated to a capture molecule, wherein the capture molecule is capable of interacting with the target analyte; and contacting the sample with the capture molecule and the conjugated macromer under conditions in which the capture molecule can bind to the target analyte if present;

applying a light source to the sample that excites the conjugated macromer; and detecting whether light is emitted from the conjugated macromer.

In certain aspects, the method is performed in vivo. In certain aspects, the sample contains a living cell. In certain aspects, the analyte is a nucleic acid which comprises a genetic point mutation, deletion or insertion relative to a control nucleic acid. In certain aspects, the detection of the nucleic acid indicates the presence of a cancer in the sample.

C. Methods Making the Compounds

In one embodiment, the disclosure provides a method for synthesizing a compounds as described herein. In certain instances, monomeric units can be derivatized to diboronic esters, which monomers can subsequently be used for polymerization such as, for example, via Suzuki coupling. See *J. Am. Chem. Soc.*, 2014, 136, 14027-14030. Polymeric fluorenes may also be obtained through the use of other reaction schemes involving organometallic catalysis. For example, the Yamamoto reaction uses a nickel(0)-based catalyst for the homo-coupling of aryl halide monomers. Additionally, conjugated polymers can also be synthesized using Stille, Heck, and Sonogashira coupling reactions. See, e.g., Yamamoto et al., *Macromolecules* 25: 1214-1223, 1992; Kreyenschmidt et al., *Macromolecules* 28: 4577-4582, 1995; and Pei et al., *J. Am. Chem. Soc.* 118: 7416-7417, 1996 regarding Yamamoto reaction schemes. See, also, Leclerc, *Polym. Sci. Part A: Polym. Chem.* 39: 2867-2873, 2001 for Stille reaction schemes; Mikroyannidis et al., *J. Polym. Sci. Part A: Polym. Chem.* 45: 4661-4670, 2007 for Heck reaction schemes; and Sonogashira et al., *Tetrahedron Lett.* 16: 4467-4470, 1975 and Lee et al., Org. Lett. 3: 2005-2007, 2001 for Sonogashira reaction schemes.

In certain aspects, the methods of making the macromers of formula I or formula II comprise combining a plurality of reactive monomers to form a reaction mixture, wherein a first portion of the reactive monomers bears first reactive groups and a second portion of the monomers bears second reactive groups, wherein the first and second reactive groups are different and capable of reacting with each other to form a polymer. In certain aspects, at least one reactive monomer includes a monomer that is optionally substituted with one or more water-solubilizing groups. The reaction mixture is then subjected to conditions wherein the first and second reactive groups on the monomers react to form a polymer. In some methods, a plurality of monomers bearing suitable polymerizable groups are condensed to produce a macromer that includes a polymer backbone formed of the linked monomer residues.

In certain aspects, various types of polymerization strategies can be employed to couple the polymerizable monomers described herein. As mentioned, one representative method for preparing conjugated macromers described herein involves Yamamoto polymerization of monomers bearing halide functional groups in the presence of a metal catalyst (e.g., nickel). In certain instances, the Yamamoto reaction will produce a random copolymer or a grafting copolymer product.

In certain aspects, the process includes heating Ni(COD)2, Di-Py, COD in a solvent mixture of toluene and DMF at 70° C. for 30 min, then adding the monomers to the catalyst mixture and heating the mixture under argon or an inert atmosphere for 2-3 days.

In certain aspects, the polymerization process comprises polymerizing functionalized monomers within a certain size range to produce "polymer intermediates" having a larger size range, which intermediates are soluble in standard, widely used organic solvents. These polymer intermediate compounds can then be further modified by any now known or later developed suitable chemistry. These processes result in polymers that are soluble in aqueous solution, and which can be used directly for, for example, antibody conjugation applications, because of a certain high content of poly (ethylene oxide) present.

In certain aspects, monomer subunits can be pegylated or non-pegylated monomers, with the number of monomers ranging from about 50 to about 30000.

In certain aspects, PEG size can be up to 5,000 kDa; and monomer subunits of moderate size (MW about 300 to about 2000 kD).

In certain aspects, the polymerization process can include the same monomers to produces a homopolymer or different monomers to produce copolymers.

In certain aspects, the reaction is carried out in an aprotic solvent such as THF, DMF, toluene, acetonitrile and other suitable organic solvents.

In certain aspects, the polymerization strategy involves Suzuki polycondensation. The Suzuki reaction is a Pd-catalyzed coupling reaction between an aromatic boronic acid derivative and an aromatic halide that yields the corresponding biphenyl. In general, Suzuki polymerization involves coupling aromatic monomers that are each provided with two reactive functional groups. Appropriate functional groups for Suzuki polymerization include halides (e.g., Br or I) and boron-containing functional groups, such as boronic acid, a boronic ester (e.g., $C_1$-$C_6$ boronic acid ester), a borane group (e.g., $C_1$-$C_6$ borane) and $BF_3$ groups. In one exemplary method, a first reactive dihalide monomer is polymerized with a second monomer having two boron derivative functional groups. In this arrangement the first and the second monomers can be the same to produce a homopolymer or different to produce an alternating copolymer. In a second exemplary method, a monomer having a boron derivative functional group and a reactive halide functional group is polymerized to form a homopolymer. Copolymers can be prepared using such an arrangement by polymerizing together two or more different types of monomers each containing both functionalities. In certain instances, the Suzuki reaction produces an alternating copolymer product or main homopolymer with a certain content of an alternating segment, by adjusting the ratio of monomers.

In certain aspects, a representative Suzuki polymerization reaction involves forming a reaction mixture that includes (a) an aromatic monomer having at least two reactive boron-containing groups and an aromatic monomer having at least two reactive halide functional groups; or (b) an aromatic monomer having one reactive halide functional group and one reactive boron-containing group. The reaction is conducted in a solvent in which the conjugated macromer is soluble. Suitable solvents include water-miscible, polar solvents such as THF, DMF, and toluene. Included in the reaction mixture is a catalytic amount of a catalyst to catalyze the polymerization of the aromatic monomers. The reaction can be catalyzed using a soluble Pd source. Pd (II) salts (e.g., Pd acetate) or Pd (0) complexes such as $Pd(Ph_3P)_4$ are examples of suitable Pd sources that can be used in the methods disclosed herein. The reaction also includes a base in an amount sufficient to convert the reactive boron-containing functional groups into anionic —$BX3^-$ groups, wherein X is independently F or OH. Suitable bases include inorganic base, such as, for example, alkali metal carbonates or bicarbonates, such as potassium or sodium bicarbonate.

In certain aspects, monomers described herein are polymerized via Suzuki polycondensation to produce a 2,7-linked macromer. For example, dibromo and bis(boronate) 2,7-disubstituted monomers can be polymerized as described herein to yield a poly (2,7-monomer). The polymerization reaction can utilize monomers as described herein, which can optionally bear one or more water-solubilizing groups. Addition of aromatic monomers (e.g., arenes or heteroarenes) bearing suitable polymerizable groups into the reaction mixture can provide copolymers having a backbone that includes linked monomers and aromatic monomer residues. In certain methods, the additional monomers can include optionally substituted arene (e.g., fluorene) or heteroarene groups, thereby forming a copolymer having a polymer backbone comprising residues of arene or heteroarene monomers. In any of the polymerization methods described herein, polymerizable monomers bearing one or more water-solubilizing groups can be used in the polymerization reaction to afford water-soluble polymers and copolymers.

The figure below sets out two representative reaction schemes to yield a desired representative PEGylated conjugate of the invention; the upper scheme utilizes Yamamoto coupling chemistry while the lower scheme employs palladium-catalyzed Suzuki reaction chemistry. A polyindenofluorene copolymer are included as well.

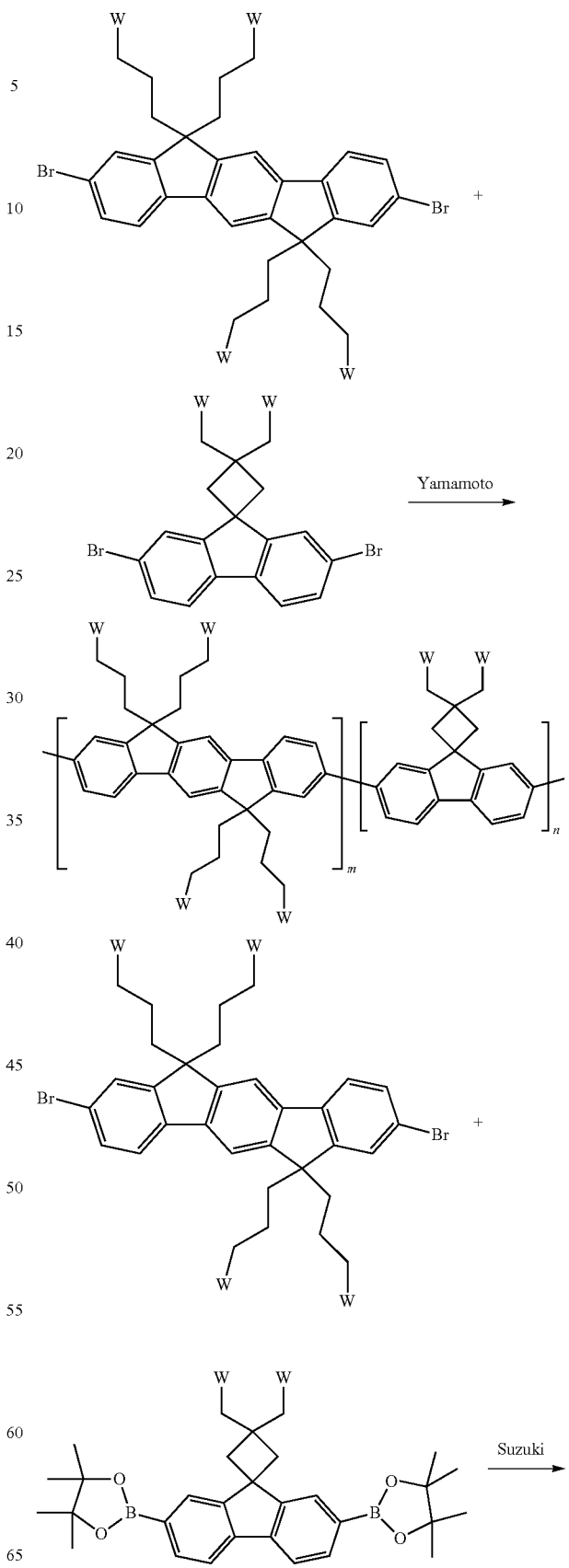

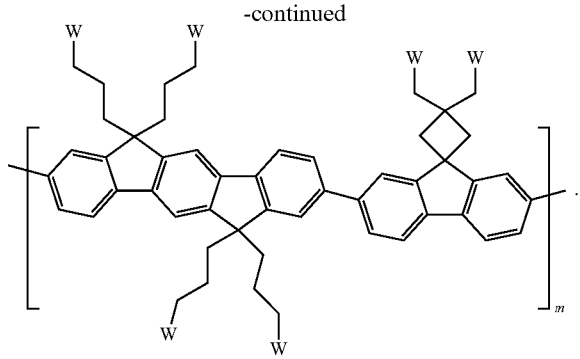

W = water soluble group, such as mPEG11, mPEG550, etc

In certain aspects, solubility is a characteristic feature for the macromers of the present disclosure. There are several methods to introduce water-soluble groups such as polyethylene glycol (PEG) to polymers to increase their solubility in water. In certain aspects, the peglated monomer is polymerized to the polymer or copolymer directly. For other aspects, a polymer or copolymer is made first and then post-modification processe(s) introduce PEG to functional groups present in the polymer to increase water solubility. Some representative process strategies for modifying polymers are provided below.

1. Strategy I—Williamson Ether Approach

In certain aspects, the polymer intermediate is formed by polymerizing hydroxyl (—OH) functionalized monomers, bromoalkyl monomer, and NH-Boc protected monomers. The resulting polymer is then modified with a reactive mPEG and functional group such as —OH, NH$_2$, Br in the polymer bachbone. As will be appreciated, the appropriate post-modification steps are performed based on the functional group moiety linked to the functionalized backbone in the polymer chain and the mPEG monomers.

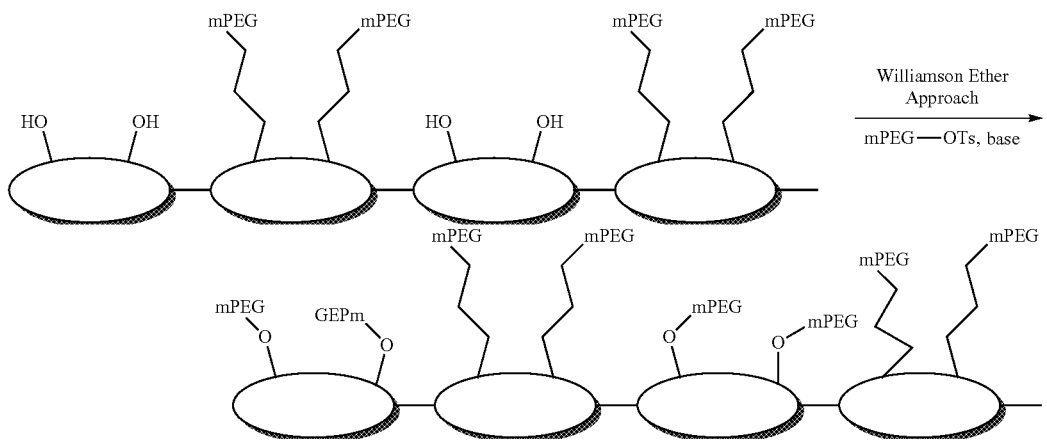

2. Strategy II—Anionic Polymerization

In certain aspects, mPEG monomers and hydroxyl monomers are copolymerized, then anionic polymerization of ethylene oxide is grafted on the polymer —OH groups as shown below.

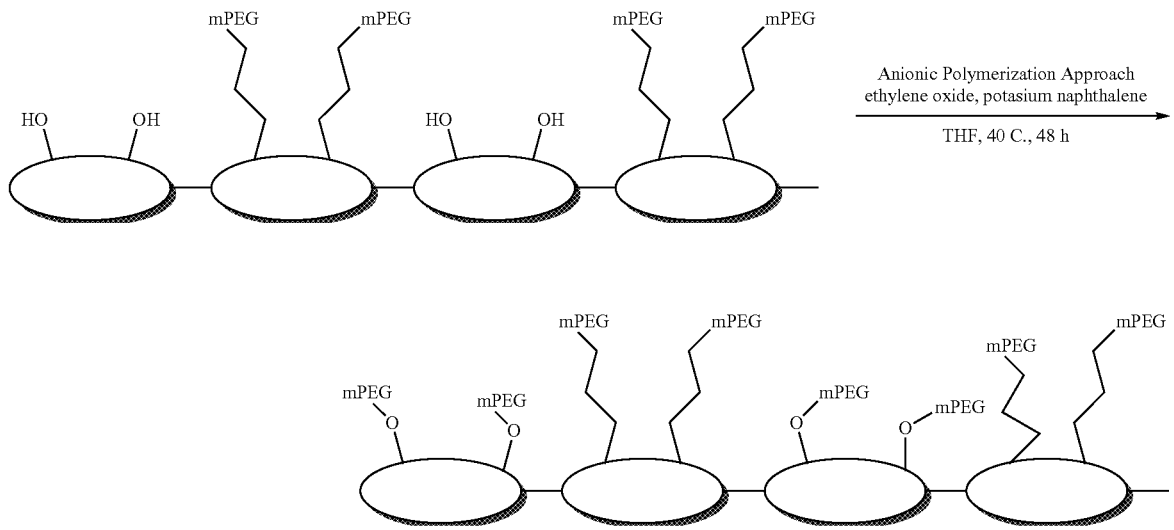

3. Strategy III—Coupling Reaction

In certain aspects, mPEG monomers and amine containing monomers are copolymerized, then mPEG-COOH groups are coupled to the amine groups by EDC chemistry to form an amide bond as shown below.

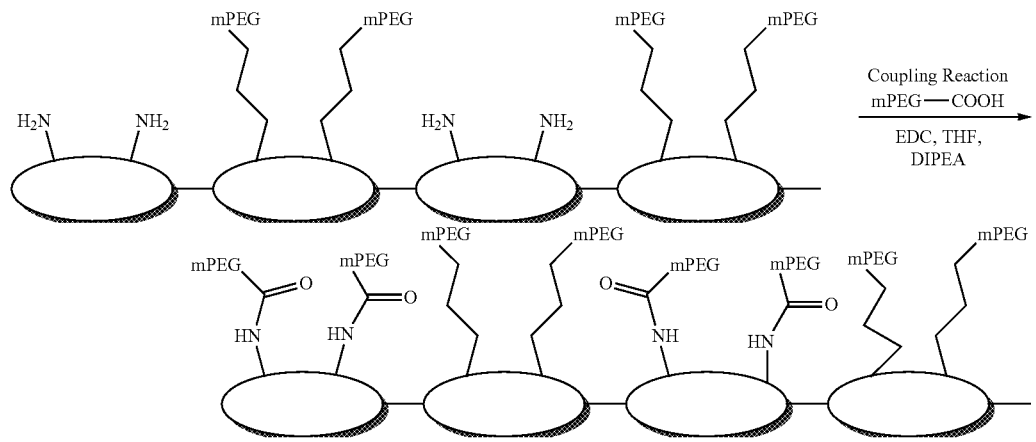

4. Strategy IV—Click Chemistry

In certain aspects, mPEG monomers and hydroxyl containing monomers are copolymerized, then the polymer is coupled with an alkyn bromide species to form a polymer containing an alkyn group. This reaction is followed by click chemistry to form a triazine ring with azide-functionalized mPEG molecules as shown below:

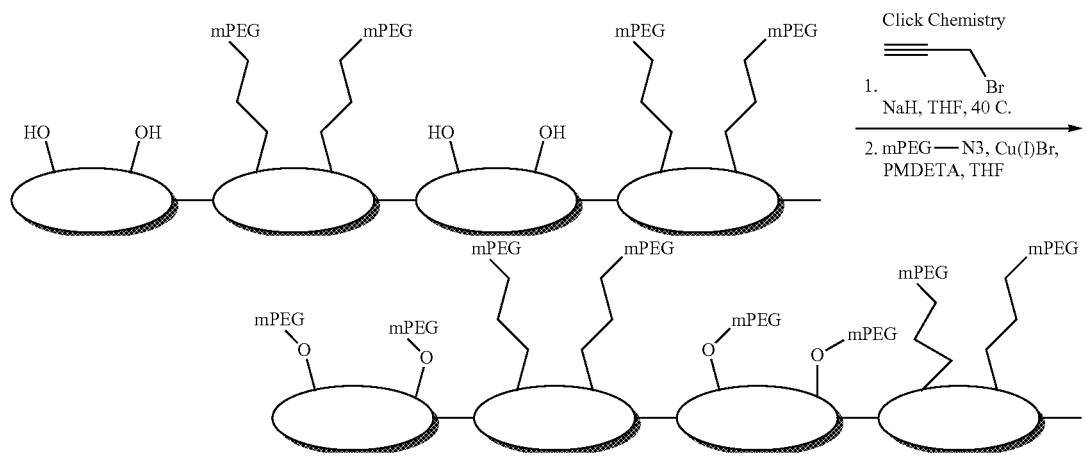

5. Strategy V—Schiff Base Reduction

In certain aspects, mPEG monomers and amine containing monomers are copolymerized. The resulting polymers are coupled with mPEG aldehyde-functionalized moieties, after which the C=N bonds can be reduced using a suitable reducing reagent as shown below.

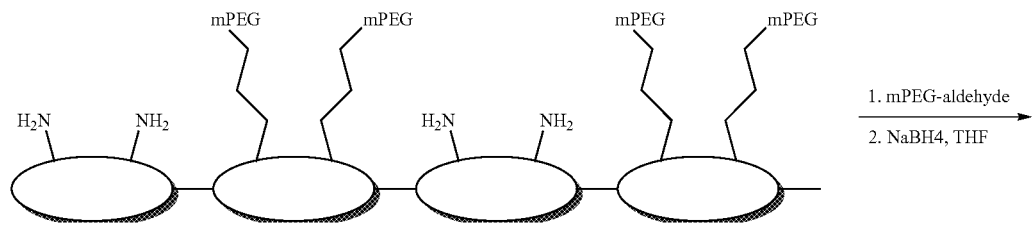

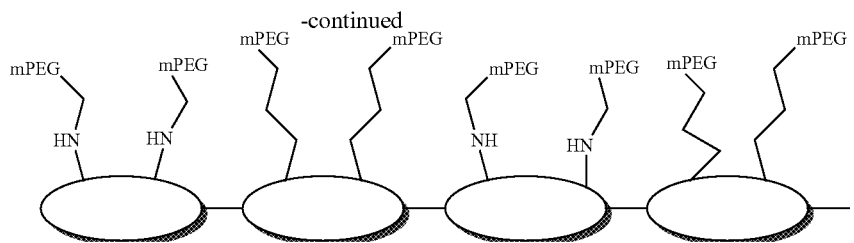

EXAMPLES

The following examples are offered to illustrate, but not to limit the claimed invention.

Example 1 illustrates the synthesis of 6,12-dihydroindeno[1,2-b]fluorine.

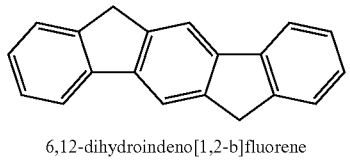 [SMILES: c1ccc2c(c1)Cc1cc3c(cc1-2)Cc1ccccc1-3]

6,12-dihydroindeno[1,2-b]fluorene 4.00 g (14.17 mmol) of the indeno[1,2-b]fluorene-6,12-dione are suspended in 330 mL triethylene glycol and mixed with 19.7 g (24.80 eq., 351.41 mmol) KOH. Carefully, 26.5 mL (29.89 eq., 423.49 mmol) of a hydrazine monohydrate solution (80%) were added to the mixture and heated to 170° C. for 24 hours. The reaction mixture was cooled to room temperature and poured into a mixture of 1 L ice water and 60 mL hydrochloric acid (conc.). The precipitate was separated, dried and recrystallized from toluene (700 mL), resulting in 2.17 g (60% yield) of the desired compound as colorless needles. $^1$H-NMR (THF-d$^8$, 300 MHz,) (ppm), 4.259 (s, 4H), 7.574 δ (t, 2H), 7.662 (t, 2H), 7.862 (d, 2H), 8.199 (d, 2H), 8.366 (s, 2H).

Example 2 illustrates the synthesis of 6,6,12,12-tetrakis(3-phenoxypropyl)-6,12-dihydroindeno[1,2-b]fluorine.

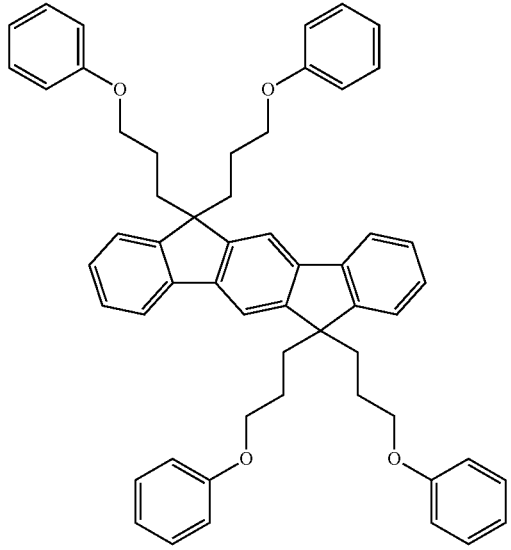

6,6,12,12-tetrakis(3-phenoxypropyl)-
6,12-dihydroindeno[1,2-b]fluorene

To a suspension of indenofluorene in Example 1 (1.5 g, 5.94 mmol) in THF (60 mL), n-BuLi (2.5 M in n-hexane, 7.1 mL, 17.8 mmol) was added via a syringe at −25° C. The solution was stirred at −25° C. for 15 min, then warmed up to room temperature for an additional hour and 3-phenoxypropyl bromide (3.828 g, 17.8 mmol) was added via a syringe at −25° C. After stirring for 4 h, the second portion of n-BuLi (2.5 M in n-hexane, 7.1 mL, 17.8 mmol) was added via a syringe at −25° C. After one hour, a second portion of 3-phenoxypropyl bromide (3.828 g, 17.8 mmol) was added via a syringe at −25° C. Then the mixture was kept stirring for 12 h before it was quenched with ammonium chloride solution and extracted with chloroform (3×50 mL). The organic layer was dried over anhydrous MgSO$_4$ and the solvent was removed under reduced pressure. The crude product was purified by column chromatography using silica gel and chloroform/petroleum ether as the eluent.

The desired product was obtained as a yellow solid (3.2 g, yield 61%). $^1$H NMR (DMSO-d6, 400 MHz, ppm): 7.95 (s, 2H), 7.87 (d, 2H), 7.50 (d, 2H), 7.38 (t, 2H), 7.33 (t, 2H), 7.11-7.13 (t, 8H), 6.77 (t, 4H), 6.77 (d, 8H), 3.64 (t, 8H), 2.11 (t, 8H), 1.05-1.09 (m, 8H).

Example 3 illustrates the synthesis of 6,6,12,12-tetrakis(3-bromopropyl)-6,12-dihydroindeno[1,2-b]fluorine.

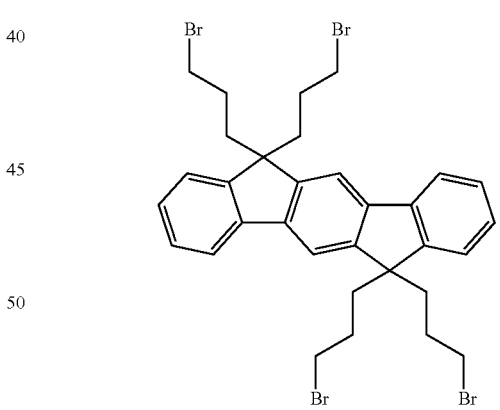

15 mL of HBr solution (48% in water by weight), 2.26 g of 6,6,12,12-tetrakis(3-phenoxypropyl)-6,12-dihydroindeno[1,2-b]fluorene (2.85 mmol), 100 mL of acetic acid, and 10 mL of toluene were added into a flask and heated at reflux for 48 h. The reaction mixture was poured into water, and the resulting solution was extracted with chloroform (3×50 mL). The combined organic layers were washed with dilute Na$_2$CO$_3$ (1 M, 2×50 mL) solution, water and dried over MgSO$_4$, then the solvent was removed, and the residual was purified by silica gel chromatography using petroleum ether/chloroform (3:1) as the eluent to get the compound (1.1 g, yield 56%) as a white solid. $^1$H NMR (CDCl$_3$, 400 MHz, ppm): 7.75 (d, J=7.6 Hz, 2H), 7.63 (s, 2H), 7.29-7.39 (m, 6H), 3.14 (t, J=8.0 Hz, 8H), 2.06 (t, J=8.0 Hz, 8H), 1.051.09 (m, 8H).

Example 4 illustrates the synthesis of 2,8-dibromo-6,6,12,12-tetrakis(3-bromopropyl)-6,12-dihydroindeno[1,2-b]fluorine.

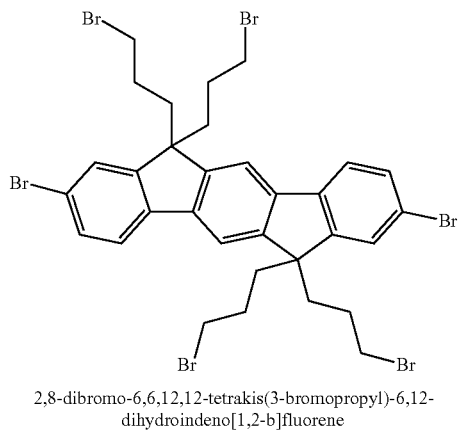 [SMILES: BrCCCC1(CCCBr)c2cc(Br)ccc2-c2cc3c(cc21)-c1ccc(Br)cc1C3(CCCBr)CCCBr]

2,8-dibromo-6,6,12,12-tetrakis(3-bromopropyl)-6,12-dihydroindeno[1,2-b]fluorene

To a solution of 6,6,12,12-tetrakis(3-bromopropyl)-6,12-dihydroindeno[1,2-b]fluorene (1.1 g, 1.39 mmol) in 80 mL of CH$_2$Cl$_2$ was added Br2 (0.851 g, 3.89 mmol). The mixture was stirred at room temperature for 18 h. Then, the solution mixture was washed by 2M Na$_2$CO$_3$. The organic solution was dried over MgSO$_4$. The removal of the solvent gave the crude product as a yellow solid. Recrystallization was carried out in a mixture of chloroform and methanol to afford 1.12 g of compound (91% yield). $^1$H NMR (DMSO, 400 MHz, ppm): 7.97 (s, 2H), 7.84 (d, 2H), 7.71 (2H), 7.57 (dd, 2H), 3.11-3.20 (t, 8H), 2.22 (m, 8H), 1.02-1.06 (m, 8H).

Example 5 illustrates the m-pegylation (poly(ethylene glycol) methyl ether (mPEG$_{550}$, HO-PEG$_{550}$-OCH$_3$) of 2,8-dibromo-6,6,12,12-tetrakis(3-bromopropyl)-6,12-dihydroindeno[1,2-b]fluorine (PaPeg)

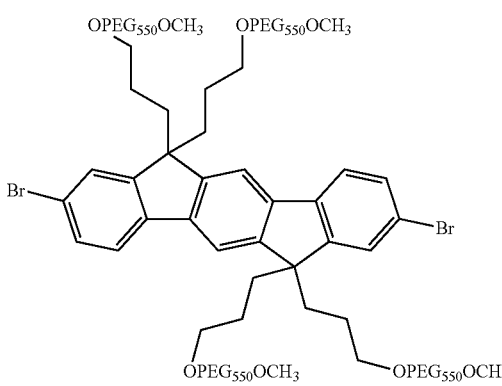

mPEG550 alcohol (HO-PEG$_{550}$-OCH$_3$) (3.331 g, 6.01 mmol) was dissolved in anhydrous THF (20 mL) at 0° C. under nitrogen. To the mixture, was added potassium tert-butoxide (7.74 mmol, 7.74 mL, 1M in THF). After 10 min stirring, 2,8-dibromo-6,6,12,12-tetrakis(3-bromopropyl)-6,12-dihydroindeno[1,2-b]fluorene (1.35 g, 1.50 mmol) in 20 mL of anhydrous THF was added via a syringe. The mixture was allowed to warm room temperature and stirred overnight. After evaporation of THF, brine (50 mL) was added and crude product was extracted with dichloromethane (3×40 mL). The combined organic layers were concentrated and purified by column chromatography (DCM-isopropanol) to give colorless oil product (2.164 g).

Example 6 illustrates the synthesis of 11,12-dihydroindeno[2,1-a]fluorine

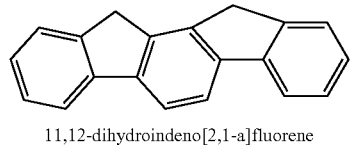 [SMILES: c1ccc2c(c1)Cc1c-2ccc2c1Cc1ccccc1-2]

11,12-dihydroindeno[2,1-a]fluorene

This compound can be made according to U.S. Pat. No. 7,754,841, incorporated herein by reference.

Example 7 illustrates the synthesis of 11,11,12,12-tetrakis (3-phenoxypropyl)-11,12-dihydroindeno[2,1-a]fluorine.

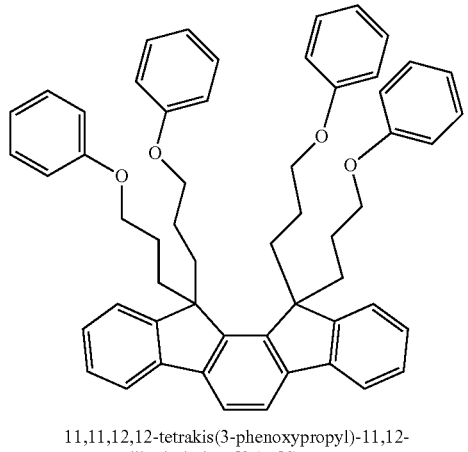

11,11,12,12-tetrakis(3-phenoxypropyl)-11,12-dihydroindeno[2,1-a]fluorene

The compound is made similarly to the Example 2 while 11,12-dihydroindeno[2,1-a]fluorine in Example 6 was used as starting materials.

Example 8 illustrates the synthesis of 11,11,12,12-tetrakis (3-bromopropyl)-11,12-dihydroindeno[2,1-a]fluorine.

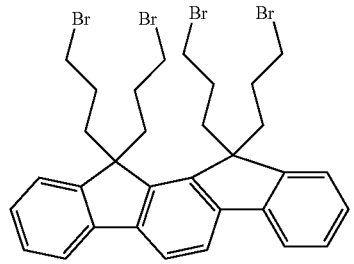

11,11,12,12-tetrakis(3-bromopropyl)-11,12-dihydroindeno[2,1-a]fluorene

The compound is made similarly to Example 3 while 11,11,12,12-tetrakis(3-phenoxypropyl)-11,12-dihydroindeno[2,1-a]fluorine in example 7 was used as starting materials.

Example 9 illustrates the synthesis of 2,9-dibromo-11,11,12,12-tetrakis(3-bromopropyl)-11,12-dihydroindeno[2,1-a]fluorine.

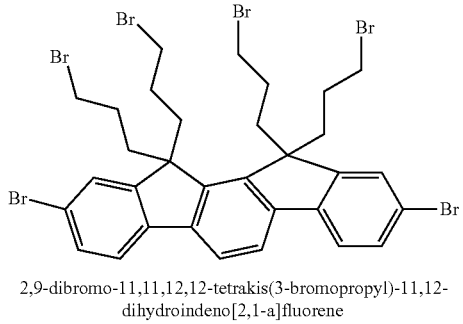 [SMILES: BrCCCC1(CCCBr)c2cc(Br)ccc2-c2ccc3c(c21)C(CCCBr)(CCCBr)c1cc(Br)ccc1-3]

2,9-dibromo-11,11,12,12-tetrakis(3-bromopropyl)-11,12-dihydroindeno[2,1-a]fluorene The compound is made similarly to example 4 while 11,11,12,12-tetrakis(3-bromopropyl)-11,12-dihydroindeno[2,1-a]fluorine in example 8 was used as starting materials.

Example 10 illustrates the m-pegylation (poly(ethylene glycol) methyl ether (mPEG$_{11}$,) of 2,9-dibromo-11,11,12,12-tetrakis(3-bromopropyl)-11,12-dihydroindeno[2,1-a]fluorine.

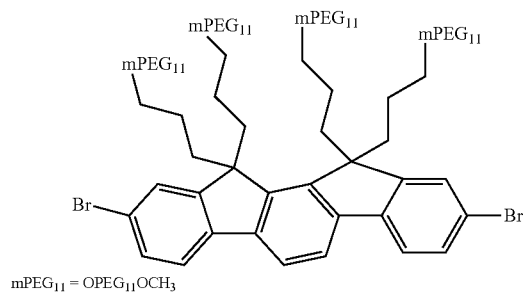

mPEG$_{11}$ = OPEG$_{11}$OCH$_3$

The compound is made similarly to example 5 while 2,9-dibromo-11,11,12,12-tetrakis(3-bromopropyl)-11,12-dihydroindeno[2,1-a]fluorine in example 9 and mPEG$_{11}$-OH was used as starting materials.

Example 11 illustrates the synthesis of 2,2'-(6,6,12,12-tetrakis(3-bromopropyl)-6,12-dihydroindeno[1,2-b]fluorene-2,8-diyl)bis(4,4,5,5-tetramethyl-1,3,2-dioxaborolane). (TBpeg550)

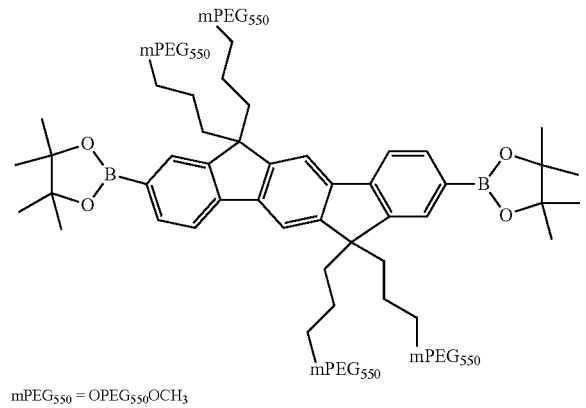

mPEG$_{550}$ = OPEG$_{550}$OCH$_3$

A mixture of the product in example 5 (0.943 g, 0.34 mmol), bis (pinacolato) diboron (190 mg, 0.75 mmol), [1,1'-bis(diphenylphosphino) ferrocene] dichloropalladium (97 mg, 0.12 mmol) and potassium acetate (200 mg, 2.0 mmol) in anhydrous dioxane (12 mL) was heated under reflux for 18 h under Ar atmosphere. After the reaction mixture was cooled down to room temperature, the solid was removed by filtration, and the filtrate was concentrated under vacuum. The resulting crude product was purified by column chromatography eluting with 10% methanol in dichloromethane to give product as oil.

Example 12 illustrates the synthesis of 2,2'-(6,6,12,12-tetrakis(3-bromopropyl)-6,12-dihydroindeno[1,2-b]fluorene-2,8-diyl)bis(4,4,5,5-tetramethyl-1,3,2-dioxaborolane). (CBPeg11)

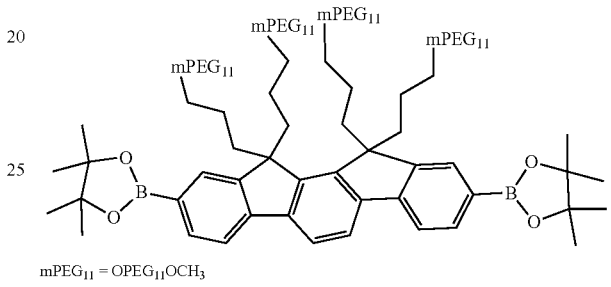

mPEG$_{11}$ = OPEG$_{11}$OCH$_3$

The compound is made similarly as described in Example 11.

Example 13 illustrates the synthesis of 2',7'-dibromo-3,3-bis(bromomethyl) spiro [cyclobutane-1,9'-fluorene]

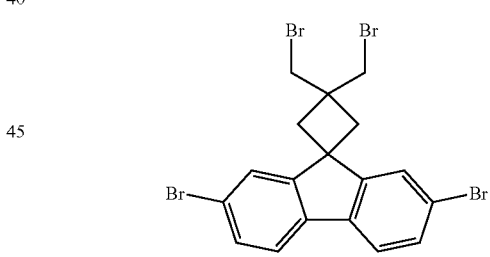

To a mixture of 2,7-dibromo fluorene (3.26 g, 10 mmol) in 50 ml anhydrous THF in a 250 ml three-necked flask under Ar protection, NaH (0.6 g, 25 mmol) NaH flask was added over 30 min. The mixture was stirred at room temperature 30 min, pentaerythrityl bromide (3.87 g, 10 mmol) of in 20 ml anhydrous THF were then dropped to the flask. The mixture was heated at 70° C. overnight. After the reaction was completed, the mixed solution was quenched by ice H$_2$O, then extracted three times with CH$_2$Cl$_2$, and the CH$_2$Cl$_2$ solution was dried over anhydrous magnesium sulfate, and filtered. The filtrate was rotary evaporated to give a brown solid, the solid was separated by column chromatograph to afford the yellow solid.

Example 14 illustrates the synthesis of 2,6-diamino(Boc)-1-(2,7-dibromospiro[fluorene-9,4'-piperidin]-yl)hexan-1-one. (MBoc):

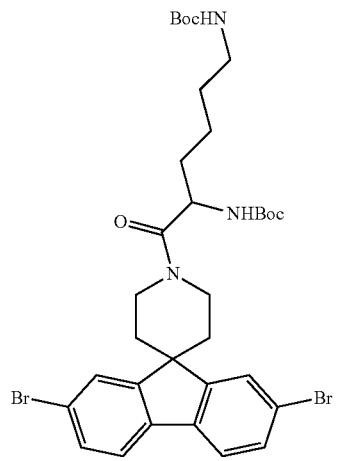 [SMILES: CC(C)(C)OC(=O)NCCCCC(NC(=O)OC(C)(C)C)C(=O)N1CCC2(CC1)c1cc(Br)ccc1-c1ccc(Br)cc12]

The starting material 2,7-dibromo-1-methyl-spiro[fluorene-9,4'-piperidine] was made according to U.S. Pat. Pub. No. 2014/0243283, incorporated herein by reference.

The mixture of (Boc-Lys(Boc)-OH (6.6 g, 18 mmol) and triethylamine (5.1 ml, 36 mmol) in 100 ml of CH$_2$Cl$_2$ is cooled to 0° C., then EDC-HCl salt (3.43 g, 18 mmol) was added, the mixture was stirred for 20 min, 2,7-dibromo-1-methyl-spiro[fluorene-9,4'-piperidine] (5.0 g, 12 mmol) was added and the mixture was stirred for 16 h at room temperature. To the reaction mixture 100 ml of CH$_2$Cl$_2$ and 100 ml of water were added. The phases were separated and aqueous phase is again extracted with 100 ml of CH$_2$Cl$_2$. Collected organic phases were washed with water (200 ml×2). The organic phase was evaporated to dryness and separated by hexane/EtOAc to afford white cotton solid 8.21 g (yield 95%).

Example 15 illustrates the synthesis of 2',7'-dibromo-3,3-bis(O-PEG550 methyl ether)spiro[cyclobutane-1,9'-fluorene] (SqPeg).

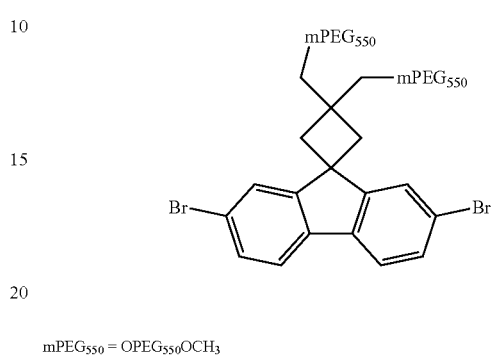

mPEG$_{550}$ = OPEG$_{550}$OCH$_3$ mPEG550 alcohol (HO-PEG$_{550}$-OCH$_3$) (3.331 g) was dissolved in anhydrous THF (20 mL) at 0° C., under nitrogen. To the mixture, was added potassium tert-butoxide (7.74 mmol, 7.74 mL, 1M in THF). After 10 min stirring, 2',7'-dibromo-3,3-bis(bromomethyl) spiro[cyclobutane-1,9'-fluorene] (1.45 g, 2.579 mmol) in 20 mL of anhydrous THF was added via a syringe. The mixture was allowed to warm room temperature and stirred overnight. After evaporation of THF, brine (50 mL) was added and crude product was extracted with dichloromethane (3×40 mL). The combined organic layers were concentrated and purified by column chromatography (DCM-isopropanol) to give colorless oil product (2.164 g).

Example 16 illustrates a synthetic scheme for a macromer P14 of the present disclosure.

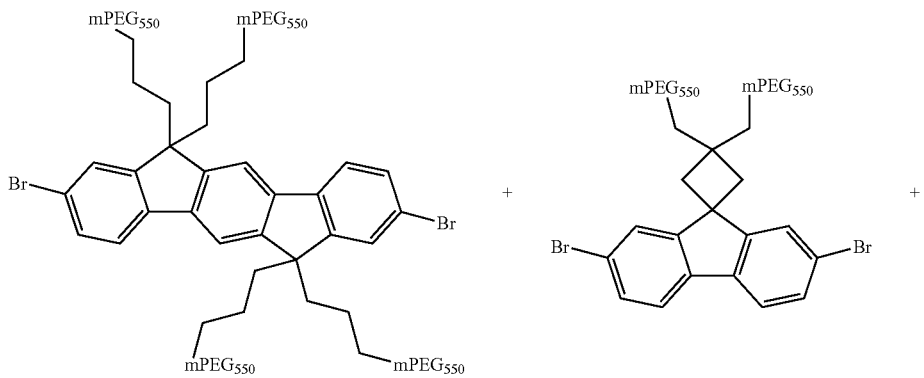

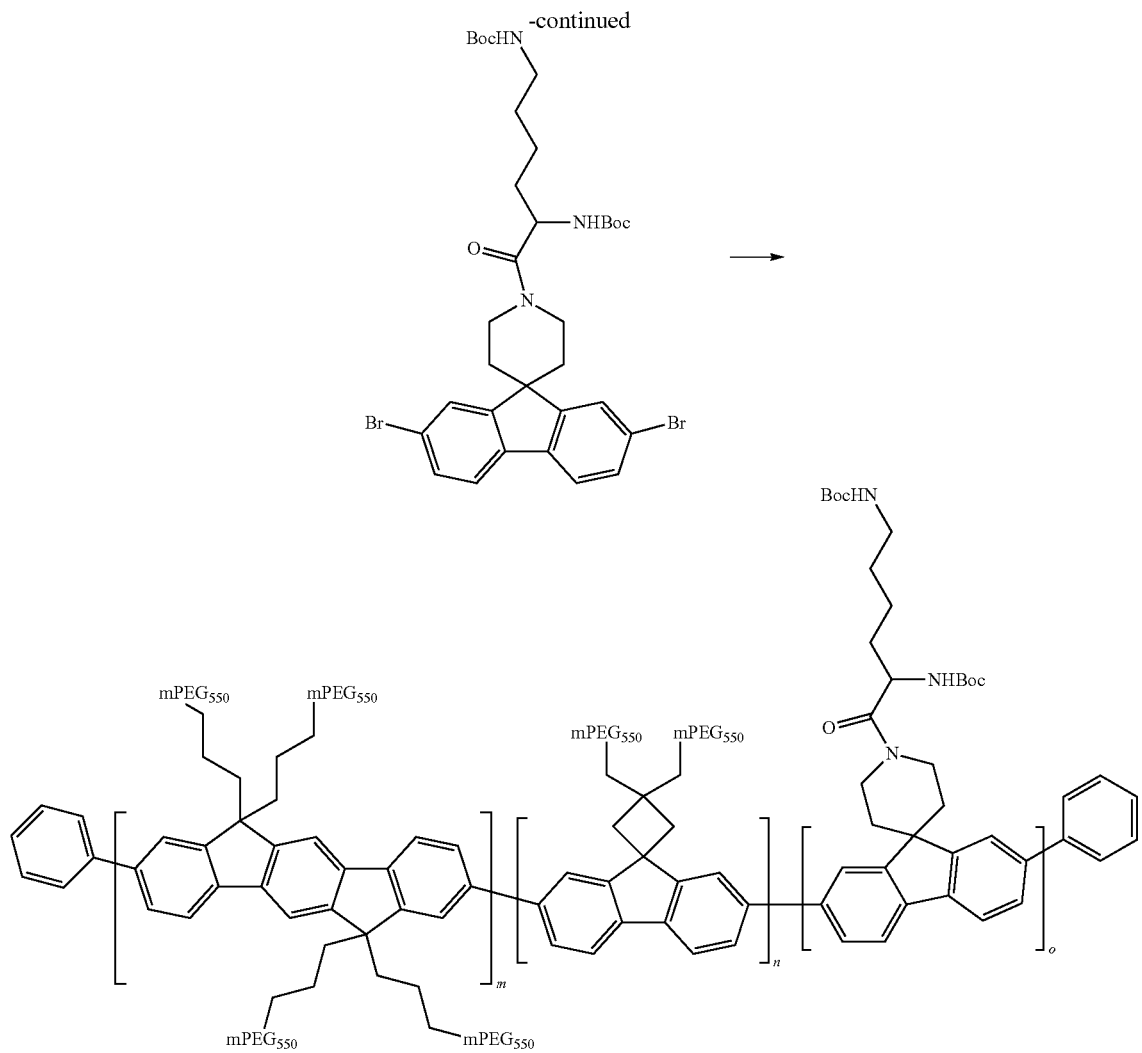

To a stirred solution of Ni(COD)$_2$ (552 mg, 2.0 mmol) and 2,2'-bipyridine (314 mg, 2.0 mmol) in dry DMF (35 ml) was added COD (246 μl, 2.0 mmol) and the resultant solution was stirred for 1 h at 75° C. under nitrogen. 2,6-diamino (Boc)-1-(2,7-dibromospiro[fluorene-9,4'-piperidin]-r-yl) hexan-1-one (72 mg, 0.01 mmol) and 2',7'-dibromo-3,3-bis (O-PEG550 methyl ether)spiro[cyclobutane-1,9'-fluorene] (0.551, 0.40 mmol), monomer PaPeg (1.388 g, 0.50 mmol) were dissolved in DMF (6 ml) in a separation flask under nitrogen and then added to the mixture. The mixture was stirred overnight for 24 h at 75° C. under nitrogen. Bromobenzene (95 ul, 0.91 mmol) was added to the mixture and stirred for 12 h under the same conditions. The mixture was dropped slowly by pipette into a stirred solvent 150 ml 6N HCl and the resultant mixture was stirred for 2 h. The mixture was exacted by DCM and organic layer was washed with 50 ml 1N HCl. The solvent was evaporated off and further dried under high vacuum to give a light wax polymer P14. (820 mg), GPC ($M_n$=73,000; PDI=2.2).

The polymer P14 above compound were then dissolved in 30 ml DCM and 30 ml TFA mixture, then stirred at room temperature overnight. The solvent was removed under reduced pressure and then dried down under high vacuum pump overnight. This polymer needs further purification before labelling. For purification, the dried polymer was resuspended in DI water and kept under stirring overnight. Most of polymer was dissolved, the undissolved precipitates were removed by centrifugation at 10,000 rpm for 5 min. the supernatant was filtered by 0.22 um PES filter and concentrated by Amicon® Ultra-4 Centrifugal Filter Units (MWCO, 30K) (available from EMD Millipore Corporation, Billerica, Mass.). Then this solution was loaded to G-25 column (Sephadex G-25 Fine, GE Healthcare Life Sciences) to remove catalyst impurities. The purified polymer was further fractionated by flowing through a Superose 6 column (GE Life Sciences) to narrow down size distribution.

A series of novel copolymers consisted of monomer peglated fluorene (SqPeg) and different content of peglated indenofluorene segments were synthesized by Yamamoto and Suzuki method. Their Mn ranges from 20K to 85K. As mentioned before, Yamamoto reaction forms random copolymer while Suzuki makes alternate copolymer. The example absorption data of the polymers with exact content ratio of SqPeg and peglated indenofluorene segments and Mn are shown in FIGS. 13 and 14.

Figure 13:
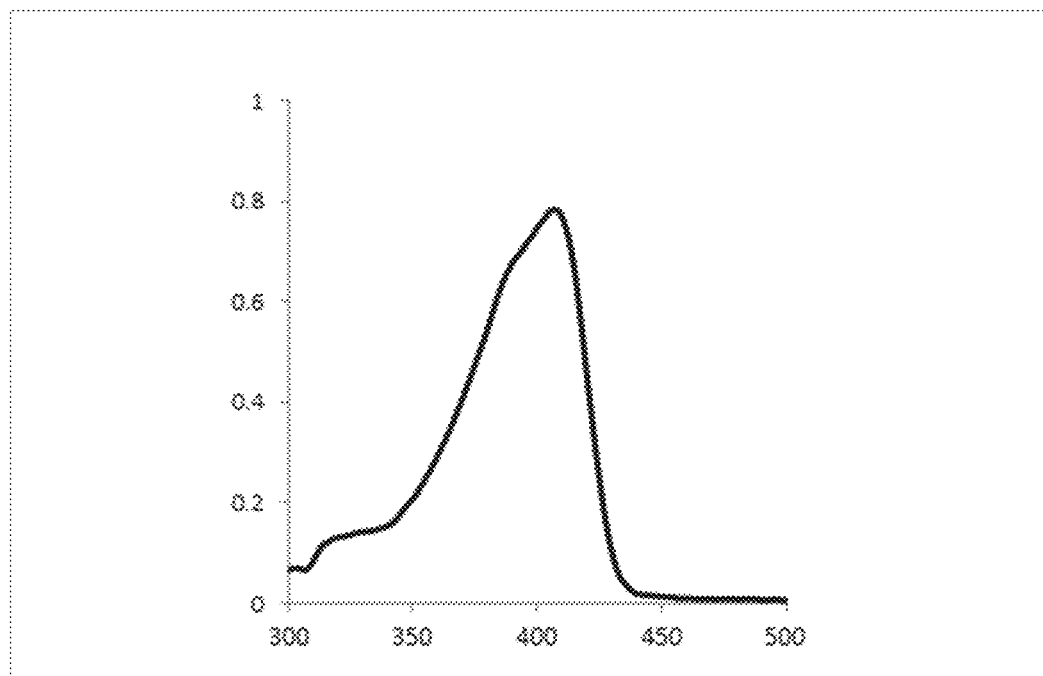
FIG. 13 shows an absorption curve of a macromer (L18) of the present disclosure.
Figure 14:
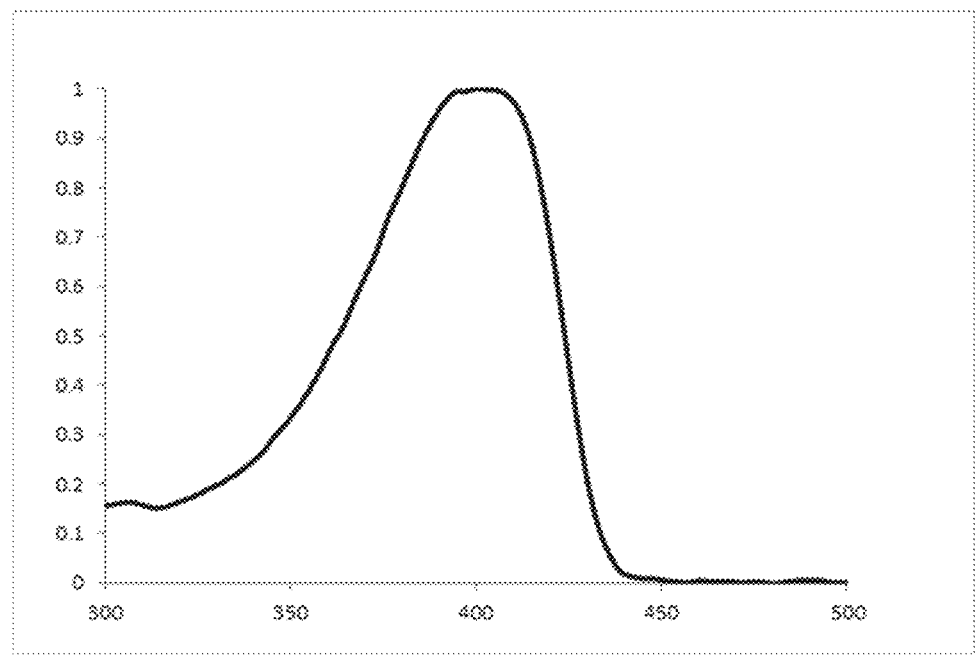
FIG. 14 shows an absorption curve of a macromer (P100) of the present disclosure.

FIG. 13 represents the absorption curve of polymer L18 made by Suzuki polymerization while FIG. 14 represents the absorption curve of polymer P100 made by Yamamoto polymerization. In both cases, the Indenofluorene monomer does cause both an absorption and emission red shift Indenofluorene has similar lowest energy transitions that can be attributed to a π-π* transition with λmax values in the 363-400 nm range and exhibit blue emission. More information is shown in Table 1.

TABLE 1

| Polymer | SqPeg | PatPeg | MBoc | MW (M$_n$) | λmax Abs. (nm) | λmax Em. (nm) | Synthesis method Yamamoto(Y) Suzuki(S) |
|---|---|---|---|---|---|---|---|
| P114 | Yes | No | No | 45K | 394 | 421 | Y |
| P111 | Yes | No | No | 36K | 393 | 421 | Y |
| P100 | Yes | Yes | Yes | 32K | 400 | 429 | Y |
| P102 | Yes | Yes | No | 30K | 405 | 430 | Y |
| P151 | Yes | Yes | Yes | 55K | 405 | 430 | Y |

TABLE 1-continued

| Polymer | SqPeg | PatPeg | MBoc | MW (M$_n$) | λmax Abs. (nm) | λmax Em. (nm) | Synthesis method Yamamoto(Y) Suzuki(S) |
|---|---|---|---|---|---|---|---|
| P14 | Yes | Yes | Yes | 73K | 411 | 430 | Y |
| P43 | Yes | Yes | Yes | 33K | 395 | 430 | Y |
| L18 | Yes | Yes | No | 33K | 405 | 425 | S |

Gel permeation chromatography (GPC) was carried out in THF at 50° C. using a 5 μm WatersStyragel® HR3 and a HR4 GPC column system on a Agilent 1200 HPLC Separations Module with a Agilent UV Detector using a flow rate of 0.5 mL/min. The system was calibrated with Agilent's EasiCal PS-2 standards in range of 580 to 364,000 g/mol.

Example 17 illustrates m-pegylation of 2,5-dibromohydroquinone (BPeg11)

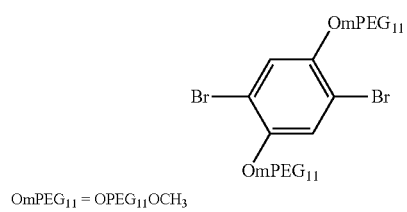

The compound is made using 2,5-dibromohydroquinone and mPEG$_{11}$-iodo was used as starting materials.

Example 18 illustrates m-pegylation of 1,4-Dibromo-2,5-bis(bromomethyl)benzene (Bpeg550).

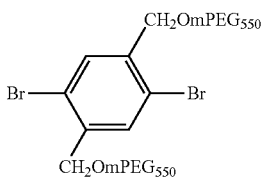

The compound was made similarly to example 15 while 1,4-dibromo-2,5-bis(bromomethyl)benzene and mPEG$_{550}$-OH was used as starting materials.

Example 19 illustrates the synthesis of a macromer of this disclosure.

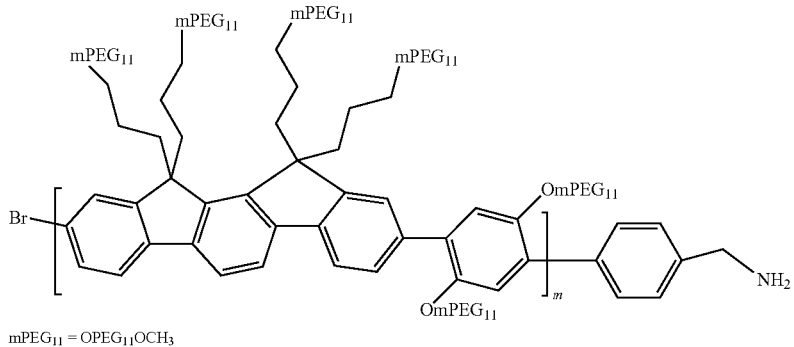

Under the argon, to the solution of CBPeg11 in example 12 (0.273 g, 1 mmol) and BPeg11 in example 17 (0.130 g, 1.1 mmol) in DMF (6 mL) in a Schlenk flask, K$_2$CO$_3$ in water (2 M, 4 mL) was added, followed by palladium tetrakis(triphenylphosphine) (12 mg, 0.012 mmol). The mixture was degassed via three freeze-pump-thaw cycles and then heated to 80° C. for 12 hours, then 4-(N-Boc-aminomethyl)phenylboronic pinacol ester (50 mg) was added, the mixture was reheated for 5 h at 80° C. At room temperature, to the reaction mixture EDTA (100 mg, 0.33 mmol) in 20% EtOH/H$_2$O (20 mL) was added and stirred at room temperature for 1 hour. The resulting mixture was then filtered through a 0.45 m cup filter. The filtered solution was diluted to the concentration of 2 mg/mL using 20% EtOH/H$_2$O. The resulting dilution was then dialyzed into 20% EtOH/H2O using a tangential flow filtration system with 30,000 kD molecular weight cutoff membrane until there was less than 0.1 mg/mL of polymer in the elutant. The solution was concentrated and lyophilized to give a yellow, fibrous solid polymer P15 (0.41 g). Molecular weight was determined by SEC analysis relative to polystyrene standard (MW=65,000, D=2.0).

The polymer 15 was treated similarly as polymer P14 above in the Example 17, and then was used for activation and further bio-conjugation.

Example 20 illustrates the synthesis of a macromer of this disclosure.

The compound is made similarly to Example 19 while the TBpeg550 in example 11 and the Bpeg550 in Example 18 were used as starting materials. Absorption at 350 nm, emission at 409 nm in PBS.

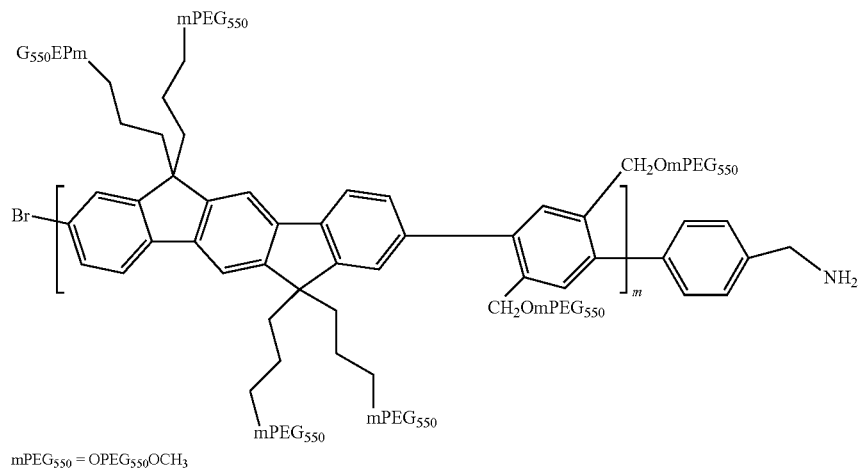

mPEG$_{550}$ = OPEG$_{550}$OCH$_3$

Example 21 Conjugation of Polymer Dyes (compound P14) to Antibodies

A method for conjugation of antibodies to polymer dye is described. Mouse monoclonal antibody against human CD4 (UCHT1) or anti-human IFN-γ Antibody (4S.B3) were used for conjugation. The antibodies solution (5 mg/ml in PBS, pH7.2) were reduced by DTT activation (Dithiothreitol) at a molar ratio of 160:1 for 30 min. They were purified and buffer-exchanged to 50 mM Phosphate, 5 mM EDTA pH7.0 by G-25 column (Sephadex G-25 Fine, GE Healthcare Life Sciences). The polymer dyes in 50 mM Phosphate, 5 mM EDTA pH7.0 were activated by 25× molar excess of Sulfo-SMCC (sulfosuccinimidyl 4-(N-maleimidomethyl)cyclohexane-1-carboxylate, Cova Chem) for 2 hours. Then the free Sulfo-SMCC reagents were removed by G-25 column. For conjugation, the DTT-reduced antibody was mixed with SMCC-activated polymer dyes at 4:1 molar ratio for 18-20 hours. After purifying with Protein G resin, the conjugates are separated from free antibody by Superose 6 (GE Life Sciences) and concentrated by centrifugal filters (30K Mw cut-off, Millipore). These antibody-polymer conjugates were evaluated by flow cytometry.

Example 22 Lysed Washed Blood (LWB Staining)

100 μL of anti-coagulated whole blood was added to tubes containing fluorophore conjugated antibodies and gently mixed. The tubes were incubated at room temperature in the dark for 15 minutes, followed by addition of 2 mL of room temperature 1×RBC Lysis Buffer (BioLegend, Inc.) directly to the mixture. Tubes were incubated at room temperature in the dark for 15 minutes, followed by centrifugation at 1200-1500 rpm for 5 minutes to pellet the cells. Supernatants were removed, the tubes gently vortexed to loosen the cell pellets and 2 mL of FACS Wash Buffer (BioLegend, Inc) was added. Tubes were centrifuged at 1200-1500 rpm for 5 minutes, the supernatants were aspirated, and the tubes were again vortexed to loosen the pellets. Cells were resuspended from the pellet by adding 300-500 μL of 1% paraformaldehyde in 1×PBS with NaN$_3$, pH 7.2 to each FACS tube. Cells were then ready for analysis by flow cytometry. Sample signal to noise (S/N) calculations are derived from mean fluorescence intensity (MFI) of the positively stained population divided by the MFI of the unstained population. Stain Index (SI) calculations are derived from mean fluorescence intensity (MFI) of the positively stained population minus the MFI of the negatively stained population, divided by two times the robust standard deviation of the negatively stained population. Flow cytometric analyses were performed with a BD LSR II instrument equipped with 355 nm Ultraviolet, 405 nm Violet, 488 nm Blue, 532 nm Green, and 640 nm Red excitation laser sources. Lymphocytes were gated based on their forward (FSC) and side scatter (SSC) profiles. The results show the polymeric fluorophore P43 or P100 be can be used to successfully identify the CD3+(UCHT1+) cells present in a complex heterogeneous mixture of cells such as the LWB preparation, as compared to the Pacific Blue™ control.

Results

Figure 11A:
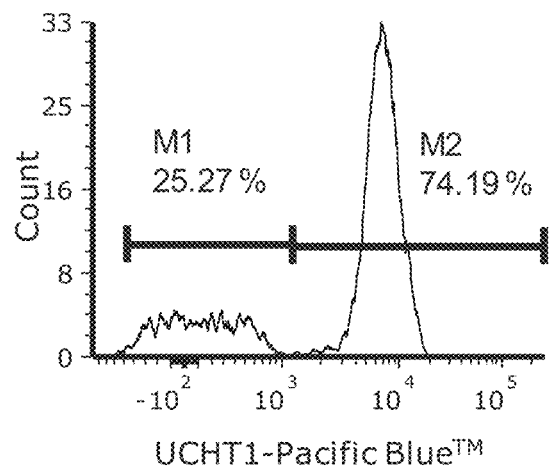
FIGS. 11A-C show CD3 Staining of Lysed Washed Blood (LWB), gated on Lymphocytes: 0.5 μg.
Figure 11B:
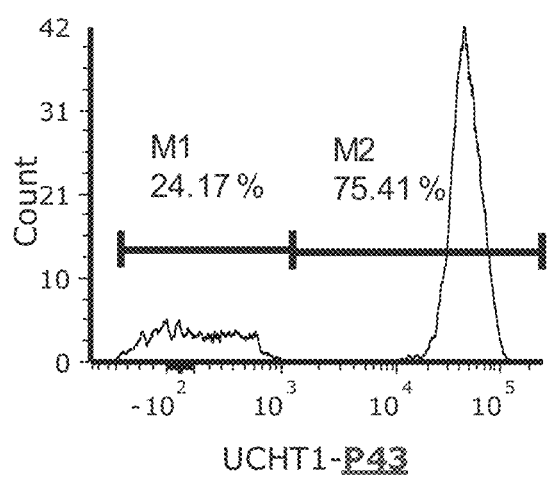
Figure 11C:
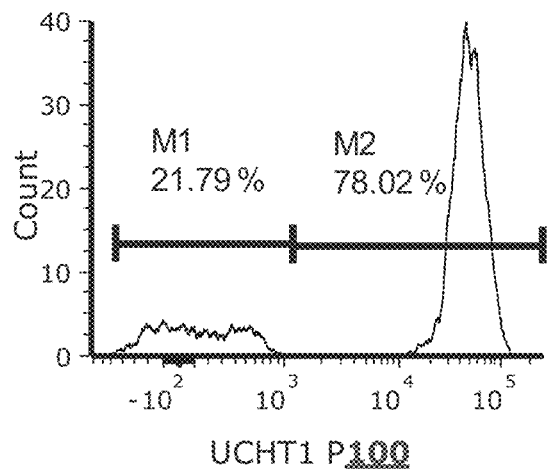

Cell surface flow cytometric analysis of human Lysed Washed Blood samples stained with P43 or P100 polymer fluorophore conjugated to anti-CD3 antibody. Human Lysed Washed Blood (LWB) samples were stained with 0.5 μg/test of P43 or P100 polymer fluorophore conjugated to the UCHT1 monoclonal antibody. Flow cytometric analyses were performed with a BD LSR II instrument equipped with 355 nm Ultraviolet, 405 nm Violet, 488 nm Blue, 532 nm Green, and 640 nm Red excitation laser sources. Lymphocytes were gated based on their forward (FSC) and side scatter (SSC) profiles. The results show the polymeric fluorophore P43 (FIG. 11B) or P100 (FIG. 11C) be can be used to successfully identify the CD3+(UCHT1+) cells present in a complex heterogeneous mixture of cells such as the LWB preparation, as compared to the Pacific Blue™ control (FIG. 11A). The percentages indicate the relative frequency of the negatively stained cell populations (M1) and the positively stained cell populations (M2).

Example 23 illustrates PBMC isolation

Human peripheral blood mononuclear cells (PBMCs) were isolated through a gradient of Ficoll-Paque PLUS (GE Healthcare) according the instructions of manufacturer. Cells were suspended in FACS Wash Buffer (BioLegend) and counted. Cells were centrifuged at 1200-1500 rpm for five minutes and the wash supernatant removed. The cell pellet was loosened by gentle mixing and cells were then resuspended in 3 mL of 4% Paraformaldehyde fixation buffer while vortexing. Cells were allowed to fix at room temperature in the dark for 20 minutes. Cells were washed twice with 1× Permeabilization Buffer (BioLegend) by pelleting the cells at 1200-1500 rpm for 5 minutes, removing the supernatant, and vortexing to loosen the pellet. Cell density was adjusted to 5 million to 10 million cells/mL with 1× Permeabilization Buffer. 100 μL cell suspension was added into the tubes containing dilutions of appropriate antibodies to CD3 and to Perforin (clone dG9). Cells were incubated in dark at room temperature for 20-30 minutes, followed by twice washing procedure with FACS Wash Buffer. Cells were resuspended in 500 μL FACS Wash Buffer and analyzed by Flow Cytometry. Flow cytometric analyses were performed with a BD LSR II instrument equipped with 355 nm Ultraviolet, 405 nm Violet, 488 nm Blue, 532 nm Green, and 640 nm Red excitation laser sources. Lymphocytes were gated based on their forward (FSC) and side scatter (SSC) profiles. The results show the polymeric fluorophore P43 or P100 can be used to successfully identify the Perforin (clone dG9+) cells present in a complex heterogeneous mixture of cells such as the PBMCs, as compared to the Pacific Blue™ control.

Results

Figure 12A:
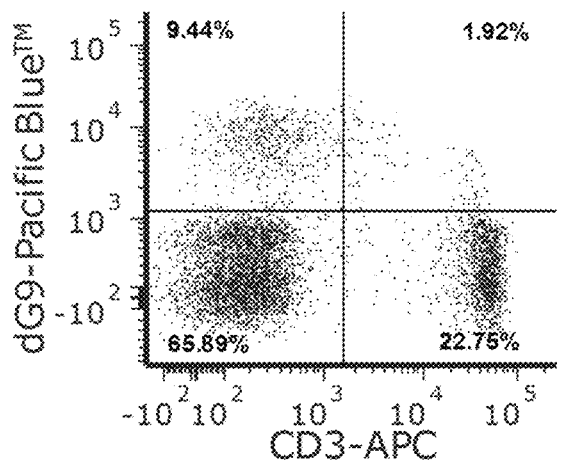
FIGS. 12A-C show Perforin Staining of Peripheral Blood Mononuclear Cells (PBMCs), gated on Lymphocytes.
Figure 12B:
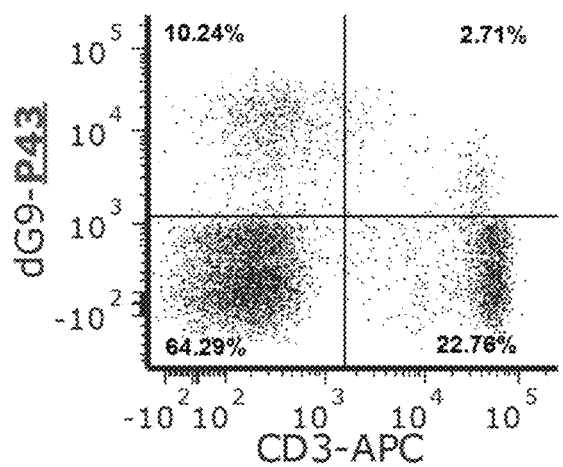
Figure 12C:
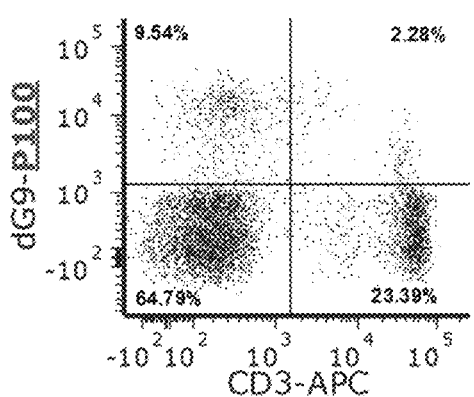

Intracellular flow cytometric analysis of Perforin (clone dG9) with P43 or P100 polymer fluorophore conjugated to anti-Perforin antibody. Conjugated antibody was used to stain intracellular Perforin human peripheral blood mononuclear cell (PBMC) samples. Samples were also surface stained with allophycocyanin (APC)-conjugated anti-CD3 antibody to simultaneously identify T cells. Conjugated anti-Perforin antibody was used at 0.25 ug/test. Flow cytometric analyses were performed with a BD LSR II instrument equipped with 355 nm Ultraviolet, 405 nm Violet, 488 nm Blue, 532 nm Green, and 640 nm Red excitation laser sources. Lymphocytes were gated based on their forward (FSC) and side scatter (SSC) profiles. Data is plotted as Perforin on the ordinate and CD3 on the abscissa. The results show that the P43 (FIG. 12B) or P100 (FIG. 12C) polymer fluorophore can be used in an intracellular staining protocol in a complex heterogeneous mixture of cells such as the PBMCs, in concert with a surface staining antibody conjugated with a different fluorophore to identify Perforin producing CD3+ T cells, as compared to the Pacific Blue™ control (FIG. 12A). The percentages indicate the relative frequency of each population within the quadrants.

Example 24 illustrates the synthesis of 2',8'-dibromo-3,3, 3",3"-tetrakis(bromomethyl)dispiro[cyclobutane-1,6'-indeno[1,2-b]fluorene-12',1"-cyclobutane].

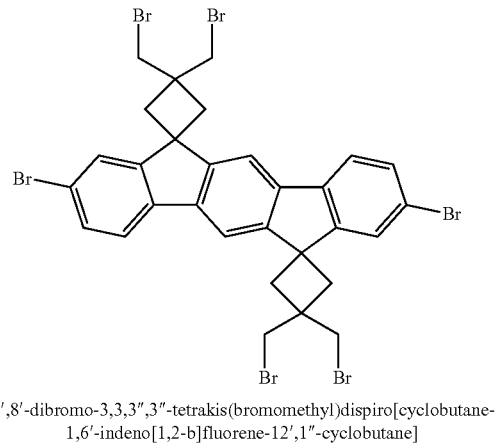

2',8'-dibromo-3,3,3",3"-tetrakis(bromomethyl)dispiro[cyclobutane-1,6'-indeno[1,2-b]fluorene-12',1"-cyclobutane]

The foregoing compound can be made in a similar manner according to Example 2, 3 and 4 above.

Example 25 illustrates the synthesis of 2',9'-dibromo-3,3, 3",3"-tetrakis(bromomethyl)dispiro[cyclobutane-1,11'-indeno[2,1-a]fluorene-12',1"-cyclobutane].

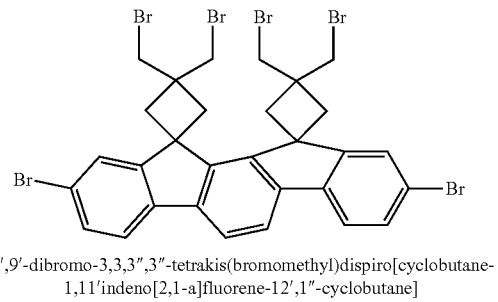

2',9'-dibromo-3,3,3",3"-tetrakis(bromomethyl)dispiro[cyclobutane-1,11'indeno[2,1-a]fluorene-12',1"-cyclobutane]

The foregoing compound can be made in a similar manner according to Example 2, 3 and 4 above.

Example 26 illustrates the pegylation of the compound in example 25.

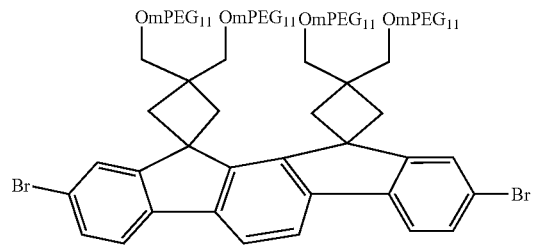

The compound can be made in a manner similar to the process according to Example 10.

Example 27 illustrates the pegylation of the compound in example 24.

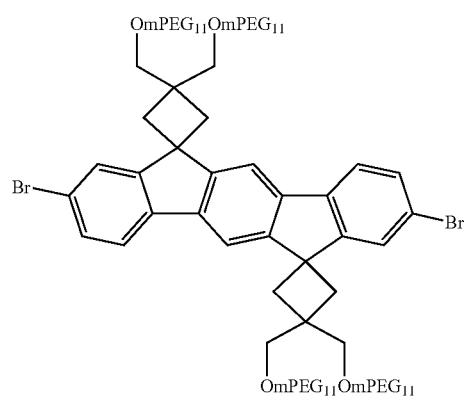

The compound can be made in a manner similar to the process according to Example 10.

All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes.

What is claimed is:

1. A macromer of formula I or formula II:

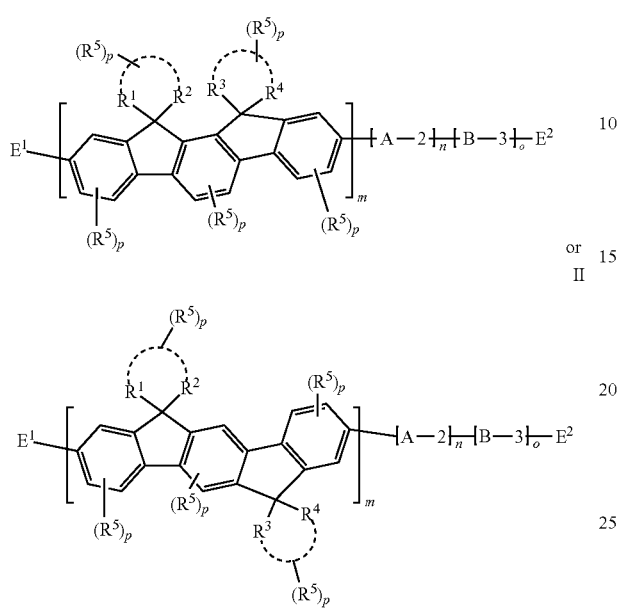

wherein each of $R^1$, $R^2$, $R^3$ and $R^4$ are each independently a member selected from the group consisting of hydrogen, an optionally substituted $C_1$-$C_{10}$ alkyl, an optionally substituted $C_1$-$C_{18}$ alkoxy, optionally substituted $C_6$-$C_{18}$ aryl, optionally substituted $C_4$-$C_{18}$ acyl, optionally substituted $C_4$-$C_{18}$ acyloxy, $NR^aR^b$, wherein $R^a$ and $R^b$ are each independently hydrogen or lower alkyl, a water soluble group, ethylene oxide oligomers and an ethylene oxide oligomer methyl ether;

alternatively, $R^1$ and $R^2$ and/or $R^3$ and $R^4$ together with the carbons to which they are attached, join to form a an optionally substituted 4-, 5-, or 6-membered ring;

each $R^5$ is independently a member selected from the group consisting of halo, alkyl, alkoxy, amino, ethylene oxide oligomers and an ethylene oxide oligomer methyl ether;

each p is a value from 0-3;

m is a value selected from the group consisting of 1-10,000, with the proviso that the macromer of Formula I or Formula II contains at least one indenofluorene monomer, wherein p=0 and each of $R^1$, $R^2$, $R^3$ and $R^4$ is $CH_2CH_2CH_2R^6$, wherein $R^6$ is a water-solubilizing group selected from the group consisting of an ethylene oxide oligomer and an ethylene oxide oligomer methyl ether;

each of A and B, can be present or absent and can each be the same or different, and each is selected from the group consisting of an aromatic group or heteroaromatic group, which group completes a 7-conjugated backbone;

each of 1, 2 and 3 can be present or absent and can each be the same or different, and each is selected from the group consisting of an aromatic group or heteroaromatic group, which group completes a 7-conjugated backbone;

n and o are each independently a value selected from the group consisting of 0-10,000, wherein the monomers within m, n, and o may be the same or different;

E1 and E2 are each independently a member selected from the group consisting of hydrogen, halogen, alkynyl, optionally substituted aryl, optionally substituted heteroaryl, halo, substituted aryl, boronic acid substituted aryl, boronic ester substituted aryl, boronic ester, boronic acid, optionally substituted fluorene and aryl or heteroaryl substituted with one or more pendant chains terminated with: i) a functional group selected from amine, carbamate, carboxylic acid, carboxylate, maleimide, activated esters, N-hydroxysuccinimidyl, hydrazines, hydrazids, hydrazones, azide, alkyne, aldehydes, thiols, and protected groups thereof for conjugation to a molecule or biomolecule; or ii) a conjugated organic dye or biomolecule; and wherein the macromer of Formula I or II can be an alternating copolymer, a block copolymer, a random copolymer or a graph copolymer between E1 and E2.

2. The macromer of claim 1, wherein the macromer has formula I-a or formula II-a:

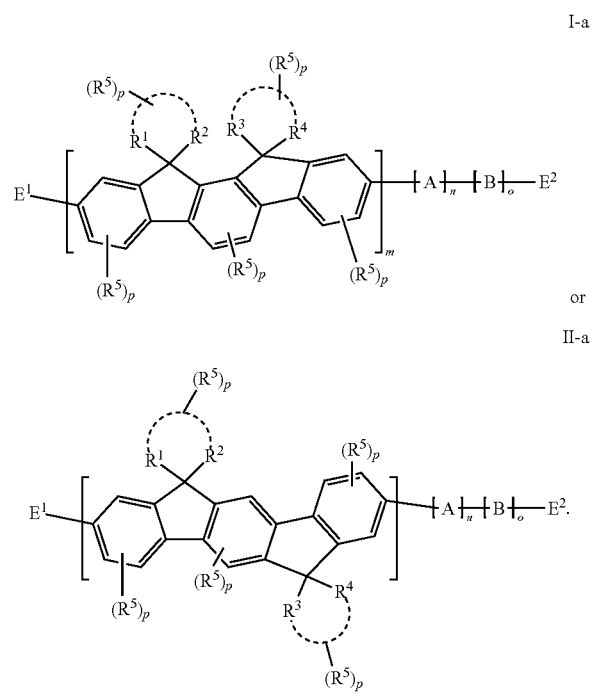

3. The macromer of claim 1, wherein the compound has the formula:

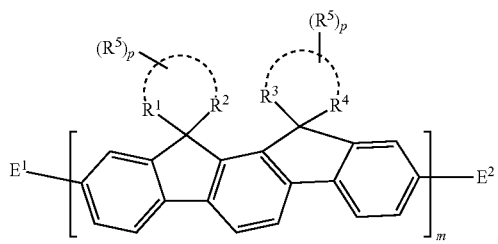

4. The macromer of claim 1, wherein the compound is of the formula:

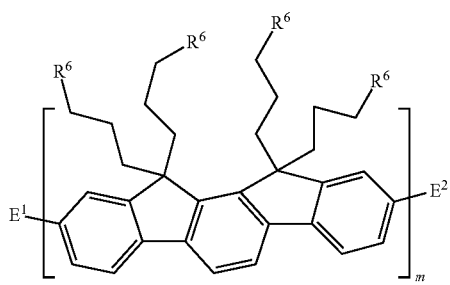

wherein each $R^6$ is an ethylene oxide oligomer methyl ether.

5. The macromer of claim 1, wherein the ethylene oxide oligomer methyl ether is —O—$PEG_{11}$-$OCH_3$ or —O—$PEG_{550}$-$OCH_3$.

6. The macromer of claim 1, wherein the compound has the formula:

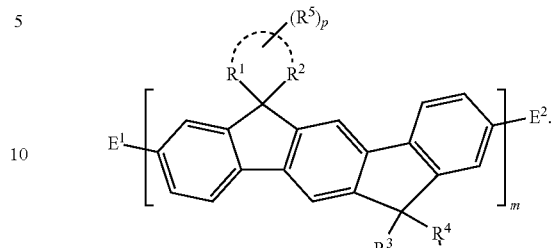

7. The macromer of claim 1, wherein the compound is of the formula:

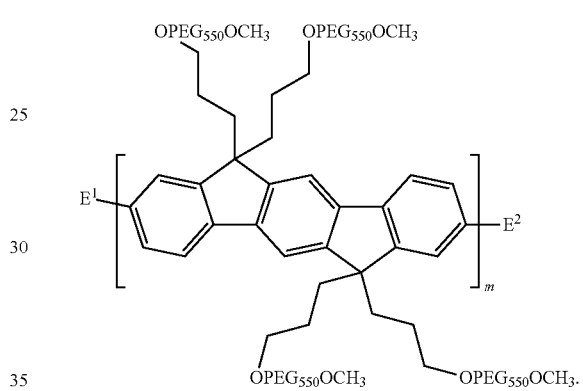

8. The macromer of claim 1, wherein the compound is of the formula:

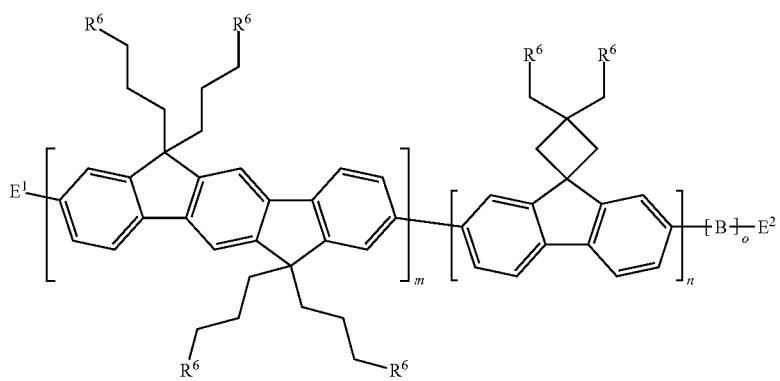

wherein each $R^6$ is independently a water-solubilizing group.

9. The macromer of claim 1, wherein the compound is of the formula:
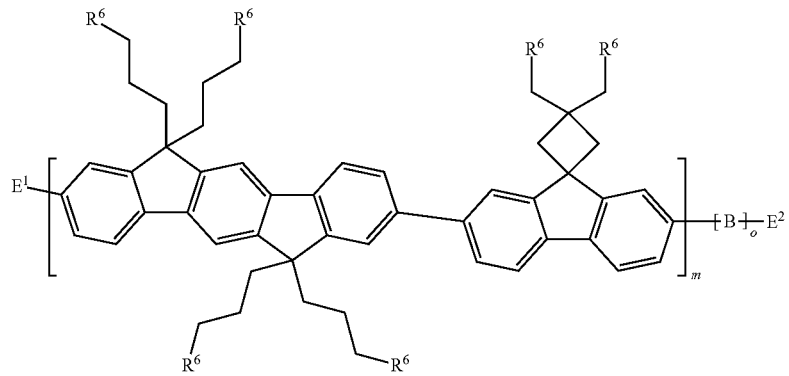
wherein each $R^6$ is independently a water-solubilizing group.
10. The macromer of claim 1, wherein the compound is of the formula:
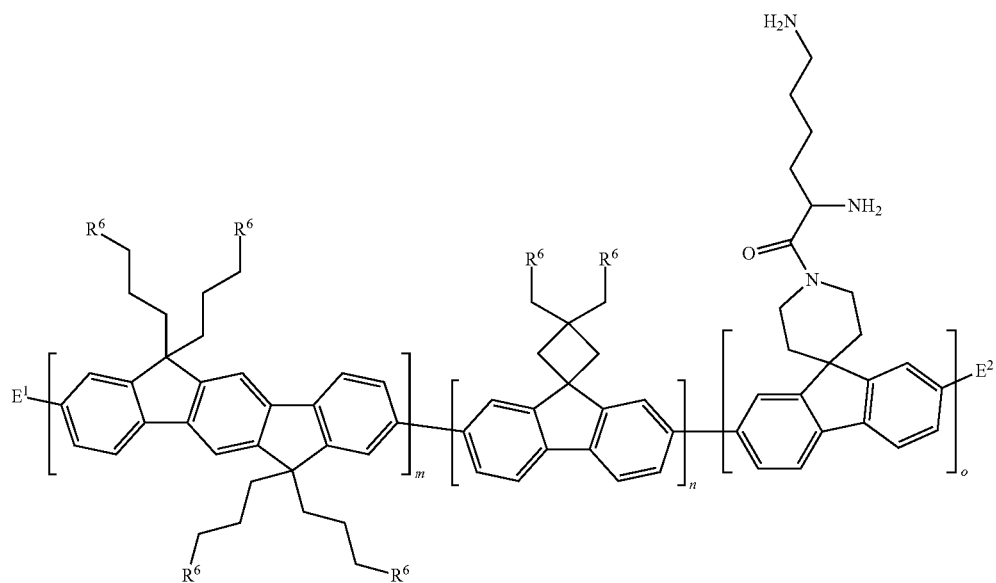
wherein each $R^6$ is a water-solubilizing group; and
m, n and o are each independently a value of 1-50.

11. The macromer of claim 1, wherein the compound is of the formula:

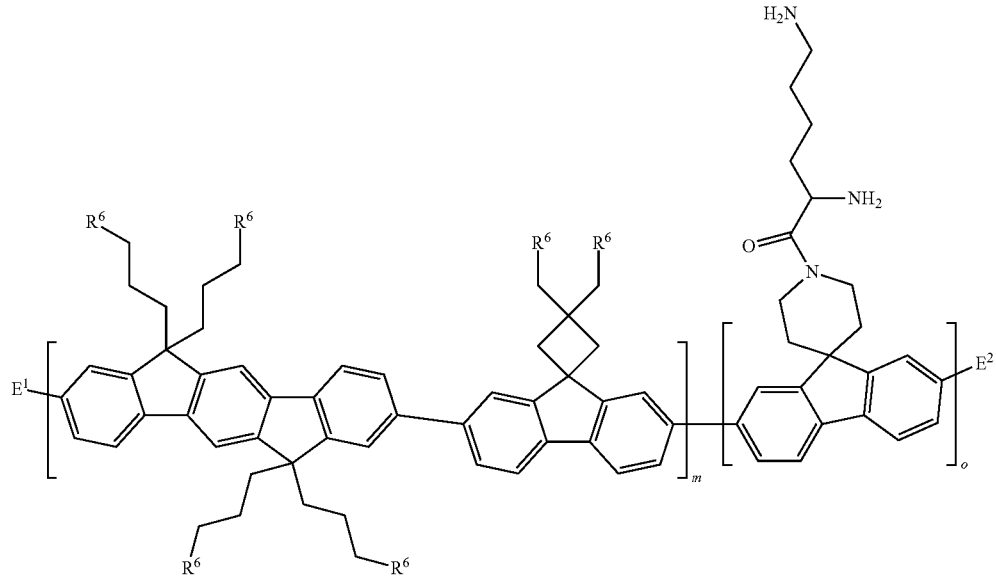

wherein each $R^6$ is a water-solubilizing group; and
m, n and o are each independently a value of 1-50.

12. The macromer of claim 10, wherein each $R^6$ is a an ethylene oxide oligomer methyl ether selected from the group consisting of —O—$PEG_{11}$-$OCH_3$ and —O—PEG550-$OCH_3$.

13. The macromer of claim 1, wherein the compound is of the formula:

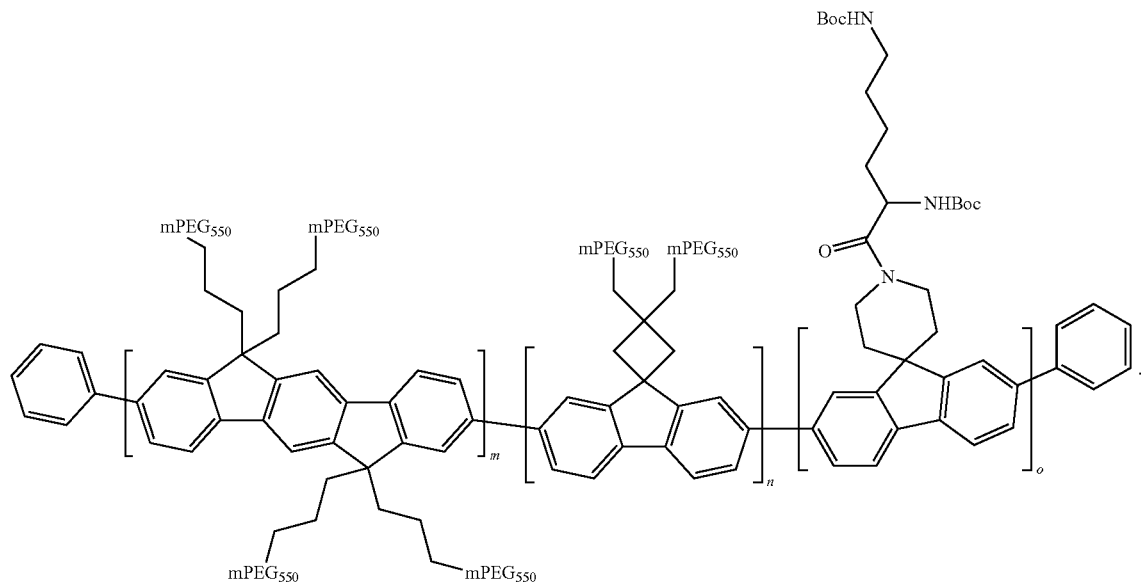

14. The macromer of claim 1, wherein the compound is of the formula:
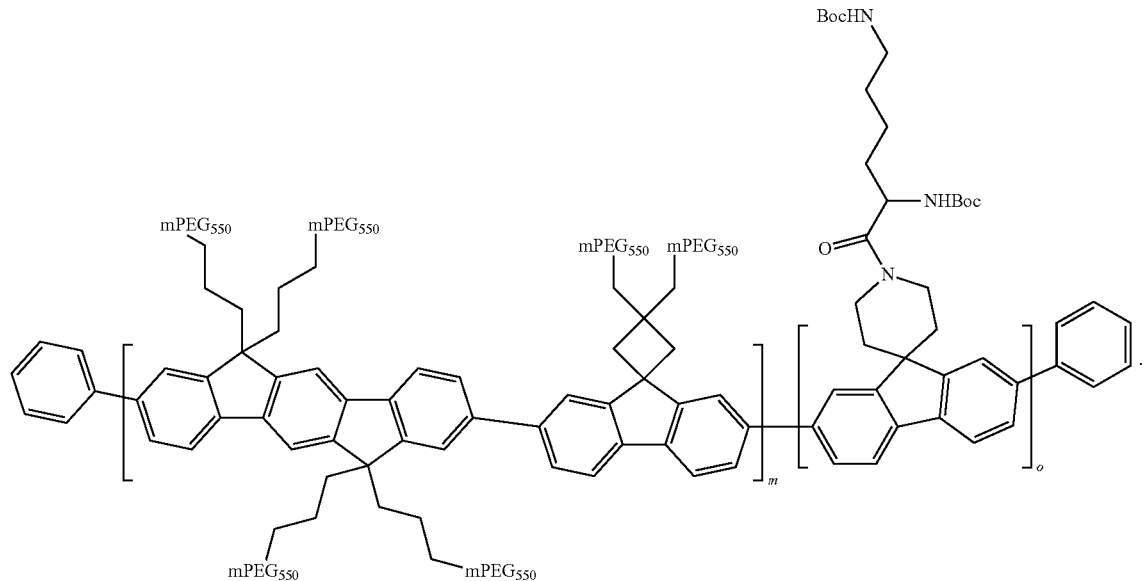
15. The macromer of claim 13, wherein the Boc group is converted to a an amine.
16. The macromer of claim 1, wherein the compound is of the formula:
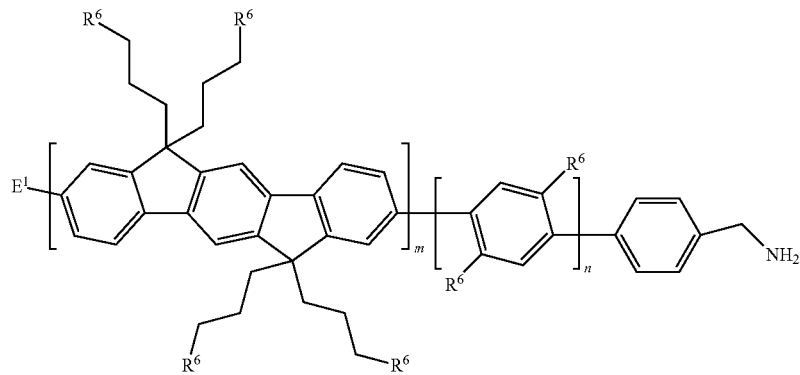
wherein each $R^6$ is an ethylene oxide oligomer methyl ether.
17. The macromer of claim 16, wherein the ethylene oxide oligomer methyl ether is —O—$PEG_{11}$-$OCH_3$ or —O—PEG550-$OCH_3$.

18. The macromer of claim 1, wherein the compound is of the formula:

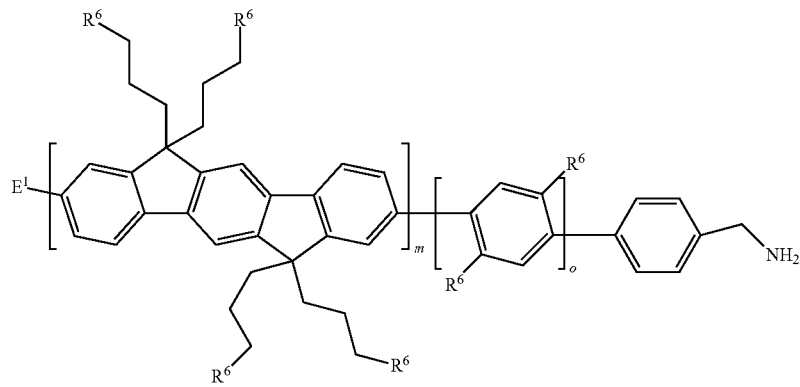

wherein each $R^6$ is an ethylene oxide oligomer methyl ether.

19. The macromer of claim 18, wherein the ethylene oxide oligomer methyl ether is —O—$PEG_{11}$-$OCH_3$ or —O—$PEG_{550}$-$OCH_3$.

20. The macromer of claim 1, wherein the compound is of the formula:

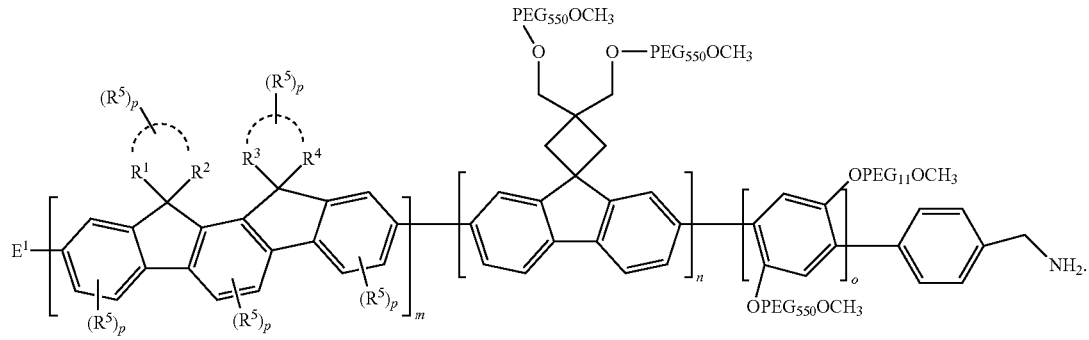

21. The macromer of claim 1, wherein each of A and B if present, is a divalent substituent member selected from the group consisting of benzene, naphthalene, anthracene, benzodiathiazolyl, fluorene, indenofluorene, thiophene, thienothiophene, dithienothiophene, 3,4-ethylenedioxythiophene, furan, pyridine, pyrrole, fused pyrrole, tetrahydropyrene and oxadiazole, wherein each of the foregoing is optionally substituted.

22. The macromer of claim 1, wherein the compound is of the formula:

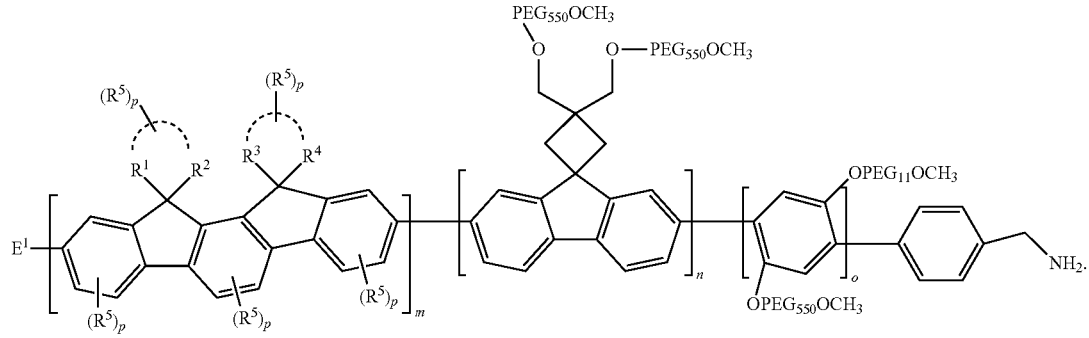

23. A method for detecting a target biomolecule in a sample, said method comprising:
- providing a sample that is suspected of containing a target analyte;
- providing a macromer of claim 1;
- conjugated to a capture molecule, wherein the capture molecule is capable of interacting with the target analyte;
- contacting the sample with the capture molecule and the conjugated macromer under conditions in which the capture molecule can bind to the target analyte if present;
- applying a light source to the sample that excites the conjugated macromer; and detecting whether light is emitted from the conjugated macromer.

* * * * *